United States Patent [19]

Leveen et al.

[11] Patent Number: 4,949,400

[45] Date of Patent: Aug. 14, 1990

[54] HAND HELD GLUCOSE COLORIMETER DEVICE

[76] Inventors: Harry H. Leveen, 321 Confederate Cir., Charleston, S.C. 29407; William F. Kahler, 519 Main Rd., Johns Island, S.C. 29455; Stephen D. Kahler, 1023 Wappoo Rd., Suite 41-B, Charleston, S.C. 29407

[21] Appl. No.: 176,331

[22] Filed: Mar. 31, 1988

[51] Int. Cl.⁵ ........................ G01J 3/50; G01N 21/77
[52] U.S. Cl. .................... 356/420; 356/432; 356/440
[58] Field of Search ............ 356/36, 38, 39, 402, 356/407, 409, 420, 425, 432, 436, 440, 446; 128/770, 630, 636; 364/413.07, 413.09, 413.11

[56] References Cited

U.S. PATENT DOCUMENTS

| | | | |
|---|---|---|---|
| 2,554,414 | 5/1951 | McClendon | 422/91 |
| 4,552,458 | 11/1985 | Lowne | 356/446 |
| 4,637,403 | 1/1987 | Garcia et al. | 128/770 |
| 4,755,058 | 7/1988 | Shaffer | 356/446 |

*Primary Examiner*—F. L. Evans

[57] ABSTRACT

A method and apparatus for increasing the sensitivity and accuracy of apparatus used in chemical analysis utilizing the colorimeter method. The method employs two or more light emitting diodes which emit light at different wavelengths. The emission wavelength of the L.E.D. is automatically switched to an L.E.D. which most closely matches any desired absorption band in the solution being analyzed so that more or less absorption will occur in each range. A logic circuit which utilizes the initial optical density to choose the proper L.E.D. for the particular range of concentration of chromophore. Thus, a green emitting diode may be used to register an initial color change and automatically switched to a red L.E.D. at any chosen concentration.

8 Claims, 5 Drawing Sheets

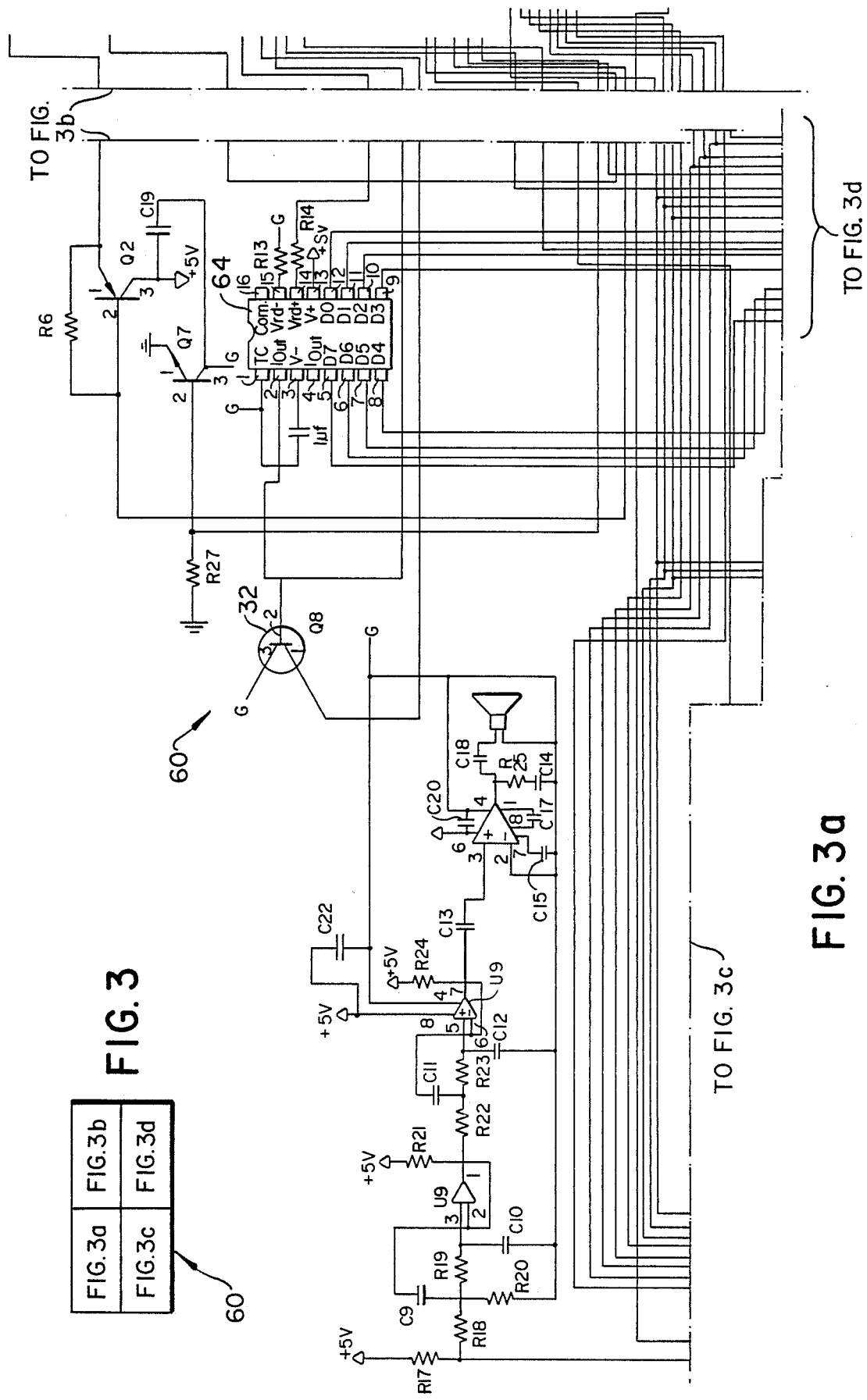

HAND HELD GLUCOSE COLORIMETER DEVICE

BACKGROUND OF THE INVENTION

Colorimeters have employed white incandescent light and utilized color filters to select the proper color range for absorption. The choice of incandescent light is fraught with error because incandescent light is power consuming, varies greatly with small changes in voltage, and becomes less bright with time due to deposit of tungsten on the transparent quartz or glass transmitter.

Absorption spectroscopy both in the visible and infrared range has proved extremely valuable for the identification of compounds in solution. The limitations and usefulness of absorption spectroscopy has been covered in many texts eg.: Melon, Analytical Absorption Spectroscopy, John Wiley, NY 1950; Edisbury, Practical Hints on Absorption Spectroscopy, Plenum Press, 1968. The widespread use of absorption spectroscopy has lead to the publications of absorption spectra for almost all known compounds, eg.: Lang, L. Absorption Spectra in the Ultraviolet and Visible Region, Academic Press NY; Data for organic compounds can also be found in "Organic Electronic Spectral Data" by Phillips, Lyle & Jones Interscience Publishers NY. It thus becomes a simple matter to find the absorption spectra of any known substance or indicator. The indicators include those for oxidation-reduction (redox), pH and specific chemicals. When the absorption spectra is known, different frequencies on the absorption curve can be chosen and the proper L.E.D. selected so that the emission spectrum narrowly covers some selected frequency of the absorption spectra.

The absorption for Malachite, a commercial green dye, is maximum at 6000 Å in the orange-red range therefore the solution appears green. This color is the complimentary colors which is not absorbed.

A lesser secondary peak at 4000-4500 Å appears in the violet zone. Very dilute solutions would best be determined with a red or orange emitting L.E.D. to match the absorption peak at 6000 Å. Yet, high concentrations of malachite would be almost totally absorbed at this frequency. Therefore, it would be better to select a violet emitting diode if one wanted to determine high concentrations with less accuracy. If a red L.E.D. were used, dilute concentrations might be more exactly determined but at elevated concentrations the lesser absorption peak would be desirable and the emission spectra automatically switched.

In 1852, Beer observed that for any given thickness of a solution the transmittance of light of any specific wavelength depended exponentially on the concentration of the absorbing species. Thus if one were to plot transmittance against concentration for any specific substance at a specific wavelength, a linear relationship would exist between concentrations and transmittance and the plot would be a straight line. The slope of this straight line would be determined by the specific absorbance of the substance at the particular wavelength of the emitter. When the specific absorbance at one frequency is high, the slope of the line is steep and with lower absorbance at a different frequency it would be more gradual. Obviously, if one wishes to accurately determine the substance at low concentrations the frequency with the steep slope is most desirable. If one wished to determine differences at high concentrations, a lower absorption peak would be preferable.

This problem of sensitivity for high and low ranges has previously been solved by having two different ranges on the same paper strip each with different color changes. This involves two independent circuits with two concentrations placed on the strip. Automatic switching to another L.E.D. better solves this problem without having to set two separate ranges on a single paper strip.

DESCRIPTION OF THE PRIOR ART

U.S. Pat. No. 3,994,590 to Di Martini et al. describes a colorimeter which employs a plurality of light emitting diodes to enable discrete frequency outputs. U.S. Pat. No. 4,566,797 to Kaffka et al. describes the use of two solid state radiation diodes or laser diodes, each of which emits a substantially monochromatic radiation at different wavelengths mounted in a cylinder used in connection with a spectrophotometer while U.S. Pat. No. 4,324,556 to Robertson et al. describes a spectrophotometer using a wave length selection filter to permit selection of a particular wave length emission. U.S. Pat. Nos. 4,319,884; 4,445,239; 4,445,239; 4,313,929; 4,305,664; 4,100,416 are generally concerned with use of selective wave length emissions in optical measuring devices.

SUMMARY OF THE INVENTION

A chemically impregnated strip is inserted into an optic chamber containing two or more different L.E.D.'s on one side and photo transistor on the other side of the strip. Light from the L.E.D. is transmitted across the strip to a phototransistor, which generates a signal to a computer and associated circuitry which is operated by software to give desired glucose concentration data.

BRIEF DESCRIPTION OF THE DRAWINGS

For a more complete understanding of the invention, reference is made to the appended drawings in which:

FIGS. 3 and 3a-3d are schematic diagrams of the computer and circuitry used in the present invention.

DETAILED DESCRIPTION OF THE INVENTION

Figure 1:
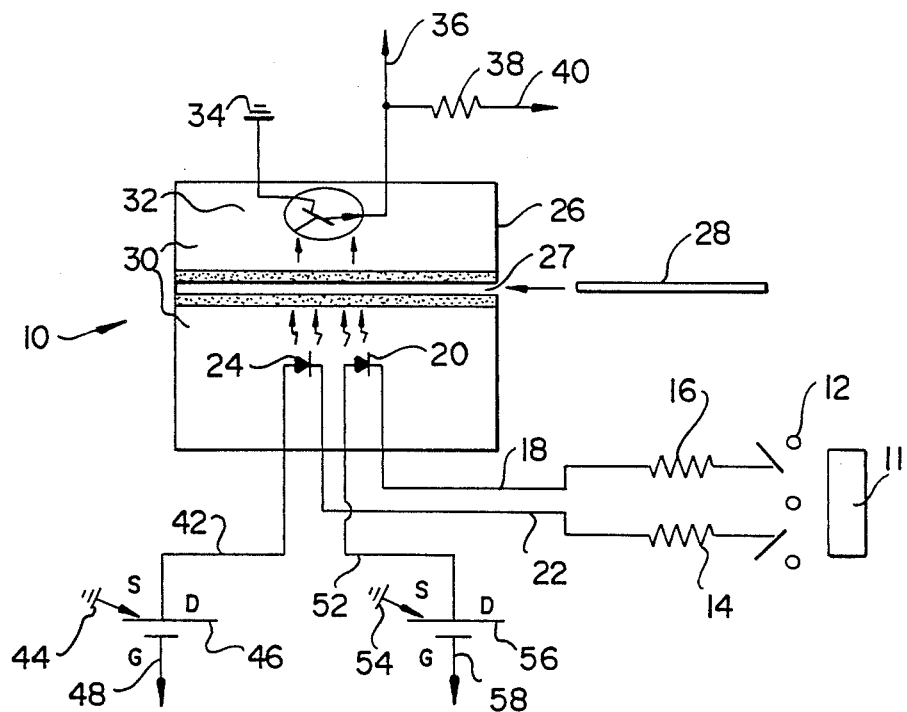
FIG. 1 is a schematic diagram of this invention.
Figure 2:
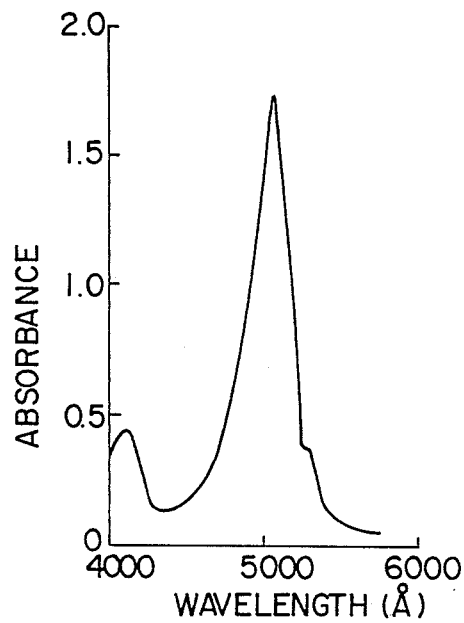
FIG. 2 is an absorption curve for Malachite, a commercial green dye, in aqueous solution.
Figure 3B:
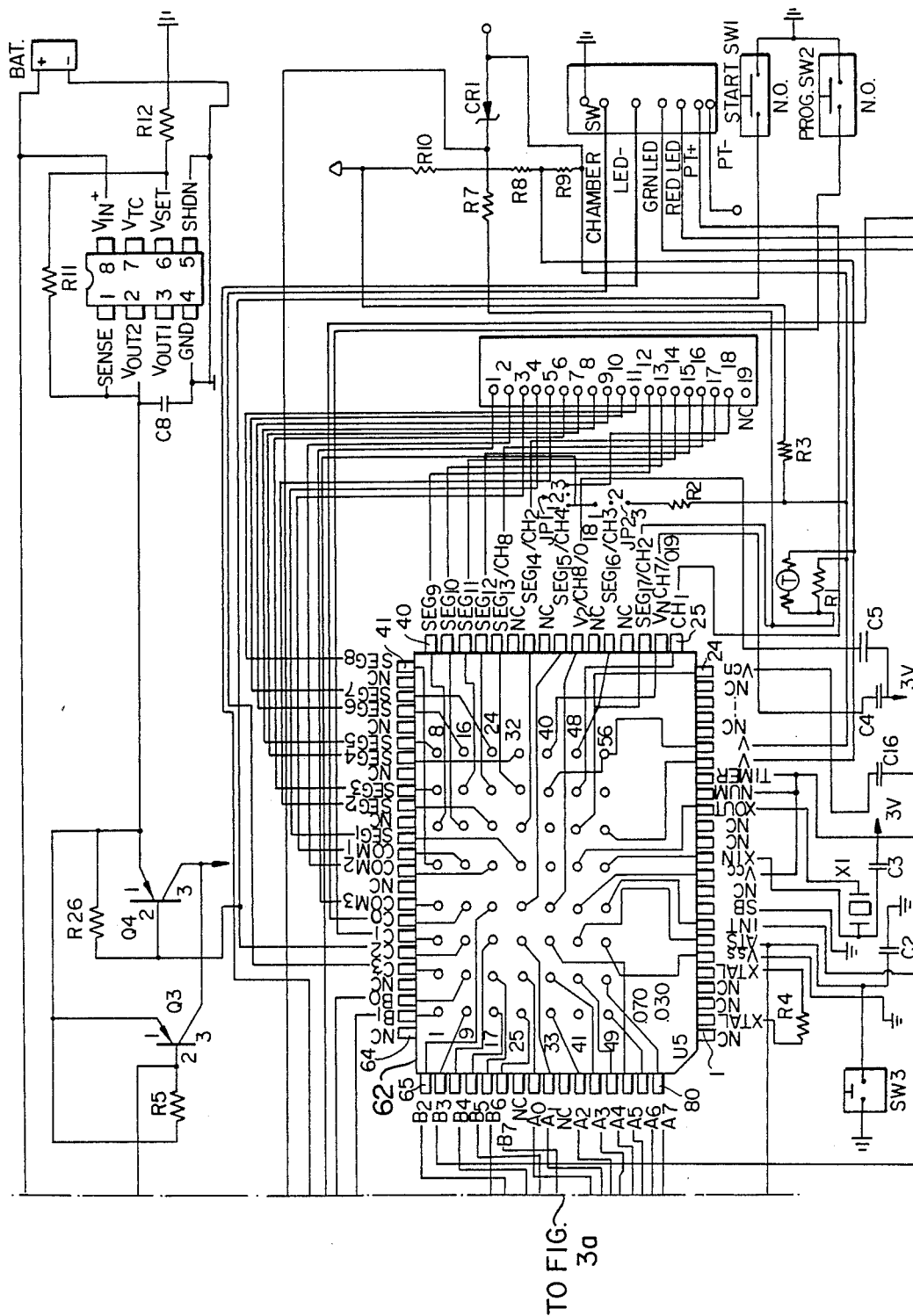
Figure 3C:
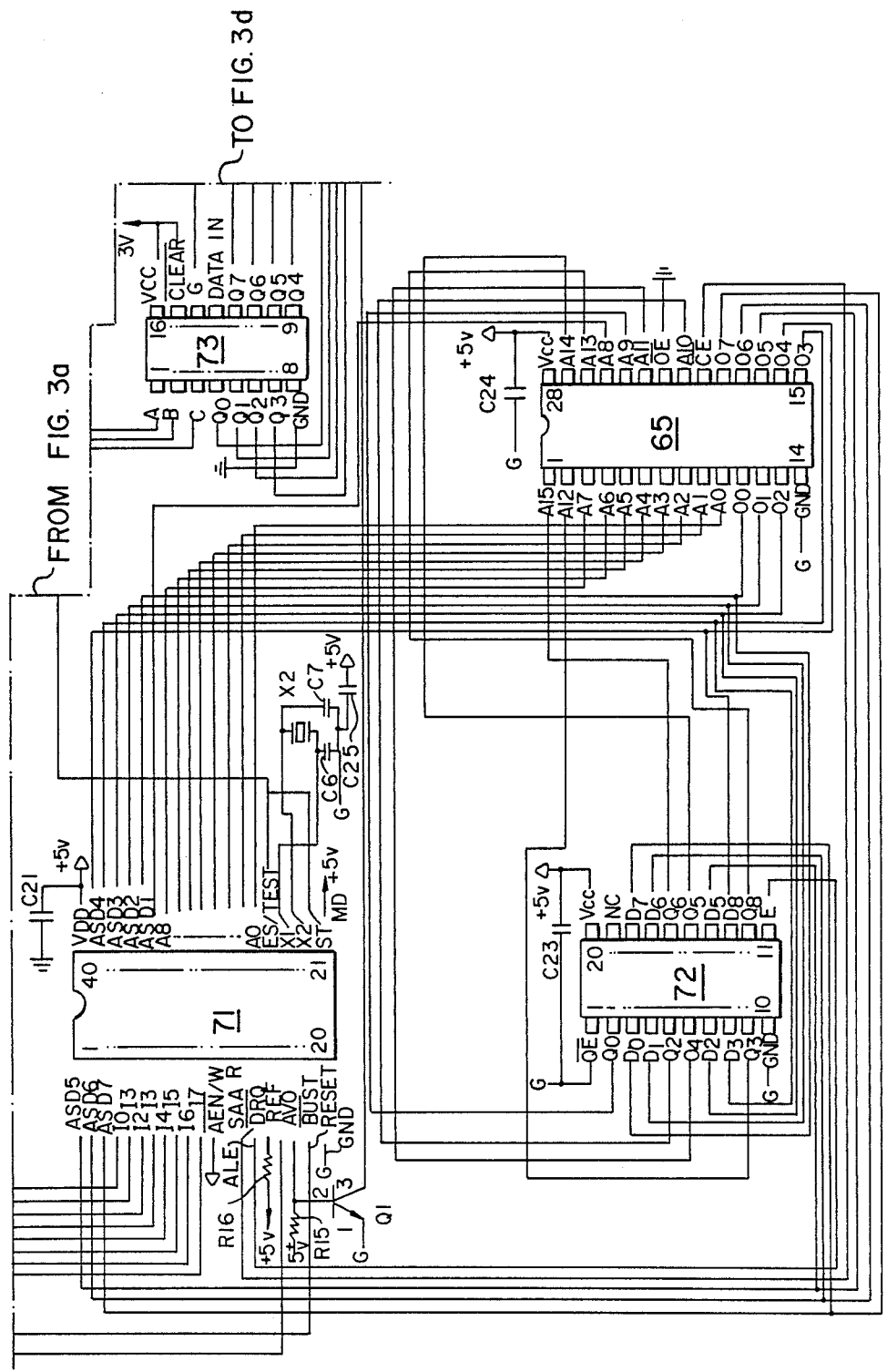
Figure 3D:
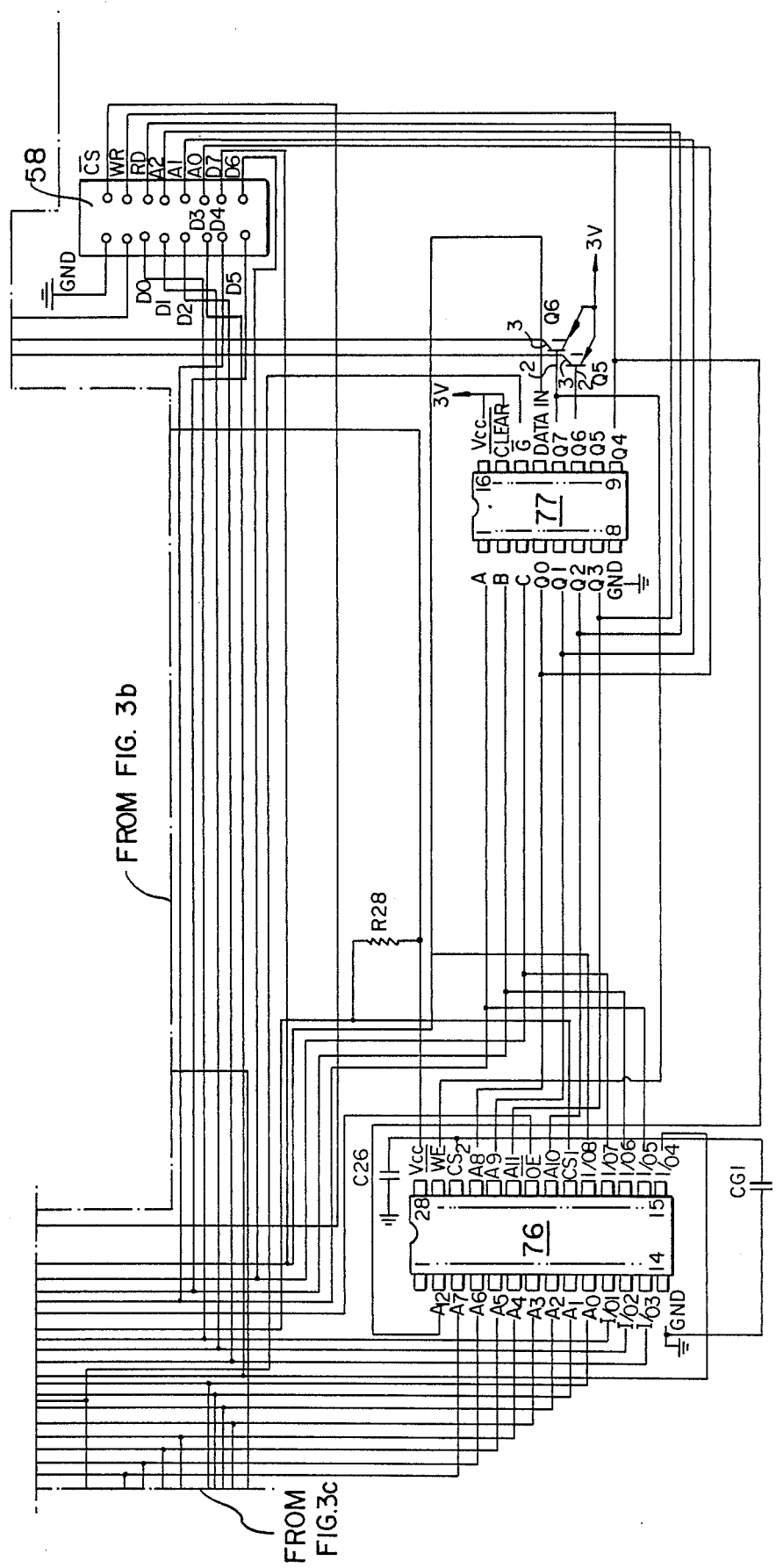

The preferred embodiment and best mode of the invention is shown in FIGS. 1-3. In the invention, a hand held colorimeter 10 is connected to a power source 11 such a batteries. The power source 11 is connected to a switching mechanism 12 which directs the current selectively through resistor 14 and/or resistor 16. These resistors are placed in parallel to respective L.E.D. feed lines 18 and 22 and serve as current limiting resistors to prevent the L.E.D.'s from burning up.

A red light emitting diode 24 is powered via line 22 and a green light emitting diode 20 is powered via line 18. The red L.E.D. would be automatically switched to green at a preselected glucose concentration. The less sensitive absorption would better serve more concentrated solutions. While the present invention uses red and green L.E.D.'s, it is within the scope of the invention to use other color light emitting diodes such as violet to determine various concentrations with varying degrees of accuracy.

Both of the L.E.D.'s 20 and 24 are mounted in the optical chamber 30 to housing 26. A slot 27 is formed in housing 26 into which a chemically reacted test media such as strip 28 is placed. This strip 28 is positioned between the L.E.D.'s 20 and 24 and a photo transistor or photo Darlington 32 which is also positioned in the optical chamber 30 of the housing 26. One arm (cathode) of the photo transistor 32 leads to ground 34 and the other arm (anode) leads to C.P.U. 36 and pull up resistor 38 (R gain) to a voltage source not shown. Thus, a current proportioned to an amount of light being received can be measured. The C.P.U. 36 receives a digital signal from an analog-to-digital converter which changes the analog signal received from the photo transistor into a digital number for readout and interpretation by the C.P.U. The higher the conductivity the greater voltage level.

The L.E.D.'s pass a narrow band of spectral emission usually less than 5000 Å and do not require filters. The intensity of the light does not vary with small voltage differences and consumes far less power than incandescent light. The incorporation of software to switch the light and calculations for concentration of substrate facilitate miniaturization and accuracy.

Many small battery operated hand held devices designated for the colorimeter determination of a single specific substance such as glucose, often contain a chromogenic indicator. A color changes in the indicator is then detected by increased light absorption of light from a light emitting diode. The concentration is sensed by a decrease in the transmission or reflection of light according to Beer and Lambert's Law. If a color change occurs in the chromogenic indicator, the narrow emission spectrum of L.E.D.'s may not suitably match some portions of the absorption spectrum of the chromophore. Therefore, greater sensitivity and accuracy could be achieved in the emission spectrum of the compound. This requires the activation of another L.E.D. with a different emission spectrum. The optical density is sensed by a broad range light sensitive diode which will respond to the emission spectra of all the L.E.D.'s. The L.E.D.'s can be switched at any preprogrammed optical density and the instructions for changing from one L.E.D. to another are contained in the computer software of the device.

The chemical reactions can take place in a small cuvette, test tube or a paper or a plastic translucent, or a paper strip 28. When using a strip 28 the chemical reactants are present on the strip which is moistened with the solution containing the unknown concentration of the chemical to be measured.

When white light is transmitted through a solution of a substance some wavelengths may be either absorbed or passed through the solution. For instance, malachite a commercial green dye absorbs all of other frequencies except green and therefore appears green. By transmitting white light through a solution of a substance and measuring the spectra of the transmitted light, the absorption spectra of the substance can be determined. Indicators are chromophore which change color density and even spectra when the concentration of the test substance is changed.

Thus, the green L.E.D. 20 is turned on if the voltage level from the phototransistor is 0 to 255. The red L.E.D. 24 is then turned on to expand the range of reading by combining the L.E.D.'s to get separate colors.

L.E.D.'s 20 and 24 are connected via line 52 and 42 respectively to grounds 54 and 44, mosfet 46 and 56 and onto the C.P.U. through opto connector 58.

The signal to the C.P.U. and associated circuitry 60 as shown in FIG. 3 begins executing a program which controls various routines relating to information obtained from the display strip 28. The operations circuitry 60 basically comprises a multiprocessor unit 62 Hitachi 63L05 which has a C.P.U. on it and 4K of program storage and 96 bytes of RAM. The M.P.U. is connected to an eight bit analog-to-digital converter 64 which receives the current from photo transistor 32. The analog-to-digital converter has two timers, one of which is a second, time and day clock, the other providing interval time and is placed in a hold mode to limit power consumption. E prom 65 model number 27C512 uses 64 kilobytes with a low pass and high pass filter and stores the determined program for character transfer. A speech processor 71 model NEC7759 is connected to the E prom 65 and takes the speech characteristic from the digital storage of the E prom. An 8 byte addressable latch 73 with a 3 to 8 line decoder is connected to the speech processor and auxillary ram chip storage 76 which is used to store reading and time and date. Another 8 byte addressable latch 77 having the same construction as addressable latch 73 is connected to the printer connector 58 which is bidirectional ported. Chip 72 is an address and input chip known as a tristate output D-type latch. When the program mask chip is turned on, it checks the printer connector bank and if it senses ground, it checks to see if a printer or another computer is connected. If another computer is connected, the proram mask chip begins to communicate and loads a program into the ram of chip 76 which becomes program 6805 assembler.

The program begins executing and this controls various applications such as the display strip readout and associated sub routines to give a number from 0 to 9, 10 to 1000 up to any four digit number in addition to listing various other subcommands such a service requirements, testing, strip acceptability, calibration, result in milliliters, concentration of sample in moles/liter, parts per million etc. The printing results are printed out from a three digit number.

It can thus been seen that the present invention and inventive system provides rapid and convenient access to information of a visual nature taken from optical readings of a chemically treated strip which permits identification by color wavelength to determine various data components and provide medical information. The following is a listing of the control program for the computer which implements the process of the present invention in the hardware combination described above.

```
1      $NOMACEVAL
2      $showincs
3      $paginate
4      $title(INSTRUMENT) subtitle(Pocket LAB)
5      $copyright(Copyright (c) 1988, TEK-AIDS, Inc.)
6      ;
```

```
  7          ;          HD63L05F1F (HITACHI)
  8          ;          HARDWARE CONFIGURATION:
  9          ;
 10          ; MPU PORTS ---
 11          ;IO PA0-PA7 DATA BUS FOR RAM, SPEECH, 8250
 12          ; O PB0     RAM CHIP SELECT (ACTIVE LOW)
 13          ; O PB1     74HC259 GATE INPUT (ACTIVE LOW)
 14          ; O PB2     SPEECH START (ACTIVE LOW)
 15          ; O PB3     8250 CHIP SELECT & PRINT STB (LOW)
 16          ; O PB4     AUXILLIARY POWER V- ON (ACT. HIGH)
 17          ; O PB5     RAM OUTPUT ENABLE (ACTIVE LOW)
 18          ; O PB6     SYSTEM POWER ON (ACTIVE LOW)
 19          ; O PB7     AUXILLIARY POWER V+ ON (ACT. LOW)
 20          ;
 21          ; I PC0     8250/PRINTER SENSE (ACTIVE LOW)
 22          ; I PC1     PROGRAM SWITCH (ACTIVE LOW)
 23          ; I PC2     START SWITCH (ACTIVE LOW)
 24          ; I PC3     OPTO CHAMBER SWITCH (ACTIVE LOW)
 25          ;
 26          ; 74HC259 PORTS ---
 27          ;  259-1 Q0-Q7 RAM A0 -- A7
 28          ;
 29          ;  259-2  Q0     RAM A8 & 8250 A0
 30          ;         Q1     RAM A9 & 8250 A1
 31          ;         Q2     RAM A10 & 8250 A2
 32          ;         Q3     RAM A11 & 8250 RD (ACTIVE LOW)
 33          ;         Q4     RAM A12 & 8250 WR (ACTIVE LOW)
 34          ;         Q5     RAM A13
 35          ;         Q6     RAM A14 & GREEN LED ON (LOW)
 36          ;         Q7     RAM WR EN. & RED LED ON (LOW)
 37          ;
 38          ;
 39          ; EXTERNAL RAM MEMORY USAGE MAP:
 40          ;
 41          ;  00 -- 9B       LCD PIN CONFIGURATION
 42          ;  9C             STACK POINTER
 43          ;  9D -- FF       STACK AREA
 44          ;  100 -- 101     AA, 55 (PROGRAM INDICATOR)
 45          ;  102 -- (END)   PROGRAM
 46          ;
 47          ;
 48                    INCLUDE "INSIO.ASM"   ; PORTS & RAM
  1                    DEFSEG  IOAREA,CLASS=PAGE0,START=00H
  2                    SEG     IOAREA
0000& (0001)   3       PADATA  DS       1       ;PORT A DATA
0001& (0001)   4       PBDATA  DS       1       ;PORT B DATA
0002& (0001)   5       PCDATA  DS       1       ;PORT C DATA
               6                                ;(LOWER 4 BITS ONLY)
0003& (0001)   7               DS       1
0004& (0001)   8       PADIR   DS       1       ;PORT A DIRECTION
0005& (0001)   9       PBDIR   DS       1       ;PORT B DIRECTION
0006& (0001)  10       PCDIR   DS       1       ;PORT C DIRECTION
              11                                ;(LOWER 4 BITS ONLY)
0007& (0001)  12               DS       1
0008& (0001)  13       TIMDATA DS       1       ;TIMER DATA
0009& (0001)  14       TIMCTRL DS       1       ;TIMER CONTROL
              15                                ;BIT0-2 # OF
              16                                ;       PRE-SCALER
              17                                ;       BITS
              18                                ;BIT3   NOT USED
              19                                ;BIT4   MODE SELECT
              20                                ;       1 = TIMER
              21                                ;       0 = COUNTER
              22                                ;BIT5   CLOCK SELECT
              23                                ;       1 = 100kHZ
              24                                ;       0 = 32 kHZ
              25                                ;BIT6   INTERRUPT
              26                                ;       MASK
              27                                ;       1=MASKED
              28                                ;       0=NOT MASKED
              29                                ;BIT7 - INT REQUEST
000A& (0004)  30               DS       4
000E& (0001)  31       ADCDATA DS       1       ;ANALOG INPUT DATA
```

```
 000F& (0001)        32        ADCCTRL   DS      1       ;A/D CONVERTER
                     33                                  ;CONTROL REGISTER
                     34                                  ;BIT0-2 CHANNEL
                     35                                  ;       SELECT
                     36                                  ;       000 = CH1
                     37                                  ;       001 = CH2
                     38                                  ;       010 = CH3
                     39                                  ;       011 = CH4
                     40                                  ;BIT3   COMPARATOR
                     41                                  ;       OUTPUT
                     42                                  ;BIT4   OPERATION
                     43                                  ;       MODE
                     44                                  ;       1=COMPARATOR
                     45                                  ;       0=8 BIT ADC
                     46                                  ;BIT5   1 = START
                     47                                  ;       CONVERSION
                     48                                  ;       SET TO 0 WHEN
                     49                                  ;       CONVERSION
                     50                                  ;       COMPLETE
                     51                                  ;BIT6   INTERRUPT
                     52                                  ;       MASK
                     53                                  ;       1=MASKED
                     54                                  ;       0=NOT MASKED
                     55                                  ;BIT7   INTERRUPT
                     56                                  ;       FLAG
 0010& (0004)        57                  DS      4
 0014& (0001)        58        PLCD1     DS      1       ;LCD REGISTER 1
                     59                                  ;BIT0 - COM2/SEG2
                     60                                  ;BIT1 - COM3/SEG2
                     61                                  ;BIT2 - COM1/SEG3
                     62                                  ;BIT3 - COM1/SEG2
                     63                                  ;BIT4 - COM1/SEG1
                     64                                  ;BIT5 - COM2/SEG1
                     65                                  ;BIT6 - COM3/SEG1
                     66                                  ;BIT7 - NOT USED
 0015& (0001)        67        PLCD2     DS      1       ;LCD REGISTER 2
                     68                                  ;BIT0 - COM2/SEG4
                     69                                  ;BIT1 - COM3/SEG5
                     70                                  ;BIT2 - COM2/SEG5
                     71                                  ;BIT3 - COM1/SEG4
                     72                                  ;BIT4 - COM2/SEG3
                     73                                  ;BIT5 - COM3/SEG3
                     74                                  ;BIT6 - COM3/SEG4
                     75                                  ;BIT7 - NOT USED
 0016& (0001)        76        PLCD3     DS      1       ;LCD REGISTER 3
                     77                                  ;BIT0 - COM2/SEG6
                     78                                  ;BIT1 - COM2/SEG7
                     79                                  ;BIT2 - COM1/SEG7
                     80                                  ;BIT3 - COM1/SEG6
                     81                                  ;BIT4 - COM1/SEG5
                     82                                  ;BIT5 - COM3/SEG6
                     83                                  ;BIT6 - COM3/SEG7
                     84                                  ;BIT7 - NOT USED
 0017& (0001)        85        PLCD4     DS      1       ;LCD REGISTER 4
                     86                                  ;BIT0 - COM2/SEG9
                     87                                  ;BIT1 - COM3/SEG9
                     88                                  ;BIT2 - COM1/SEG10
                     89                                  ;BIT3 - COM1/SEG9
                     90                                  ;BIT4 - COM1/SEG8
                     91                                  ;BIT5 - COM2/SEG8
                     92                                  ;BIT6 - COM3/SEG8
                     93                                  ;BIT7 - NOT USED
 0018& (0001)        94        PLCD5     DS      1       ;LCD REGISTER 5
                     95                                  ;BIT0 - COM2/SEG11
                     96                                  ;BIT1 - COM3/SEG12
                     97                                  ;BIT2 - COM2/SEG12
                     98                                  ;BIT3 - COM1/SEG11
                     99                                  ;BIT4 - COM2/SEG10
                    100                                  ;BIT5 - COM3/SEG10
                    101                                  ;BIT6 - COM3/SEG11
                    102                                  ;BIT7 - NOT USED
 0019& (0001)       103        PLCD6     DS      1       ;LCD REGISTER 6
                    104                                  ;BIT0 - COM2/SEG13
```

```
                        105                                    ;BIT1 - COM2/SEG14
                        106                                    ;BIT2 - COM1/SEG14
                        107                                    ;BIT3 - COM1/SEG13
                        108                                    ;BIT4 - COM1/SEG12
                        109                                    ;BIT5 - COM3/SEG13
                        110                                    ;BIT6 - COM3/SEG14
                        111                                    ;BIT7 - NOT USED
  001A& (0001)          112         PLCD7    DS     1          ;LCD REGISTER 7
                        113                                    ;BIT0 - COM2/SEG16
                        114                                    ;BIT1 - COM3/SEG16
                        115                                    ;BIT2 - COM1/SEG17
                        116                                    ;BIT3 - COM1/SEG16
                        117                                    ;BIT4 - COM1/SEG15
                        118                                    ;BIT5 - COM2/SEG15
                        119                                    ;BIT6 - COM3/SEG15
                        120                                    ;BIT7 - NOT USED
  001B& (0001)          121         PLCD8    DS     1          ;LCD REGISTER 8
                        122                                    ;BIT0 - COM2/SEG17
                        123                                    ;BIT1 - COM3/SEG17
                        124                                    ;BIT2 - NOT USED
                        125                                    ;BIT3 - NOT USED
                        126                                    ;BIT4 - NOT USED
                        127                                    ;BIT5 - NOT USED
                        128                                    ;BIT6 - NOT USED
                        129                                    ;BIT7 - NOT USED
  001C& (0001)          130         SYSCTRL  DS     1          ;SYSTEM CONTROL REG
                        131                                    ;BIT0-1 LCD DUTY BIT
                        132                                    ;       TYPE OF PORT
                        133                                    ;       FOR SEG 1-17
                        134                                    ;       00=OUTPUT
                        135                                    ;       01=STATIC LCD
                        136                                    ;       03=1/3 DUTY
                        137                                    ;          CYCLE LCD
                        138                                    ;BIT2   EXT(SET TO 0)
                        139                                    ;BIT3   HALT MPU
                        140                                    ;BIT4   TIME BASE
                        141                                    ;       RESET
                        142                                    ;BIT5   TIME BASE
                        143                                    ;       SELECT
                        144                                    ;       1=1 SECOND
                        145                                    ;       0=1/16 SECOND
                        146                                    ;BIT6   TIME BASE
                        147                                    ;       INTERRUPT
                        148                                    ;       MASK
                        149                                    ;BIT7   TIME BASE
                        150                                    ;       INTERRUPT
                        151                                    ;       FLAG
  001D& (0003)          152                  DS     3
  0020& (0001)          153         SAVE259  DS     1          ;SAVE LOW AND HIGH
                        154                                    ;HALVES OF PADATA
                        155                                    ;WHEN USED FOR 259
                        156                                    ;I/O.
  0021& (0001)          157         LCD1     DS     1          ;
  0022& (0001)          158         LCD2     DS     1          ;
  0023& (0001)          159         LCD3     DS     1          ;IDENTICAL TO ABOVE
  0024& (0001)          160         LCD4     DS     1          ;LCD PORTS EXCEPT
  0025& (0001)          161         LCD5     DS     1          ;THESE MAY BE USED
  0026& (0001)          162         LCD6     DS     1          ;FOR BIT I/O WHERE
  0027& (0001)          163         LCD7     DS     1          ;THE OTHER ONES ARE
  0028& (0001)          164         LCD8     DS     1          ;WRITE ONLY.
  0029& (0001)          165         SEGVAL   DS     1          ;TO STORE 7 SEGMENT
                        166                                    ;VALUE (BITWISE).
  002A& (0001)          167         SEGLOC   DS     1          ;TO STORE LCD POS.
                        168                                    ;(0-3) TO WRITE INTO.
  002B& (0001)          169         ANCOUNT  DS     1          ;TO STORE # OF
                        170                                    ;ANALOG CONVERSIONS
                        171                                    ;AND TO RETURN
                        172                                    ;ANALOG RESULT.
  002C& (0001)          173         TIMDLY   DS     1          ;# OF 1/16 SECOND
                        174                                    ;TO WAIT.
  002D& (0001)          175         HALTSW   DS     1          ;
                        176             ;   BIT0 ------ SENSE INPUT
                        177             ;   BIT1 ------ PROGRAM SWITCH
```

```
                        178        ;      BIT2 ------ START SWITCH
                        179        ;      BIT3 ------ CHAMBER SWITCH
                        180        ;      BIT4 ------ HOUR CHANGE SWITCH
                        181        ;      BIT5 ------ GREEN LED SWITCH
                        182        ;      BIT6 ------ RED LED SWITCH
                        183        ;      BIT7 ------ PRINTER TIME OUT
002E& (0001)            184        BATTVOLT  DS    1         ;BATTERY VOLTAGE
002F& (0001)            185        TEMP      DS    1         ;TEMPERATURE
0030& (0001)            186        LEDLVL    DS    1         ;LED BRIGHTNESS
0031& (0001)            187        REGPTR    DS    1         ;REGISTER POINTER
0032& (000C)            188        REGSTK    DS    12        ;REGISTER SAVE STACK
003E& (0001)            189        REGSAV    DS    1         ;REG. SAVE TEMP
003F& (0001)            190        ADDR8250  DS    1
                        191        ;      BIT0/1/2 -- REGISTER ADDRESS IN 8250
                        192        ;      BIT3 ------ SENSE INPUT (C0) NOT LOW
                        193        ;      BIT4 ------ I/O TIME OUT
                        194        ;      BIT5 ------ OVERRUN ERROR BIT IN LSR
                        195        ;      BIT6 ------ PARITY ERROR IN LSR
                        196        ;      BIT7 ------ FRAMING ERROR IN LSR
0040& (0001)            197        DATA8250  DS    1         ;I/O DATA FROM 8250
0041& (0001)            198        XSW       DS    1
                        199        ;      BIT0 ---- TIMER INTERRUPT SWITCH
                        200        ;      BIT1 ---- SPEECH INTERRUPT SWITCH
                        201        ;      BIT2 ---- TIMER RETURN SWITCH
                        202        ;      BIT3 ---- OP CODE BRANCH SWITCH
                        203        ;      BIT4 ---- LCD ZERO DISPLAY SWITCH
                        204        ;      BIT5 ---- LEAP YEAR SWITCH
                        205        ;      BIT6/7 -- RAM DATA ACCESS SWITCH
                        206        ;              00 = PROGRAM RAM ACCESS
                        207        ;              01 = OP CODE FETCH FROM RAM
                        208        ;              02 = DATA FETCH/STORE FROM RAM
=0042& (0001)           209        RAMADRL   DS    1         ;ADDRESS
 0043& (0001)           210        RAMADRH   DS    1         ;FOR RAM I/O
 0044& (0001)           211        RAMDATA   DS    1         ;NORMAL DATA
 0045& (0001)           212        OPDATA    DS    1         ;OP CODE DATA
 0046& (0001)           213        XDATA     DS    1         ;OTHER ACCESS
 0047& (0002)           214        DISPWORD  DS    2         ;STORE 16 BIT #
 0049& (0001)           215        STKSAV    DS    1         ;RAM STACK TEMP.
 004A& (0001)           216        TIKSEC    DS    1         ;SECONDS
 004B& (0001)           217        TIKMIN    DS    1         ;MINUTES
 004C& (0001)           218        TIKHR     DS    1         ;HOURS
 004D& (0001)           219        TIKDY     DS    1         ;DAY OF MONTH
 004E& (0001)           220        TIKMO     DS    1         ;MONTH
 004F& (0001)           222        TIKYR     DS    1         ;YEAR
 0050& (0001)           223        LCDSAV    DS    1         ;LCD I/O TEMP.
 0051& (0001)           224        XDATAH    DS    1         ;ADDRESS FOR
 0052& (0001)           225        XDATAL    DS    1         ;OTHER RAM I/O
 0053& (0001)           226        RAMDATAH  DS    1         ;RAM I/O
 0054& (0001)           227        RAMDATAL  DS    1         ;ADDRESS
 0055& (0001)           228        PCTRL     DS    1         ;RAM PROGRAM
 0056& (0001)           229        PCTRH     DS    1         ;COUNTER
 0057& (0001)           230        AREG      DS    1         ;RAM A REGISTER
 0058& (0001)           231        XREG      DS    1         ;RAM X REGISTER
 0059& (0001)           232        CCR       DS    1         ;RAM COND. CODE REG
 005A& (0001)           233        XSUB1     DS    1         ;USED TO
 005B& (0001)           234        XSUB2     DS    1         ;EXECUTE A RAM
 005C& (0001)           235        XSUB3     DS    1         ;OP CODE
 005D& (0001)           236        XSUBRTS1  DS    1         ;
 005E& (0001)           237        XSUBSWI   DS    1         ;
 005F& (0001)           238        XSUBRTS2  DS    1         ;
 0060& (0020)           239        STKAREA   DS    32        ;MPU STACK
                        240
                         49                   INCLUDE "INSROM.ASM" ; PAGE ZERO ROM
 0080& 3F                1        LCDTABL   DB    3FH       ; "0"   ----  0
 0081& 06                2                  DB    06H       ; "1"         1
 0082& 5B                3                  DB    5BH       ; "2"         2
 0083& 4F                4                  DB    4FH       ; "3"         3
 0084& 66                5                  DB    66H       ; "4"         4
 0085& 6D                6                  DB    6DH       ; "5"         5
 0086& 7D                7                  DB    7DH       ; "6"         6
 0087& 07                8                  DB    07H       ; "7"         7
 0088& 7F                9                  DB    7FH       ; "8"         8
 0089& 67               10                  DB    67H       ; "9"         9
```

```
008A& 77            11              DB     77H       ; "A"     10
008B& 7C            12              DB     7CH       ; "b"     11
008C& 39            13              DB     39H       ; "C"     12
008D& 5E            14              DB     5EH       ; "d"     13
008E& 79            15              DB     79H       ; "E"     14
008F& 71            16              DB     71H       ; "F"     15
0090& 00            17              DB     00H       ; " "     16
0091& 09            18              DB     09H       ; "I"     17
0092& 73            19              DB     73H       ; "P"     18
0093& 36            20              DB     36H       ; "W"     19
0094& BF 3E&        21     REGSAVE  STX    REGSAV
0096& BE 31&        22              LDX    REGPTR
0098& E7 32&        23              STA    REGSTK,X
009A& 5C            24              INCX
009B& B6 3E&        25              LDA    REGSAV
009D& E7 32&        26              STA    REGSTK,X
009F& 5C            27              INCX
00A0& BF 31&        28              STX    REGPTR
00A2& 81            29              RTS
00A3& BE 31&        30     REGLOAD  LDX    REGPTR
00A5& 5A            31              DECX
00A6& E6 32&        32              LDA    REGSTK,X
00A8& B7 3E&        33              STA    REGSAV
00AA& 5A            34              DECX
00AB& E6 32&        35              LDA    REGSTK,X
00AD& BF 31&        36              STX    REGPTR
00AF& BE 3E&        37              LDX    REGSAV
00B1& 81            38              RTS
00B2& 1F 1C 1F 1E   39     TIKTABL  DB     31,28,31,30,
00B6& 1F 1E 1F 1F                          31,30,31,31,
00BA& 1E 1F 1E 1F          30,31,30,31
00BE& 1D 41&        40     STKPTR   BCLR   6,XSW
00C0& 1E 41&        41              BSET   7,XSW
00C2& 3F 51&        42              CLR    XDATAH
00C4& AE 9C         43              LDX    #9CH
00C6& BF 52&        44              STX    XDATAL
00C8& 81            45              RTS
00C9& BD BE&        46     STKRST   JSR    STKPTR
00CB& AE FF         47              LDX    #0FFH
00CD& BF 46&        48              STX    XDATA
00CF& CD 09A4&      49              JSR    RAMWRIT
00D2& 81            50              RTS
00D3& BD BE&        51     STKPOP   JSR    STKPTR
00D5& CD 09CA&      52              JSR    RAMREAD
00D8& 3C 46&        53              INC    XDATA
00DA& CD 09A4&      54              JSR    RAMWRIT
00DD& BE 46&        55              LDX    XDATA
00DF& BF 52&        56              STX    XDATAL
00E1& CD 09CA&      57              JSR    RAMREAD
00E4& BE 46&        58              LDX    XDATA
00E6& 81            59              RTS
00E7& BF 49&        60     STKPUSH  STX    STKSAV
00E9& BD BE&        61              JSR    STKPTR
00EB& CD 09CA&      62              JSR    RAMREAD
00EE& 3A 46&        63              DEC    XDATA
00F0& CD 09A4&      64              JSR    RAMWRIT
00F3& BE 46&        65              LDX    XDATA
00F5& 5C            66              INCX
00F6& BF 52&        67              STX    XDATAL
00F8& BE 49&        68              LDX    STKSAV
00FA& BF 46&        69              STX    XDATA
00FC& CD 09A4&      70              JSR    RAMWRIT
00FF& 81            71              RTS
                    72
                    50              DEFSEG MAIN,CLASS=CODE,START=100H
                    51              SEG    MAIN
                    52              INCLUDE "INSMAIN.ASM" ; OP CODE EXEC
                    1      $EJ
                    2      ;************** OPSTART   *********************
                    3      ;*********************************************
                    4      ;
                    5      ;THIS IS THE MAIN PROGRAM WHICH IS EXECUTED
                    6      ;ON MPU POWER ON OR RESET. RFORM THE TURNING
```

```
              7    ;ON OR OFF OF A CERTAIN SEGMENT.
              8    ;
              9    ;***********************************
             10    ;
             11    ;  INPUT : (NONE)
             12    ;
             13    ;  OUTPUT : (NONE)
             14    ;
             15    ;  REGISTERS SAVED (Y/N) : N
             16    ;  IF "N" ABOVE THEN REGISTERS USED.
             17    ;         (* = MODIFIED):
             18    ;                *X REGISTER
             19    ;                *A REGISTER
             20    ;
             21    ;  FIELDS USED (* = MODIFIED):
             22    ;                *PCTRL
             23    ;                *PCTRH
             24    ;                *AREG
             25    ;                *XREG
             26    ;                *CCR
             27    ;                *XSUB1
             28    ;                *XSUB2
             29    ;                *XSUB3
             30    ;                *XSUBSWI
             31    ;                *XSUBRTS1
             32    ;                *XSUBRTS2
             33    ;                *XSW     /BIT:3,6,7
             34    ;                *OPDATA
             35    ;                *XDATAH
             36    ;                *XDATAL
             37    ;                *XDATA
             38    ;
             39    ;  SUBROUTINES CALLED:
             40    ;                MPUINIT
             41    ;                PGMLOAD
             42    ;                STKRST
             43    ;                OPFETCH
             44    ;                OPEXEC
             45    ;                RAMREAD
             46    ;                RAMWRIT
             47    ;                PCTRLOD
             48    ;                PCTRSAV
             49    ;
             50    ;***********************************
0000& CD 0859& 51   OPSTART  JSR    MPUINIT   ;SET INITIAL STATE.
0003& CD 0C7A& 52            JSR    PGMLOAD   ;TRY TO LOAD A PGM.
0006& BD C9&   53            JSR    STKRST    ;SET EXT. RAM STACK.
0008& A6 02    54            LDA    #02H      ;SET RAM OP CODE
000A& B7 55&   55            STA    PCTRL     ;POINTER TO
000C& A6 01    56            LDA    #01H      ;#0102H.
000E& B7 56&   57            STA    PCTRH     ;
0010& 3F 57&   58            CLR    AREG      ;INITIALIZE
0012& 3F 58&   59            CLR    XREG      ;PSEUDO PROGRAM
0014& 3F 59&   60            CLR    CCR       ;REGISTERS.
0016& A6 81    61            LDA    #81H      ;PUT CODE FOR "RTS"
0018& B7 5D&   62            STA    XSUBRTS1  ;INSTRUCTION IN
001A& B7 5F&   63            STA    XSUBRTS2  ;MPU MEMORY.
001C& A6 83    64            LDA    #83H      ;PUT CODE FOR "SWI"
001E& B7 5E&   65            STA    XSUBSWI   ;INSTRUCTION IN RAM.
0020& A6 90    66   OPLOOP   LDA    #90H      ;PUT "NOP" CODE
0022& B7 5B&   67            STA    XSUB2     ;IN 2ND AND 3RD
0024& B7 5C&   68            STA    XSUB3     ;BYTES OF INSTR.
0026& 17 41&   69            BCLR   3,XSW     ;SET NO OP BRANCH.
0028& CD 032C& 70            JSR    OPFETCH   ;GET OP CODE.
002B& B6 45&   71            LDA    OPDATA    ;LOAD OPCODE.
002D& B7 5A&   72            STA    XSUB1     ;STORE AT IN POS. #1.
002F& A4 F0    73            AND    #0F0H     ;MASK LOWER HALF.
0031& 44       74            LSRA             ;SHIFT IT RIGHT 2
0032& 44       75            LSRA             ;BITS TO GET 4 BYTE
0033& 97       76            TAX              ;OFFSET & PUT IN X.
0034& DC 0037& 77            JMP    OPLOOP1,X ;INDEXED JUMP TO OP.
0037& CC 0076& 78   OPLOOP1  JMP    OPCODH0   ;BIT TEST & BRANCH
003A& 9D       79            NOP              ;INSTRUCTIONS.
```

| | | | | | |
|---|---|---|---|---|---|
| 003B& CC 00AC& | 80 | | JMP | OPCODH1 | ;BIT SET & RESET |
| 003E& 9D | 81 | | NOP | | ;INSTRUCTIONS. |
| 003F& CC 00B9& | 82 | | JMP | OPCODH2 | ;BRANCH INSTRUCTIONS. |
| 0042& 9D | 83 | | NOP | | ; |
| 0043& CC 00AC& | 84 | | JMP | OPCODH1 | ;RD/MOD/WR DIRECT |
| 0046& 9D | 85 | | NOP | | ;MODE INSTRUCTIONS. |
| 0047& CC 00E8& | 86 | | JMP | OPCODH4 | ;RD/MOD/WR A REGISTER |
| 004A& 9D | 87 | | NOP | | ;INSTRUCTIONS. |
| 004B& CC 00E8& | 88 | | JMP | OPCODH4 | ;RD/MOD/WR X REGISTER |
| 004E& 9D | 89 | | NOP | | ;INSTRUCTIONS. |
| 004F& CC 00AC& | 90 | | JMP | OPCODH1 | ;RD/MOD/WR INDEXED 1 |
| 0052& 9D | 91 | | NOP | | ;BYTE OFFSET. |
| 0053& CC 00E8& | 92 | | JMP | OPCODH4 | ;RD/MOD/WR INDEXED 0 |
| 0056& 9D | 93 | | NOP | | ;BYTE OFFSET. |
| 0057& CC 0226& | 94 | | JMP | OPCODH8 | ;RTI, RTS, OR SWI |
| 005A& 9D | 95 | | NOP | | ;INSTRUCTIONS. |
| 005B& CC 00E8& | 96 | | JMP | OPCODH4 | ;MISC. CONTROL |
| 005E& 9D | 97 | | NOP | | ;INSTRUCTIONS. |
| 005F& CC 00EE& | 98 | | JMP | OPCODHA | ;REG/MEM IMMEDIATE |
| 0062& 9D | 99 | | NOP | | ;INSTRUCTIONS. |
| 0063& CC 00EE& | 100 | | JMP | OPCODHA | ;REG/MEM DIRECT |
| 0066& 9D | 101 | | NOP | | ;INSTRUCTIONS. |
| 0067& CC 0118& | 102 | | JMP | OPCODHC | ;REG/MEM EXTENDED |
| 006A& 9D | 103 | | NOP | | ;ADDRESSING. |
| 006B& CC 0195& | 104 | | JMP | OPCODHD | ;REG/MEM INDEXED 2 |
| 006E& 9D | 105 | | NOP | | ;BYTE OFFSET. |
| 006F& CC 00EE& | 106 | | JMP | OPCODHA | ;REG/MEM INDEXED 1 |
| 0072& 9D | 107 | | NOP | | ;BYTE OFFSET. |
| 0073& CC 0103& | 108 | | JMP | OPCODHF | ;REG/MEM INDEXED 0 |
| | 109 | | | | ;BYTE OFFSET. |
| 0076& CD 032C& | 110 | OPCODH0 | JSR | OPFETCH | ;GET 2ND BYTE OF OP. |
| 0079& B6 45& | 111 | | LDA | OPDATA | ;LOAD IT. |
| 007B& B7 5B& | 112 | | STA | XSUB2 | ;STORE IT IN MEMORY. |
| 007D& A6 01 | 113 | | LDA | #1 | ;BRANCH ONLY +1 BYTE. |
| 007F& B7 5C& | 114 | | STA | XSUB3 | ;STORE IT IN MEMORY. |
| 0081& CD 033E& | 115 | | JSR | OPEXEC | ;EXECUTE INSTRUCTION. |
| 0084& 07 41& 22 | 116 | | BRCLR | 3,XSW,OPCODH0C | ;BRANCH DONE? |
| 0087& CD 032C& | 117 | | JSR | OPFETCH | ;YES, GET OFFSET TO |
| 008A& B6 45& | 118 | | LDA | OPDATA | ;CALC NEW ADDRESS. |
| 008C& 2B 0A | 119 | | BMI | OPCODH0A | ;BACKWARD BRANCH? |
| 008E& BB 55& | 120 | | ADD | PCTRL | ;NO, ADD TO ADDR. |
| 0090& B7 55& | 121 | | STA | PCTRL | ;SAVE IT. |
| 0092& 24 15 | 122 | | BCC | OPCODH0C | ;LOW BYTE PAST 0FFH? |
| 0094& 3C 56& | 123 | | INC | PCTRH | ;YES, HIGH=HIGH+1. |
| 0096& 20 11 | 124 | | BRA | OPCODH0C | ;NEXT INSTRUCTION. |
| 0098& A1 80 | 125 | OPCODH0A | CMP | #80H | ;BRANCH OFFSET |
| 009A& 27 02 | 126 | | BEQ | OPCODH0B | ; = -128? |
| 009C& A4 7F | 127 | | AND | #7FH | ;NO, CLEAR BIT 7. |
| 009E& 97 | 128 | OPCODH0B | TAX | | ;PUT A IN X. |
| 009F& B6 55& | 129 | | LDA | PCTRL | ;LOAD LOW POINTER. |
| 00A1& BF 55& | 130 | | STX | PCTRL | ;PUT OFFSET IN LOW. |
| 00A3& B0 55& | 131 | | SUB | PCTRL | ;LOW=LOW-OFFSET. |
| 00A5& 24 02 | 132 | | BCC | OPCODH0C | ;LOW PAST 0FFH? |
| 00A7& 3A 56& | 133 | | DEC | PCTRH | ;YES, HIGH=HIGH-1. |
| 00A9& CC 0020& | 134 | OPCODH0C | JMP | OPLOOP | ;GO BACK FOR ANOTHER. |
| 00AC& CD 032C& | 135 | OPCODH1 | JSR | OPFETCH | ;GET 2ND BYTE OF OP. |
| 00AF& B6 45& | 136 | | LDA | OPDATA | ;LOAD IT. |
| 00B1& B7 5B& | 137 | | STA | XSUB2 | ;STORE IT IN MEMORY. |
| 00B3& CD 033E& | 138 | | JSR | OPEXEC | ;EXECUTE IT. |
| 00B6& CC 0020& | 139 | | JMP | OPLOOP | ;GO BACK FOR ANOTHER. |
| 00B9& A6 02 | 140 | OPCODH2 | LDA | #2 | ;BRANCH +2 BYTES. |
| 00BB& B7 5B& | 141 | | STA | XSUB2 | ;STORE IT IN MEMORY. |
| 00BD& CD 033E& | 142 | | JSR | OPEXEC | ;EXECUTE IT. |
| 00C0& 07 41& 22 | 143 | | BRCLR | 3,XSW,OPCODH2C | ;BRANCH OCCUR? |
| 00C3& CD 032C& | 144 | | JSR | OPFETCH | ;YES, GET BRANCH |
| 00C6& B6 45& | 145 | | LDA | OPDATA | ;OFFSET. |
| 00C8& 2B 0A | 146 | | BMI | OPCODH2A | ;OFFSET NEGATIVE? |
| 00CA& BB 55& | 147 | | ADD | PCTRL | ;NO, ADD LOW POINTER. |
| 00CC& B7 55& | 148 | | STA | PCTRL | ;STORE LOW POINTER. |
| 00CE& 24 15 | 149 | | BCC | OPCODH2C | ;PASSED #0FFH? |
| 00D0& 3C 56& | 150 | | INC | PCTRH | ;YES, HIGH=HIGH+1 |
| 00D2& 20 11 | 151 | | BRA | OPCODH2C | ;NEXT INSTRUCTION. |
| 00D4& A1 80 | 152 | OPCODH2A | CMP | #80H | ;RAM PROGRAM OFFSET |

| | | | | | |
|---|---|---|---|---|---|
| 00D6& 27 02 | 153 | | BEQ | OPCODH2B; | = -128? |
| 00D8& A4 7F | 154 | | AND | #7FH | ;NO, CLEAR SIGN BIT. |
| 00DA& 97 | 155 | OPCODH2B | TAX | | ;PUT A IN X. |
| 00DB& B6 55& | 156 | | LDA | PCTRL | ;LOAD LOW POINTER. |
| 00DD& BF 55& | 157 | | STX | PCTRL | ;PUT OFFSET IN LOW. |
| 00DF& B0 55& | 158 | | SUB | PCTRL | ;LOW=LOW-OFFSET. |
| 00E1& 24 02 | 159 | | BCC | OPCODH2C; | PASSED #0FFH? |
| 00E3& 3A 56& | 160 | | DEC | PCTRH | ;YES, HIGH=HIGH-1. |
| 00E5& CC 0020& | 161 | OPCODH2C | JMP | OPLOOP | ;NEXT INSTRUCTION. |
| 00E8& CD 033E& | 162 | OPCODH4 | JSR | OPEXEC | ;EXECUTE 1 BYTE OP. |
| 00EB& CC 0020& | 163 | | JMP | OPLOOP | ;GET NEXT INSTR. |
| 00EE& B6 45& | 164 | OPCODHA | LDA | OPDATA | ;GET 1ST BYTE OF OP. |
| 00F0& A4 0F | 165 | | AND | #0FH | 166 |
| 00F2& A1 0C | 167 | | CMP | #0CH | ;LOW HALF |
| 00F4& 27 07 | 168 | | BEQ | OPCODHA1; | = JMP INSTR.? |
| 00F6& A1 0D | 169 | | CMP | #0DH | ;NO, LOW HALF |
| 00F8& 27 06 | 170 | | BEQ | OPCODHA2; | = JSR INSTR.? |
| 00FA& CC 00AC& | 171 | | JMP | OPCODH1 | ;NO,NORMAL 2 BYTE OP. |
| 00FD& CC 022C& | 172 | OPCODHA1 | JMP | OPJUMP | ;GO TO JMP ROUTINE. |
| 0100& CC 028F& | 173 | OPCODHA2 | JMP | OPJSR | ;GO TO JSR ROUTINE. |
| 0103& B6 45& | 174 | OPCODHF | LDA | OPDATA | ;GET 1ST BYTE OF OP. |
| 0105& A4 0F | 175 | | AND | #0FH | 176 |
| 0107& A1 0C | 177 | | CMP | #0CH | ;LOW HALF |
| 0109& 27 07 | 178 | | BEQ | OPCODHF1; | = JMP INSTR.? |
| 010B& A1 0D | 179 | | CMP | #0DH | ;NO, LOW HALF |
| 010D& 27 06 | 180 | | BEQ | OPCODHF2; | = JSR INSTR.? |
| 010F& CC 00E8& | 181 | | JMP | OPCODH4 | ;NO,NORMAL 1 BYTE OP. |
| 0112& CC 022C& | 182 | OPCODHF1 | JMP | OPJUMP | ;GO TO JMP ROUTINE. |
| 0115& CC 028F& | 183 | OPCODHF2 | JMP | OPJSR | ;GO TO JSR ROUTINE. |
| 0118& B6 45& | 184 | OPCODHC | LDA | OPDATA | ;GET 1ST BYTE OF OP. |
| 011A& A4 0F | 185 | | AND | #0FH | 186 |
| 011C& A1 0C | 187 | | CMP | #0CH | ;LOW HALF |
| 011E& 27 06 | 188 | | BEQ | OPCODHC1; | = JMP INSTR.? |
| 0120& A1 0D | 189 | | CMP | #0DH | ;NO, LOW HALF |
| 0122& 27 05 | 190 | | BEQ | OPCODHC2; | = JSR INSTR.? |
| 0124& 20 06 | 191 | | BRA | OPCODHC3; | NO,EXTENDED ADDR. |
| 0126& CC 022C& | 192 | OPCODHC1 | JMP | OPJUMP | ;GO TO JMP ROUTINE. |
| 0129& CC 028F& | 193 | OPCODHC2 | JMP | OPJSR | ;GO TO JSR ROUTINE. |
| 012C& CD 032C& | 194 | OPCODHC3 | JSR | OPFETCH | ;GET 2ND BYTE OF |
| 012F& B6 45& | 195 | | LDA | OPDATA | ;INSTRUCTION. |
| 0131& A1 10 | 196 | | CMP | #10H | ;HIGH BYTE OF ADDR |
| 0133& 24 0F | 197 | | BCC | OPCODHC4; | IN RAM CHIP? |
| 0135& B7 5B& | 198 | | STA | XSUB2 | ;NO, STORE IN MEM. |
| 0137& CD 032C& | 199 | | JSR | OPFETCH | ;GET 3RD BYTE OF |
| 013A& B6 45& | 200 | | LDA | OPDATA | ;INSTRUCTION. |
| 013C& B7 5C& | 201 | | STA | XSUB3 | ;STORE IT IN MEM. |
| 013E& CD 033E& | 202 | | JSR | OPEXEC | ;GO AND EXECUTE IT. |
| 0141& CC 0020& | 203 | | JMP | OPLOOP | ;NEXT INSTRUCTION. |
| 0144& A0 10 | 204 | OPCODHC4 | SUB | #10H | ;YES, MAKE IT POINT |
| 0146& B7 45& | 205 | | STA | OPDATA | ;TO RAM LOCATION. |
| 0148& B6 5A& | 206 | | LDA | XSUB1 | ;LOAD 1ST BYTE OF OP. |
| 014A& A4 0F | 207 | | AND | #0FH | ;MASK OFF HIGH HALF. |
| 014C& A1 07 | 208 | | CMP | #07H | ;IS IT AN STA |
| 014E& 27 28 | 209 | | BEQ | OPCODHC5; | INSTRUCTION? |
| 0150& A1 0F | 210 | | CMP | #0FH | ;NO, IS IT AN STX |
| 0152& 27 28 | 211 | | BEQ | OPCODHC6; | INSTRUCTION? |
| 0154& B6 45& | 212 | | LDA | OPDATA | ;NO, SET HIGH RAM |
| 0156& B7 51& | 213 | | STA | XDATAH | ;ACCES TO OP CODE. |
| 0158& CD 032C& | 214 | | JSR | OPFETCH | ;GET 3RD BYTE OF |
| 015B& B6 45& | 215 | | LDA | OPDATA | ;INSTRUCTION. |
| 015D& B7 52& | 216 | | STA | XDATAL | ;STORE IT IN LOW. |
| 015F& 1D 41& | 217 | | BCLR | 6,XSW | ;SET FOR DATA FETCH |
| 0161& 1E 41& | 218 | | BSET | 7,XSW | ;FROM RAM CHIP. |
| 0163& CD 09CA& | 219 | | JSR | RAMREAD | ;READ RAM. |
| 0166& B6 46& | 220 | | LDA | XDATA | ;GET RAM DATA BYTE. |
| 0168& B7 5B& | 221 | | STA | XSUB2 | ;STORE IN MEMORY. |
| 016A& B6 5A& | 222 | | LDA | XSUB1 | ;GET 1ST BYTE OF OP. |
| 016C& A4 BF | 223 | | AND | #0BFH | ;CHANGE OP CODE TO |
| 016E& AA 20 | 224 | | ORA | #20H | ;IMMEDIATE MODE. |
| 0170& B7 5A& | 225 | | STA | XSUB1 | ;STORE IT. |
| 0172& CD 033E& | 226 | | JSR | OPEXEC | ;EXECUTE INSTRUCTION. |
| 0175& CC 0020& | 227 | | JMP | OPLOOP | ;GO GET ANOTHER. |
| 0178& B6 57& | 228 | OPCODHC5 | LDA | AREG | ;GET PSEUDO REG FOR |

| | | | | | |
|---|---|---|---|---|---|
| 017A& 20 02 | 229 | | BRA | OPCODHC7 | ;STA INSTRUCTION. |
| 017C& B6 58& | 230 | OPCODHC6 | LDA | XREG | ;GET REG FOR STX. |
| 017E& B7 46& | 231 | OPCODHC7 | STA | XDATA | ;STORE IN RAM ACCESS. |
| 0180& B6 45& | 232 | | LDA | OPDATA | ;GET HIGH BYTE OF |
| 0182& B7 51& | 233 | | STA | XDATAH | ;ADDRESS TO WRITE. |
| 0184& CD 032C& | 234 | | JSR | OPFETCH | ;GET 3RD BYTE OF OP. |
| 0187& B6 45& | 235 | | LDA | OPDATA | ;STORE IT IN LOW |
| 0189& B7 52& | 236 | | STA | XDATAL | ;ADDRESS. |
| 018B& 1D 41& | 237 | | BCLR | 6,XSW | ;SET DATA ACCESS |
| 018D& 1E 41& | 238 | | BSET | 7,XSW | ;FOR RAM CHIP. |
| 018F& CD 09A4& | 239 | | JSR | RAMWRIT | ;WRITE DATA TO RAM. |
| 0192& CC 0020& | 240 | | JMP | OPLOOP | ;GO GET ANOTHER. |
| 0195& B6 45& | 241 | OPCODHD | LDA | OPDATA | ;GET 1ST BYTE OF OP. |
| 0197& A4 0F | 242 | | AND | #0FH | 243 |
| 0199& A1 0C | 244 | | CMP | #0CH | ;IS IT A JMP |
| 019B& 27 06 | 245 | | BEQ | OPCODHD1 | ;INSTRUCTION? |
| 019D& A1 0D | 246 | | CMP | #0DH | ;NO, IS IT A JSR |
| 019F& 27 05 | 247 | | BEQ | OPCODHD2 | ;INSTRUCTION? |
| 01A1& 20 06 | 248 | | BRA | OPCODHD3 | ;NO, BRANCH AROUND. |
| 01A3& CC 022C& | 249 | OPCODHD1 | JMP | OPJUMP | ;GO TO JMP ROUTINE. |
| 01A6& CC 028F& | 250 | OPCODHD2 | JMP | OPJSR | ;GO TO JSR ROUTINE. |
| 01A9& CD 032C& | 251 | OPCODHD3 | JSR | OPFETCH | ;GET 2ND BYTE OF OP. |
| 01AC& B6 45& | 252 | | LDA | OPDATA | ;LOAD IT. |
| 01AE& A1 10 | 253 | | CMP | #10H | ;IS IT IN THE |
| 01B0& 24 0F | 254 | | BCC | OPCODHD4 | ;RAM CHIP? |
| 01B2& B7 5B& | 255 | | STA | XSUB2 | ;NO, STORE IN 2ND. |
| 01B4& CD 032C& | 256 | | JSR | OPFETCH | ;GET 3RD BYTE OF OP. |
| 01B7& B6 45& | 257 | | LDA | OPDATA | ;LOAD IT. |
| 01B9& B7 5C& | 258 | | STA | XSUB3 | ;STORE IT IN 3RD. |
| 01BB& CD 033E& | 259 | | JSR | OPEXEC | ;EXECUTE OP CODE. |
| 01BE& CC 0020& | 260 | | JMP | OPLOOP | ;GET ANOTHER. |
| 01C1& A0 10 | 261 | OPCODHD4 | SUB | #10H | ;POINT TO RAM CHIP. |
| 01C3& B7 45& | 262 | | STA | OPDATA | ;STORE IT. |
| 01C5& B6 5A& | 263 | | LDA | XSUB1 | ;GET 1ST BYTE OF OP. |
| 01C7& A4 0F | 264 | | AND | #0FH | ;MASK OFF HIGH HALF. |
| 01C9& A1 07 | 265 | | CMP | #07H | ;IS IT AN STA |
| 01CB& 27 32 | 266 | | BEQ | OPCODHD6 | ;INSTRUCTION? |
| 01CD& A1 0F | 267 | | CMP | #0FH | ;NO, IS IT AN STX |
| 01CF& 27 32 | 268 | | BEQ | OPCODHD7 | ;INSTRUCTION? |
| 01D1& B6 45& | 269 | | LDA | OPDATA | ;NO, GET HIGH ADDR. |
| 01D3& B7 51& | 270 | | STA | XDATAH | ;SAVE FOR RAM ACCESS. |
| 01D5& CD 032C& | 271 | | JSR | OPFETCH | ;GET 3RD BYTE OF OP. |
| 01D8& B6 45& | 272 | | LDA | OPDATA | ;LOAD IT. |
| 01DA& B7 52& | 273 | | STA | XDATAL | ;SAVE IT IN LOW BYTE. |
| 01DC& B6 58& | 274 | | LDA | XREG | ;GET X PSEUDO REG. |
| 01DE& BB 52& | 275 | | ADD | XDATAL | ;ADD TO LOW ADDR. |
| 01E0& B7 52& | 276 | | STA | XDATAL | ;STORE IN LOW BYTE. |
| 01E2& 24 02 | 277 | | BCC | OPCODHD5 | ;PASSED #0FFH? |
| 01E4& 3C 51& | 278 | | INC | XDATAH | ;YES, HIGH=HIGH+1. |
| 01E6& 1D 41& | 279 | OPCODHD5 | BCLR | 6,XSW | ;SET FOR RAM |
| 01E8& 1E 41& | 280 | | BSET | 7,XSW | ;ACCESS. |
| 01EA& CD 09CA& | 281 | | JSR | RAMREAD | ;READ DATA. |
| 01ED& B6 46& | 282 | | LDA | XDATA | ;GET RAM DATA. |
| 01EF& B7 5B& | 283 | | STA | XSUB2 | ;STORE IT IN BYTE 2. |
| 01F1& B6 5A& | 284 | | LDA | XSUB1 | ;GET BYTE 1 OF OP. |
| 01F3& A4 BF | 285 | | AND | #0BFH | ;CHANGE OP CODE TO |
| 01F5& AA 20 | 286 | | ORA | #20H | ;IMMEDIATE MODE. |
| 01F7& B7 5A& | 287 | | STA | XSUB1 | ;STORE IT. |
| 01F9& CD 033E& | 288 | | JSR | OPEXEC | ;EXECUTE OP CODE. |
| 01FC& CC 0020& | 289 | | JMP | OPLOOP | ;GO GET ANOTHER. |
| 01FF& B6 57& | 290 | OPCODHD6 | LDA | AREG | ;GET A PSEUDO REG |
| 0201& 20 02 | 291 | | BRA | OPCODHD8 | ;FOR STA INSTR. |
| 0203& B6 58& | 292 | OPCODHD7 | LDA | XREG | ;GET X PSEUDO REG. |
| 0205& B7 46& | 293 | OPCODHD8 | STA | XDATA | ;SAVE FOR RAM ACCESS. |
| 0207& B6 45& | 294 | | LDA | OPDATA | ;GET 2ND BYTE OF OP. |
| 0209& B7 51& | 295 | | STA | XDATAH | ;STORE IN HIGH ADDR. |
| 020B& CD 032C& | 296 | | JSR | OPFETCH | ;GET 3RD BYTE OF OP. |
| 020E& B6 45& | 297 | | LDA | OPDATA | ;LOAD IT. |
| 0210& B7 52& | 298 | | STA | XDATAL | ;STORE IN LOW ADDR. |
| 0212& B6 58& | 299 | | LDA | XREG | ;GET X PSEUDO REG. |
| 0214& BB 52& | 300 | | ADD | XDATAL | ;ADD INDEX TO ADDR. |
| 0216& B7 52& | 301 | | STA | XDATAL | ;STORE RESULT. |
| 0218& 24 02 | 302 | | BCC | OPCODHD9 | ;PASSED #0FFH? |

| | | | | | | |
|---|---|---|---|---|---|---|
| 021A& 3C 51& | 303 | | INC | XDATAH | ;YES, HIGH=HIGH+1. |
| 021C& 1D 41& | 304 | OPCODHD9 | BCLR | 6,XSW | ;SET FOR RAM |
| 021E& 1E 41& | 305 | | BSET | 7,XSW | ;DATA ACCESS. |
| 0220& CD 09A4& | 306 | | JSR | RAMWRIT | ;WRITE DATA. |
| 0223& CC 0020& | 307 | | JMP | OPLOOP | ;NEXT INSTRUCTION. |
| 0226& CD 0323& | 308 | OPCODH8 | JSR | PCTRLOD | ;POP ADDRESS FROM |
| 0229& CC 0020& | 309 | | JMP | OPLOOP | ;STACK FOR RTS OP. |
| 022C& B6 45& | 310 | OPJUMP | LDA | OPDATA | ;GET OP CODE BYTE 1. |
| 022E& A4 F0 | 311 | | AND | #0F0H | ;MASK OFF LOW HALF. |
| 0230& A0 A0 | 312 | | SUB | #0A0H | ;SET FOR 0 RELATIVE. |
| 0232& 44 | 313 | | LSRA | | ;SHIFT RIGHT 3 BITS |
| 0233& 44 | 314 | | LSRA | | ;FOR 2 BYTE OFFSET. |
| 0234& 44 | 315 | | LSRA | | ; |
| 0235& 97 | 316 | | TAX | | ;PUT A IN X. |
| 0236& DC 0239& | 317 | | JMP | OPJUMP1,X | ;INDEXED JUMP. |
| 0239& 20 0A | 318 | OPJUMP1 | BRA | OPJMPHA | ;IMMEDIATE MODE. |
| 023B& 20 08 | 319 | | BRA | OPJMPHA | ;DIRECT MODE. |
| 023D& 20 0C | 320 | | BRA | OPJMPHC | ;EXTENDED MODE. |
| 023F& 20 27 | 321 | | BRA | OPJMPHD | ;INDEXED 2 BYTE. |
| 0241& 20 02 | 322 | | BRA | OPJMPHA | ;INDEXED 1 BYTE. |
| 0243& 20 03 | 323 | | BRA | OPJMPHF | ;INDEXED 0 BYTE. |
| 0245& CD 032C& | 324 | OPJMPHA | JSR | OPFETCH | ;GET BYTE 2. |
| 0248& CC 0020& | 325 | OPJMPHF | JMP | OPLOOP | ;DO NOT EXECUTE. |
| 024B& CD 032C& | 326 | OPJMPHC | JSR | OPFETCH | ;GET 2ND BYTE OF OP. |
| 024E& B6 45& | 327 | | LDA | OPDATA | ;LOAD IT. |
| 0250& A1 10 | 328 | | CMP | #10H | ;IS OP CODE IN |
| 0252& 24 06 | 329 | | BCC | OPJMPHC1 | ;RAM AREA? |
| 0254& CD 032C& | 330 | | JSR | OPFETCH | ;NO, GET 3RD BYTE. |
| 0257& CC 0020& | 331 | | JMP | OPLOOP | ;DO NOT EXECUTE. |
| 025A& A0 10 | 332 | OPJMPHC1 | SUB | #10H | ;SET FOR RAM OFFSET. |
| 025C& B7 56& | 333 | | STA | PCTRH | ;SAVE IN HIGH ADDR. |
| 025E& CD 032C& | 334 | | JSR | OPFETCH | ;GET 3RD BYTE OF OP. |
| 0261& B6 45& | 335 | | LDA | OPDATA | ;LOAD IT. |
| 0263& B7 55& | 336 | | STA | PCTRL | ;SAVE IT IN LOW ADDR. |
| 0265& CC 0020& | 337 | | JMP | OPLOOP | ;NEXT INSTRUCTION. |
| 0268& CD 032C& | 338 | OPJMPHD | JSR | OPFETCH | ;GET 2ND BYTE OF OP. |
| 026B& B6 45& | 339 | | LDA | OPDATA | ;LOAD IT. |
| 026D& A1 10 | 340 | | CMP | #10H | ;IS IT IN THE |
| 026F& 24 06 | 341 | | BCC | OPJMPHD1 | ;RAM CHIP? |
| 0271& CD 032C& | 342 | | JSR | OPFETCH | ;NO, GET 3RD BYTE. |
| 0274& CC 0020& | 343 | | JMP | OPLOOP | ;NEXT INSTRUCTION. |
| 0277& A0 10 | 344 | OPJMPHD1 | SUB | #10H | ;SET FOR RAM OFFSET. |
| 0279& B7 56& | 345 | | STA | PCTRH | ;SAVE IN HIGH ADDR. |
| 027B& CD 032C& | 346 | | JSR | OPFETCH | ;GET 3RD BYTE OF OP. |
| 027E& B6 45& | 347 | | LDA | OPDATA | ;LOAD IT. |
| 0280& B7 55& | 348 | | STA | PCTRL | ;SAVE IN LOW ADDR. |
| 0282& B6 58& | 349 | | LDA | XREG | ;GET X PSEUDO REG. |
| 0284& BB 55& | 350 | | ADD | PCTRL | ;ADD TO LOW ADDR. |
| 0286& B7 55& | 351 | | STA | PCTRL | ;SAVE IN LOW ADDR. |
| 0288& 24 02 | 352 | | BCC | OPJMPHD2 | ;PASSED #0FFH? |
| 028A& 3C 56& | 353 | | INC | PCTRH | ;HIGH=HIGH+1. |
| 028C& CC 0020& | 354 | OPJMPHD2 | JMP | OPLOOP | ;NEXT INSTRUCTION. |
| 028F& B6 45& | 355 | OPJSR | LDA | OPDATA | ;LOAD 1ST BYTE OF OP. |
| 0291& A4 F0 | 356 | | AND | #0F0H | ;MASK OFF LOW HALF. |
| 0293& A0 A0 | 357 | | SUB | #0A0H | ;SET FOR ZERO OFFSET. |
| 0295& 44 | 358 | | LSRA | | ;SHIFT RIGHT 3 BITS |
| 0296& 44 | 359 | | LSRA | | ;FOR 2 BYTE OFFSET. |
| 0297& 44 | 360 | | LSRA | | ; |
| 0298& 97 | 361 | | TAX | | ;PUT A IN X. |
| 0299& DC 029C& | 362 | | JMP | OPJSR1,X | ;INDEXED JUMP. |
| 029C& 20 0A | 363 | OPJSR1 | BRA | OPJSRHA | ;BSR INSTRUCTION. |
| 029E& 20 08 | 364 | | BRA | OPJSRHA | ;DIRECT MODE. |
| 02A0& 20 0C | 365 | | BRA | OPJSRHC | ;EXTENDED MODE. |
| 02A2& 20 3B | 366 | | BRA | OPJSRHD | ;INDEXED 2 BYTE. |
| 02A4& 20 02 | 367 | | BRA | OPJSRHA | ;INDEXED 1 BYTE. |
| 02A6& 20 03 | 368 | | BRA | OPJSRHF | ;INDEXED 0 BYTE. |
| 02A8& CD 032C& | 369 | OPJSRHA | JSR | OPFETCH | ;GET 2ND BYTE OF OP. |
| 02AB& CC 0020& | 370 | OPJSRHF | JMP | OPLOOP | ;DO NOT EXECUTE IT. |
| 02AE& CD 032C& | 371 | OPJSRHC | JSR | OPFETCH | ;GET 2ND BYTE OF OP. |
| 02B1& B6 45& | 372 | | LDA | OPDATA | ;LOAD IT. |
| 02B3& A1 10 | 373 | | CMP | #10H | ;IS IT IN THE |
| 02B5& 24 0F | 374 | | BCC | OPJSRHC1 | ;RAM AREA? |
| 02B7& B7 5B& | 375 | | STA | XSUB2 | ;NO, SAVE IN #2. |

```
02B9& CD 032C&   376              JSR      OPFETCH  ;GET BYTE 3 OF OP.
02BC& B6 45&     377              LDA      OPDATA   ;LOAD IT.
02BE& B7 5C&     378              STA      XSUB3    ;SAVE IT IN #3.
02C0& CD 033E&   379              JSR      OPEXEC   ;EXECUTE IT.
02C3& CC 0020&   380              JMP      OPLOOP   ;NEXT INSTRUCTION.
02C6& A0 10      381  OPJSRHC1    SUB      #10H     ;SET FOR 0 OFFSET.
02C8& B7 5B&     382              STA      XSUB2    ;STORE IN BYTE #2.
02CA& CD 032C&   383              JSR      OPFETCH  ;GET BYTE 3 OF OP.
02CD& B6 45&     384              LDA      OPDATA   ;LOAD IT.
02CF& B7 5C&     385              STA      XSUB3    ;STORE IN BYTE #3.
02D1& CD 031A&   386              JSR      PCTRSAV  ;SAVE PSEUDO REGS.
02D4& B6 5B&     387              LDA      XSUB2    ;GET HIGH ADDRESS.
02D6& B7 56&     388              STA      PCTRH    ;SAVE IN PGM PTR.
02D8& B6 5C&     389              LDA      XSUB3    ;GET LOW ADDRESS.
02DA& B7 55&     390              STA      PCTRL    ;SAVE IN PGM PTR.
02DC& CC 0020&   391              JMP      OPLOOP   ;NEXT INSTRUCTION.
02DF& CD 032C&   392  OPJSRHD     JSR      OPFETCH  ;GET 2ND BYTE OF OP.
02E2& B6 45&     393              LDA      OPDATA   ;LOAD IT.
02E4& A1 10      394              CMP      #10H     ;IS IT IN THE
02E6& 24 0F      395              BCC      OPJSRHD1 ;RAM CHIP?
02E8& B7 5B&     396              STA      XSUB2    ;NO, SAVE LOW ADDR.
02EA& CD 032C&   397              JSR      OPFETCH  ;GET BYTE 3 OF OP.
02ED& B6 45&     398              LDA      OPDATA   ;LOAD IT.
02EF& B7 5C&     399              STA      XSUB3    ;SAVE IT IN #3.
02F1& CD 033E&   400              JSR      OPEXEC   ;EXECUTE IT.
02F4& CC 0020&   401              JMP      OPLOOP   ;NEXT INSTRUCTION.
02F7& A0 10      402  OPJSRHD1    SUB      #10H     ;SET FOR 0 OFFSET.
02F9& B7 5B&     403              STA      XSUB2    ;SAVE IN BYTE #2.
02FB& CD 032C&   404              JSR      OPFETCH  ;GET BYTE 3 OF OP.
02FE& B6 45&     405              LDA      OPDATA   ;LOAD IT.
0300& B7 5C&     406              STA      XSUB3    ;SAVE IT IN #3.
0302& CD 031A&   407              JSR      PCTRSAV  ;SAVE PSEUDO REGS.
0305& B6 5B&     408              LDA      XSUB2    ;GET HIGH ADDR.
0307& B7 56&     409              STA      PCTRH    ;SAVE TO PGM PTR.
0309& B6 5C&     410              LDA      XSUB3    ;GET LOW ADDR.
030B& B7 55&     411              STA      PCTRL    ;SAVE TO PGM PTR.
030D& B6 58&     412              LDA      XREG     ;LOAD X PSEUDO REG.
030F& BB 55&     413              ADD      PCTRL    ;ADD TO LOW ADDR.
0311& B7 55&     414              STA      PCTRL    ;SAVE TO LOW PGM PTR.
0313& 24 02      415              BCC      OPJSRHD2 ;PASSED #0FFH?
0315& 3C 56&     416              INC      PCTRH    ;YES, HIGH=HIGH+1.
0317& CC 0020&   417  OPJSRHD2    JMP      OPLOOP   ;NEXT INSTRUCTION.
                 418       SEJ
                 419  ;************* PCTRSAV    *********************
                 420  ;************* PCTRLOD    *********************
                 421  ;*********************************************
                 422  ;
                 423  ;THESE SUBROUTINES SAVE AND LOAD THE PSEUDO
                 424  ;PROGRAM COUNTER IN THE RAM STACK.
                 425  ;
                 426  ;*********************************************
                 427  ;
                 428  ;    INPUT :
                 429  ;            PCTRL
                 430  ;            PCTRH
                 431  ;
                 432  ;    OUTPUT :
                 433  ;            PCTRL
                 434  ;            PCTRH
                 435  ;
                 436  ;    REGISTERS SAVED (Y/N) : N
                 437  ;    IF "N" ABOVE THEN REGISTERS USED
                 438  ;            (* = MODIFIED):
                 439  ;                    *X REGISTER
                 440  ;
                 441  ;    FIELDS USED (* = MODIFIED):
                 442  ;                    *PCTRL
                 443  ;                    *PCTRH
                 444  ;
                 445  ;    SUBROUTINES CALLED:
                 446  ;                    STKPUSH
                 447  ;                    STKPOP
                 448  ;
```

```
031A&  BE 55&       449   ;************************************
                    450   PCTRSAV  LDX     PCTRL    ;LOAD LOW PGM PTR.
031C&  BD E7&       451            JSR     STKPUSH  ;PUSH IT ON STACK.
031E&  BE 56&       452            LDX     PCTRH    ;LOAD HIGH PGM PTR.
0320&  BD E7&       453            JSR     STKPUSH  ;PUSH IT ON STACK.
0322&  81           454            RTS              ;
0323&  BD D3&       455   PCTRLOD  JSR     STKPOP   ;POP STACK.
0325&  BF 56&       456            STX     PCTRH    ;STORE TO HIGH PTR.
0327&  BD D3&       457            JSR     STKPOP   ;POP STACK.
0329&  BF 55&       458            STX     PCTRL    ;STORE TO LOW PTR.
032B&  81           459            RTS              ;
                    460   $EJ
                    461   ;************* OPFETCH  *******************
                    462   ;******************************************
                    463   ;
                    464   ;THIS SUBROUTINE GETS THE NEXT PSEUDO
                    465   ;INSTRUCTION FROM THE RAM CHIP USING
                    466   ;THE PROGRAM COUTER IN MEMORY AS A
                    467   ;POINTER.
                    468   ;
                    469   ;******************************************
                    470   ;
                    471   ;   INPUT :
                    472   ;           PCTRL  (ADDRESS OF NEXT OP CODE
                    473   ;           PCTRH   IN RAM CHIP)
                    474   ;
                    475   ;   OUTPUT :
                    476   ;           OPDATA OP CODE FROM RAM
                    477   ;           PCTRL  (INCREMENTED TO POINT TO
                    478   ;           PCTRH   NEXT OP CODE)
                    479   ;
                    480   ;   REGISTERS SAVED (Y/N) : Y
                    481   ;   IF "N" ABOVE THEN REGISTERS USED
                    482   ;           (* = MODIFIED):
                    483   ;
                    484   ;   FIELDS USED (* = MODIFIED):
                    485   ;           *PCTRL
                    486   ;           *PCTRH
                    487   ;           *XSW      /BIT:6,7
                    488   ;
                    489   ;   SUBROUTINES CALLED:
                    490   ;           REGSAVE
                    491   ;           REGLOAD
                    492   ;           RAMREAD
                    493   ;
                    494   ;******************************************
032C&  BD 94&       495   OPFETCH  JSR     REGSAVE  ;SAVE X & A REGS.
032E&  1C 41&       496            BSET    6,XSW    ;SET FOR OP CODE
0330&  1F 41&       497            BCLR    7,XSW    ;RAM ACCESS.
0332&  CD 09CA&     498            JSR     RAMREAD  ;READ RAM CHIP.
0335&  3C 55&       499            INC     PCTRL    ;LOW=LOW+1.
0337&  26 02        500            BNE     OPFETCH1 ;LOW ADDR = 0?
0339&  3C 56&       501            INC     PCTRH    ;YES, HIGH=HIGH+1.
033B&  BD A3&       502   OPFETCH1 JSR     REGLOAD  ;LOAD X & A REGS.
033D&  81           503            RTS              ;
                    504   $EJ
                    505   ;************* OPEXEC   *******************
                    506   ;******************************************
                    507   ;
                    508   ;THIS SUBROUTINE WILL EXECUTEC A SINGLE
                    509   ;INSTRUCTION FROM THE MPU MEMORY IN LOW RAM.
                    510   ;
                    511   ;******************************************
                    512   ;
                    513   ;   INPUT :
                    514   ;           XSUB1-3   CONTAINS THE OPCODE TO BE
                    515   ;                     EXECUTED.
                    516   ;           AREG      A PSEUDO REGISTER
                    517   ;           XREG      X PSEUDO REGISTER
                    518   ;           CCR       CONDITION CODE REGISTER
                    519   ;
                    520   ;   OUTPUT :
                    521   ;           AREG      A PSEUDO REGISTER
```

```
                        522    ;        XREG      X PSEUDO REGISTER
                        523    ;        CCR       CONDITION CODE REGISTER
                        524    ;
                        525    ; REGISTERS SAVED (Y/N) : Y
                        526    ; IF "N" ABOVE THEN REGISTERS USED
                        527    ;              (* = MODIFIED):
                        528    ;
                        529    ; FIELDS USED (* = MODIFIED):
                        530    ;              *AREG
                        531    ;              *XREG
                        532    ;              *CCR
                        533    ;              *XSW      /BIT:6,7
                        534    ;
                        535    ; SUBROUTINES CALLED:
                        536    ;              REGSAVE
                        537    ;              REGLOAD
                        538    ;              XSUB1     (OP CODE IN MEMORY)
                        539    ;
                        540    ;***********************************************
033E&  BD 94&           541    OPEXEC   JSR      REGSAVE ;SAVE X & A REGS.
0340&  1D 41&           542             BCLR     6,XSW    ;SET UP FOR PROGRAM
0342&  1F 41&           543             BCLR     7,XSW    ;RAM DATA ACCESS.
0344&  09 59& 06        544             BRCLR    4,CCR,OPEXECA;HALF CARRY?
0347&  A6 0F            545             LDA      #0FH     ;YES, SET HALF
0349&  AB 01            546             ADD      #1       ;CARRY BIT.
034B&  20 04            547             BRA      OPEXECB  ;BRANCH AROUND.
034D&  A6 00            548    OPEXECA  LDA      #0       ;NO, CLEAR HALF
034F&  AB 00            549             ADD      #0       ;CARRY BIT.
0351&  07 59& 03        550    OPEXECB  BRCLR    3,CCR,OPEXECC;INT BIT SET?
0354&  9B               551             SEI               ;YES, SET INT BIT.
0355&  20 01            552             BRA      OPEXECD  ;BRANCH AROUND.
0357&  9A               553    OPEXECC  CLI               ;NO, CLEAR INT BIT.
0358&  B6 59&           554    OPEXECD  LDA      CCR      ;LOAD PSEUDO CCR.
035A&  44               555             LSRA              ;SHIFT RIGHT 1 BIT.
035B&  A4 03            556             AND      #03      ;GET ONLY N & Z BITS.
035D&  48               557             LSLA              ;FOR 2 BYTE OFFSET.
035E&  97               558             TAX               ;PUT A IN X.
035F&  B6 57&           559             LDA      AREG     ;LOAD A PSEUDO REG.
0361&  DC 0364&         560             JMP      OPEXECE,X;INDEXED JUMP.
0364&  20 04            561    OPEXECE  BRA      OPEXECE0;N & Z BOTH ZERO.
0366&  20 0C            562             BRA      OPEXECE1;N=0, Z=1.
0368&  20 10            563             BRA      OPEXECE2;N=1, Z=0.
036A&  AE FE            564    OPEXECE0 LDX      #0FEH    ;SET REGSAV FIELD
036C&  BF 3E&           565             STX      REGSAV   ;TO #0FFH.
036E&  BE 58&           566             LDX      XREG     ;LOAD X PSEUDO REG.
0370&  33 3E&           567             COM      REGSAV   ;REGSAV = #01H
0372&  20 0E            568             BRA      OPEXECF  ;EXECUTE OP CODE.
0374&  BE 58&           569    OPEXECE1 LDX      XREG     ;LOAD X PSEUDO REG.
0376&  B3 58&           570             CPX      XREG     ;COMPARE WITH ITSELF.
0378&  20 08            571             BRA      OPEXECF  ;EXECUTE OP CODE.
037A&  AE 7E            572    OPEXECE2 LDX      #07EH    ;SET REGSAV FIELD
037C&  BF 3E&           573             STX      REGSAV   ;TO #07EH.
037E&  BE 58&           574             LDX      XREG     ;LOAD X PSEUDO REG.
0380&  33 3E&           575             COM      REGSAV   ;REGSAV = #081H (-1).
0382&  01 59& 00        576    OPEXECF  BRCLR    0,CCR,OPEXECG;SET CARRY FLAG.
0385&  BD 5A&           577    OPEXECG  JSR      XSUB1    ;EXECUTE OP CODE.
0387&  24 04            578             BCC      OPEXEC1  ;CARRY FLAG CLEAR?
0389&  10 59&           579             BSET     0,CCR    ;NO, SET CCR CARRY.
038B&  20 02            580             BRA      OPEXEC2  ;BRANCH AROUND.
038D&  11 59&           581    OPEXEC1  BCLR     0,CCR    ;YES, CLEAR CARRY.
038F&  26 04            582    OPEXEC2  BNE      OPEXEC3  ;Z FLAG CLEAR?
0391&  12 59&           583             BSET     1,CCR    ;NO, SET CCR Z FLAG.
0393&  20 02            584             BRA      OPEXEC4  ;BRANCH AROUND.
0395&  13 59&           585    OPEXEC3  BCLR     1,CCR    ;YES, CLEAR Z FLAG.
0397&  2A 04            586    OPEXEC4  BPL      OPEXEC5  ;N FLAG CLEAR?
0399&  14 59&           587             BSET     2,CCR    ;NO, SET CCR N FLAG.
039B&  20 02            588             BRA      OPEXEC6  ;BRANCH AROUND.
039D&  15 59&           589    OPEXEC5  BCLR     2,CCR    ;YES, CLEAR N FLAG.
039F&  2C 04            590    OPEXEC6  BMC      OPEXEC7  ;I FLAG CLEAR?
03A1&  16 59&           591             BSET     3,CCR    ;NO, SET CCR I FLAG.
03A3&  20 02            592             BRA      OPEXEC8  ;BRANCH AROUND.
03A5&  17 59&           593    OPEXEC7  BCLR     3,CCR    ;YES, CLEAR I FLAG.
03A7&  28 04            594    OPEXEC8  BHCC     OPEXEC9  ;H FLAG CLEAR?
```

| | | | | | |
|---|---|---|---|---|---|
| 03A9& 18 59& | 595 | | BSET | 4,CCR | ;NO, SET CCR H FLAG. |
| 03AB& 20 02 | 596 | | BRA | OPEXEC10 | ;BRANCH AROUND. |
| 03AD& 19 59& | 597 | OPEXEC9 | BCLR | 4,CCR | ;YES, CLEAR H FLAG. |
| 03AF& B7 57& | 598 | OPEXEC10 | STA | AREG | ;SAVE A PSEUDO REG. |
| 03B1& BF 58& | 599 | | STX | XREG | ;SAVE X PSEUDO REG. |
| 03B3& BD A3& | 600 | | JSR | REGLOAD | ;LOAD X & A REGS. |
| 03B5& 81 | 601 | | RTS | | ; |

```
        602         $EJ
          2         ;************ LCDLOAD  ********************
          3         ;******************************************
          4         ;
          5         ;THIS SUBROUTINE WILL LOAD THE ASSEMBLER
          6         ;INSTRUCTION FROM RAM TO PERFORM THE TURNING
          7         ;ON OR OFF OF A CERTAIN SEGMENT.
          8         ;
          9         ;******************************************
         10         ;
         11         ;   INPUT :
         12         ;         X REGISTER CONTAINS THE NUMBER OF THE
         13         ;         RELATIVE ADDRESS IN THE RAM WHERE
         14         ;         THE OP CODE IS LOCATED (0-155).
         15         ;
         16         ;   OUTPUT : (NONE)
         17         ;
         18         ;   REGISTERS SAVED (Y/N) : N
         19         ;   IF "N" ABOVE THEN REGISTERS USED
         20         ;         (*, = MODIFIED):
         21         ;                 X REGISTER
         22         ;
         23         ;   FIELDS USED (* = MODIFIED):
         24         ;                 *LCDSAV
         25         ;                 *XSUB1
         26         ;                 *XSUB2
         27         ;                 *XSUB3
         28         ;                 *XDATAL
         29         ;                 *XDATAH
         30         ;                 *XDATA
         31         ;                 *XSW     /BIT:6,7
         32         ;
         33         ;   SUBROUTINES CALLED:
         34         ;                 STKPUSH
         35         ;                 STKPOP
         36         ;                 RAMREAD
         37         ;                 XSUB1
         38         ;
         39         ;******************************************
```

| | | | | | |
|---|---|---|---|---|---|
| 03BA& 58 | 40 | LCDLOAD | LSLX | | ;X = X*2 (RAM ADDR). |
| 03BB& BF 50& | 41 | | STX | LCDSAV | ;SAVE IT IN LCDSAV. |
| 03BD& BE 5A& | 42 | | LDX | XSUB1 | ;PUT CONTENTS |
| 03BF& BD E7& | 43 | | JSR | STKPUSH | ;OF XSUB1,2,3 |
| 03C1& BE 5B& | 44 | | LDX | XSUB2 | ;INTO RAM STACK. |
| 03C3& BD E7& | 45 | | JSR | STKPUSH | ; |
| 03C5& BE 5C& | 46 | | LDX | XSUB3 | ; |
| 03C7& BD E7& | 47 | | JSR | STKPUSH | ; |
| 03C9& BE 50& | 48 | | LDX | LCDSAV | ;RESTORE RAM ADDR. |
| 03CB& BF 52& | 49 | | STX | XDATAL | ;SET UP |
| 03CD& 3F 51& | 50 | | CLR | XDATAH | ;RAM ADDRESS. |
| 03CF& 1D 41& | 51 | | BCLR | 6,XSW | ;TYPE 2 RAM I/O. |
| 03D1& 1E 41& | 52 | | BSET | 7,XSW | ; |
| 03D3& CD 09CA& | 53 | | JSR | RAMREAD | ;READ RAM. |
| 03D6& BE 46& | 54 | | LDX | XDATA | ;OP CODE BYTE #1. |
| 03D8& BF 5A& | 55 | | STX | XSUB1 | ; |
| 03DA& 3C 52& | 56 | | INC | XDATAL | ;GET NEXT BYTE |
| 03DC& CD 09CA& | 57 | | JSR | RAMREAD | ;IN RAM. |
| 03DF& BE 46& | 58 | | LDX | XDATA | ;OP CODE BYTE #2. |
| 03E1& BF 5B& | 59 | | STX | XSUB2 | ; |
| 03E3& AE 81 | 60 | | LDX | #81H | ;OP CODE FOR RTS |
| 03E5& BF 5C& | 61 | | STX | XSUB3 | ;INSTRUCTION. |
| 03E7& BD 5A& | 62 | | JSR | XSUB1 | ;EXECUTE IT. |
| 03E9& BD D3& | 63 | | JSR | STKPOP | ;RESTORE |
| 03EB& BF 5C& | 64 | | STX | XSUB3 | ;XSUB1,2,3 |
| 03ED& BD D3& | 65 | | JSR | STKPOP | ; |
| 03EF& BF 5B& | 66 | | STX | XSUB2 | ; |

```
03F1& BD D3&         67              JSR     STKPOP      ;
03F3& BF 5A&         68              STX     XSUB1       ;
03F5& 81             69              RTS                 ;
                     70      $EJ
                     71      ;************** LCDTIME    *********************
                     72      ;************** LCDAM      *********************
                     73      ;************** LCDPM      *********************
                     74      ;************** LCDDATE    *********************
                     75      ;************** LCDLAST    *********************
                     76      ;************** LCDTEST    *********************
                     77      ;************** LCDLEFT    *********************
                     78      ;************** LCDMGDL    *********************
                     79      ;***********************************************
                     80      ;
                     81      ;THESE SUBROUTINES TURN THE APPROPRIATE
                     82      ;ANNUNCIATORS ON OR OFF ON THE LCD.
                     83      ;
                     84      ;***********************************************
                     85      ;
                     86      ;    INPUT :
                     87      ;           X REGISTER CONTAINS THE BIT (0-7) OF
                     88      ;           THE ANNUCIATOR TO TURN ON OR OFF.
                     89      ;           A REGISTER CONTAINS 1 IF TURN ON AND
                     90      ;           0 IF TURN OFF.
                     91      ;
                     92      ;    OUTPUT : (NONE)
                     93      ;
                     94      ;    REGISTERS SAVED (Y/N) : Y
                     95      ;    IF "N" ABOVE THEN REGISTERS USED
                     96      ;           (* = MODIFIED):
                     97      ;
                     98      ;    FIELDS USED (* = MODIFIED):
                     99      ;
                    100      ;    SUBROUTINES CALLED:
                    101      ;           (JUMPS TO LCDSYM)
                    102      ;
                    103      ;***********************************************
03F6& BD 94&        104      LCDTIME   JSR    REGSAVE
03F8& AE 01         105                LDX    #1
03FA& CC 04A7&      106                JMP    LCDSYM
03FD& BD 94&        107      LCDAM     JSR    REGSAVE
03FF& AE 02         108                LDX    #2
0401& CC 04A7&      109                JMP    LCDSYM
0404& BD 94&        110      LCDPM     JSR    REGSAVE
0406& AE 04         111                LDX    #4
0408& CC 04A7&      112                JMP    LCDSYM
040B& BD 94&        113      LCDDATE   JSR    REGSAVE
040D& AE 08         114                LDX    #8
040F& CC 04A7&      115                JMP    LCDSYM
0412& BD 94&        116      LCDLAST   JSR    REGSAVE
0414& AE 10         117                LDX    #16
0416& CC 04A7&      118                JMP    LCDSYM
0419& BD 94&        119      LCDTEST   JSR    REGSAVE
041B& AE 20         120                LDX    #32
041D& CC 04A7&      121                JMP    LCDSYM
0420& BD 94&        122      LCDLEFT   JSR    REGSAVE
0422& AE 40         123                LDX    #64
0424& CC 04A7&      124                JMP    LCDSYM
0427& BD 94&        125      LCDMGDL   JSR    REGSAVE
0429& AE 80         126                LDX    #128
042B& CC 04A7&      127                JMP    LCDSYM
                    128      $EJ
                    129      ;************** LCDCLR     *********************
                    130      ;************** LCDSET     *********************
                    131      ;***********************************************
                    132      ;
                    133      ;THESE SUBROUTINES CLEAR THE LCD DISPLAY OR
                    134      ;TURN ON ALL SEGMENTS OF THE LCD.
                    135      ;
                    136      ;***********************************************
                    137      ;
                    138      ;    INPUT : (NONE)
                    139      ;
```

```
                    140      ;  OUTPUT : (NONE)
                    141      ;
                    142      ;  REGISTERS SAVED (Y/N) : Y
                    143      ;  IF "N" ABOVE THEN REGISTERS USED
                    144      ;          (* = MODIFIED):
                    145      ;
                    146      ;  FIELDS USED (* = MODIFIED):
                    147      ;          LCD1-8 (INDEX REG. TO ACCESS)
                    148      ;
                    149      ;  SUBROUTINES CALLED:
                    150      ;          REGSAVE
                    151      ;          (JUMPS TO LCDEND)
                    152      ;
                    153      ;********************************************
042E& BD 94&        154      LCDCLR   JSR     REGSAVE   ;SAVE X & A REGS.
0430& A6 00         155               LDA     #0        ;TURN OFF ALL SEGS.
0432& AE 00         156               LDX     #0        ;INDEX TO LCD REGS.
0434& E7 21&        157      LCDCLR1  STA     LCD1,X    ;STORE TO LCD REG.
0436& 5C            158               INCX              ;INDEX = INDEX+1.
0437& A3 07         159               CPX     #7        ;ALL 8 DONE?
0439& 23 F9         160               BLS     LCDCLR1   ;IF NO, NEXT REG.
043B& CC 0530&      161               JMP     LCDEND    ;YES, GO TO LCDEND.
043E& BD 94&        162      LCDSET   JSR     REGSAVE   ;SAVE X & A REGS.
0440& A6 FF         163               LDA     #0FFH     ;TURN ON ALL SEGS.
0442& AE 00         164               LDX     #0        ;INDEX TO LCD REGS.
0444& E7 21&        165      LCDSET1  STA     LCD1,X    ;STORE TO LCD REG.
0446& 5C            166               INCX              ;INDEX = INDEX+1.
0447& A3 07         167               CPX     #7        ;ALL 8 DONE?
0449& 23 F9         168               BLS     LCDSET1   ;IF NO, NEXT REG.
044B& CC 0530&      169      LCDENDH  JMP     LCDEND    ;YES, GO TO LCDEND.
                    170      $EJ
                    171      ;************ LCDPRT   *********************
                    172      ;********************************************
                    173      ;
                    174      ;THIS SUBROUTINE WILL WRITE ANY COMBINATION
                    175      ;OF 7 SEGMENTS TO ANY OF 4 DIGITS ON THE LCD.
                    176      ;
                    177      ;********************************************
                    178      ;
                    179      ;  INPUT :
                    180      ;          A REGISTER IS THE DIGIT # (0-3) TO
                    181      ;          BE WRITTEN TO.
                    182      ;          X REGISTER IS THE 7 SEGMENT BIT
                    183      ;          COMBINATION TO WRITE.
                    184      ;
                    185      ;  OUTPUT : (NONE)
                    186      ;
                    187      ;  REGISTERS SAVED (Y/N) : Y
                    188      ;  IF "N" ABOVE THEN REGISTERS USED
                    189      ;          (* = MODIFIED):
                    190      ;
                    191      ;  FIELDS USED (* = MODIFIED):
                    192      ;          *SEGLOG
                    193      ;          *SEGVAL
                    194      ;          LCDTABL
                    195      ;
                    196      ;  SUBROUTINES CALLED:
                    197      ;          REGSAVE
                    198      ;          (JUMPS TO LCDNUM)
                    199      ;
                    200      ;********************************************
044E& BD 94&        201      LCDPRT   JSR     REGSAVE   ;SAVE X & A REGS.
0450& B7 2A&        202               STA     SEGLOC    ;STORE DISPLAY POS.
0452& A3 80         203               CPX     #128      ;IS BIT7 OF DATA
0454& 25 05         204               BCS     LCDPRTA   ;HIGH?
0456& 9F            205               TXA               ;YES, X >>> A.
0457& A4 7F         206               AND     #7FH      ;CLEAR BIT7.
0459& 20 02         207               BRA     LCDPRTB   ;BRANCH AROUND.
045B& E6 80&        208      LCDPRTA  LDA     LCDTABL,X ;NO, LOAD ROM CHAR.
045D& B7 29&        209      LCDPRTB  STA     SEGVAL    ;STORE DATA.
045F& B6 2A&        210               LDA     SEGLOC    ;GET DISPLAY POS.
0461& AE 01         211               LDX     #1        ;CONVERT BINARY TO
0463& BF 2A&        212               STX     SEGLOC    ;SET BIT POSITION.
```

```
0465& A1 00           213          LCDPRT1  CMP      #0          ;IE. 00 = BIT0 SET.
0467& 27 05           214                   BEQ      LCDPRT2     ;    01 = BIT1 SET.
0469& 38 2A&          215                   ASL      SEGLOC      ;NOT 0, SHIFT LEFT.
046B& 4A              216                   DECA                 ;POS. = POS.  - 1.
046C& 20 F7           217                   BRA      LCDPRT1     ;GO AROUND AGAIN.
046E& CC 0547&        218          LCDPRT2  JMP      LCDNUM      ;OK, GO DO IT.
                      219          $EJ
                      220          ;************ LCDW   *********************
                      221          ;************ LCDI   *********************
                      222          ;*********************************************
                      223          ;
                      224          ;THESE SUBROUTINES TURN ON AND OFF THE SPECIAL
                      225          ;ANNUCIATORS USED TO FORM THE "W" AND THE "I"
                      226          ;IN THE WORD "WIPE".
                      227          ;
                      228          ;*********************************************
                      229          ;
                      230          ;   INPUT :
                      231          ;           A REGISTER IS NON-ZERO IF THE ANNUN-
                      232          ;           CIATOR IS TO BE TURNED ON AND ZERO
                      233          ;           IF IT IS TO BE TURNED OFF.
                      234          ;
                      235          ;   OUTPUT : (NONE)
                      236          ;
                      237          ;   REGISTERS SAVED (Y/N) : Y
                      238          ;   IF "N" ABOVE THEN REGISTERS USED
                      239          ;           (* = MODIFIED):
                      240          ;
                      241          ;   FIELDS USED (* = MODIFIED):
                      242          ;
                      243          ;   SUBROUTINES CALLED:
                      244          ;              REGSAVE
                      245          ;              LCDLOAD
                      246          ;           (JUMPS TO LCDEND)
                      247          ;
                      248          ;*********************************************
0471& BD 94&          249          LCDW     JSR      REGSAVE     ;SAVE X & A REGS.
0473& A1 00           250                   CMP      #0          ;TURN ON?
0475& 26 08           251                   BNE      LCDWON      ;
0477& AE 00           252                   LDX      #0          ;NO, LOAD RAM OFFSET.
0479& CD 03BA&        253                   JSR      LCDLOAD     ;EXECUTE IT.
047C& CC 0530&        254                   JMP      LCDEND      ;REFRESH DISPLAY.
047F& AE 01           255          LCDWON   LDX      #1          ;YES, LOAD OFFSET.
0481& CD 03BA&        256                   JSR      LCDLOAD     ;EXECUTE IT.
0484& CC 0530&        257                   JMP      LCDEND      ;REFRESH DISPLAY.
0487& BD 94&          258          LCDI     JSR      REGSAVE     ;SAVE X & A REGS.
0489& A1 00           259                   CMP      #0          ;TURN ON?
048B& 26 0D           260                   BNE      LCDION      ;
048D& AE 02           261                   LDX      #2          ;NO, LOAD RAM OFFSET.
048F& CD 03BA&        262                   JSR      LCDLOAD     ;EXECUTE IT.
0492& AE 03           263                   LDX      #3          ;"I" IS SPLIT INTO
0494& CD 03BA&        264                   JSR      LCDLOAD     ;TWO SEPERATE SEGS.
0497& CC 0530&        265                   JMP      LCDEND      ;REFRESH DISPLAY.
049A& AE 04           266          LCDION   LDX      #4          ;YES, LOAD OFFSET.
049C& CD 03BA&        267                   JSR      LCDLOAD     ;EXECUTE IT.
049F& AE 05           268                   LDX      #5          ;"I" IS SPLIT INTO
04A1& CD 03BA&        269                   JSR      LCDLOAD     ;TWO SEPERATE SEGS.
04A4& CC 0530&        270                   JMP      LCDEND      ;REFRESH DISPLAY.
                      271          $EJ
                      272          ;************ LCDSYM  *********************
                      273          ;*********************************************
                      274          ;
                      275          ;THIS SUBROUTINE USES THE POWERFUL BIT
                      276          ;INSTRUCTIONS IN THE 6805 TO TURN THE
                      277          ;ANNUCIATORS ON AND OFF.
                      278          ;
                      279          ;*********************************************
                      280          ;
                      281          ;   INPUT :
                      282          ;           A REGISTER IS NON-ZERO IF THE ANNUN-
                      283          ;           CIATOR IS TO BE TURNED ON AND ZERO
                      284          ;           IF IT IS TO BE TURNED OFF.
                      285          ;           X REGISTER HAS THE DATA OF WHICH
```

```
                            286    ;            ONLY ONE BIT IS TURNED ON (=1) TO
                            287    ;            INDICATE WHICH ANNUNCIATOR.
                            288    ;
                            289    ; OUTPUT : (NONE)
                            290    ;
                            291    ; REGISTERS SAVED (Y/N) : N
                            292    ; IF "N" ABOVE THEN REGISTERS USED
                            293    ;            (* = MODIFIED):
                            294    ;               A REGISTER
                            295    ;              *X REGISTER
                            296    ;
                            297    ; FIELDS USED (* = MODIFIED):
                            298    ;              *SEGVAL
                            299    ;
                            300    ; SUBROUTINES CALLED:
                            301    ;              LCDLOAD
                            302    ;              (JUMPS TO LCDEND)
                            303    ;
                            304    ;*******************************************
04A7& BF 29&                305    LCDSYM.  STX    SEGVAL  ;STORE SEGMENT DATA.
04A9& A1 00                 306             CMP    #0      ;IF A NOT = 0 THEN
04AB& 26 43                 307             BNE    SYMON   ;TURN ON.
04AD& 01 29& 05             308             BRCLR  0,SEGVAL,SYMOFF1;BIT0 ON?
04B0& AE 06                 309             LDX    #6      ;YES, LOAD RAM
04B2& CD 03BA&              310             JSR    LCDLOAD ;OFFSET AND GO DO IT.
04B5& 03 29& 05             311    SYMOFF1  BRCLR  1,SEGVAL,SYMOFF2;BIT1 ON?
04B8& AE 07                 312             LDX    #7      ;YES, LOAD RAM
04BA& CD 03BA&              313             JSR    LCDLOAD ;OFFSET AND GO DO IT.
04BD& 05 29& 05             314    SYMOFF2  BRCLR  2,SEGVAL,SYMOFF3;BIT2 ON?
04C0& AE 08                 315             LDX    #8      ;YES, LOAD RAM
04C2& CD 03BA&              316             JSR    LCDLOAD ;OFFSET AND GO DO IT.
04C5& 07 29& 05             317    SYMOFF3  BRCLR  3,SEGVAL,SYMOFF4;BIT3 ON?
04C8& AE 09                 318             LDX    #9      ;YES, LOAD RAM
04CA& CD 03BA&              319             JSR    LCDLOAD ;AND GO DO IT.
04CD& 09 29& 05             320    SYMOFF4  BRCLR  4,SEGVAL,SYMOFF5;BIT4 ON?
04D0& AE 0A                 321             LDX    #10     ;YES, LOAD RAM
04D2& CD 03BA&              322             JSR    LCDLOAD ;AND GO DO IT.
04D5& 0B 29& 05             323    SYMOFF5  BRCLR  5,SEGVAL,SYMOFF6;BIT5 ON?
04D8& AE 0B                 324             LDX    #11     ;YES, LOAD RAM
04DA& CD 03BA&              325             JSR    LCDLOAD ;AND GO DO IT.
04DD& 0D 29& 05             326    SYMOFF6  BRCLR  6,SEGVAL,SYMOFF7;BIT6 ON?
04E0& AE 0C                 327             LDX    #12     ;YES, LOAD RAM
04E2& CD 03BA&              328             JSR    LCDLOAD ;AND GO DO IT.
04E5& 0F 29& 48             329    SYMOFF7  BRCLR  7,SEGVAL,LCDEND ;BIT7 ON?
04E8& AE 0D                 330             LDX    #13     ;YES, LOAD RAM
04EA& CD 03BA&              331             JSR    LCDLOAD ;AND GO DO IT.
04ED& CC 0530&              332             JMP    LCDEND  ;REFRESH DISPLAY.
04F0& 01 29& 05             333    SYMON    BRCLR  0,SEGVAL,SYMON1 ;BIT0 ON?
04F3& AE 0E                 334             LDX    #14     ;YES, LOAD RAM
04F5& CD 03BA&              335             JSR    LCDLOAD ;AND GO DO IT.
04F8& 03 29& 05             336    SYMON1   BRCLR  1,SEGVAL,SYMON2 ;BIT1 ON?
04FB& AE 0F                 337             LDX    #15     ;YES, LOAD RAM
04FD& CD 03BA&              338             JSR    LCDLOAD ;AND GO DO IT.
0500& 05 29& 05             339    SYMON2   BRCLR  2,SEGVAL,SYMON3 ;BIT2 ON?
0503& AE 10                 340             LDX    #16     ;YES, LOAD RAM
0505& CD 03BA&              341             JSR    LCDLOAD ;AND GO DO IT.
0508& 07 29& 05             342    SYMON3   BRCLR  3,SEGVAL,SYMON4 ;BIT3 ON?
050B& AE 11                 343             LDX    #17     ;YES, LOAD RAM
050D& CD 03BA&              344             JSR    LCDLOAD ;AND GO DO IT.
0510& 09 29& 05             345    SYMON4   BRCLR  4,SEGVAL,SYMON5 ;BIT4 ON?
0513& AE 12                 346             LDX    #18     ;YES, LOAD RAM
0515& CD 03BA&              347             JSR    LCDLOAD ;AND GO DO IT.
0518& 0B 29& 05             348    SYMON5   BRCLR  5,SEGVAL,SYMON6 ;BIT5 ON?
051B& AE 13                 349             LDX    #19     ;YES, LOAD RAM
051D& CD 03BA&              350             JSR    LCDLOAD ;AND GO DO IT.
0520& 0D 29& 05             351    SYMON6   BRCLR  6,SEGVAL,SYMON7 ;BIT6 ON?
0523& AE 14                 352             LDX    #20     ;YES, LOAD RAM
0525& CD 03BA&              353             JSR    LCDLOAD ;AND GO DO IT.
0528& 0F 29& 05             354    SYMON7   BRCLR  7,SEGVAL,LCDEND ;BIT7 ON?
052B& AE 15                 355             LDX    #21     ;YES, LOAD RAM
052D& CD 03BA&              356             JSR    LCDLOAD ;AND GO DO IT.
                            357    $EJ
                            358    ;************* LCDEND    *********************
                            359    ;*********************************************
```

```
                360  ;
                361  ;THIS SUBROUTINE REFRESHES THE LCD DISPLAY
                362  ;BY COPYING THE RAM LCD REGISTERS TO THE
                363  ;ACTUAL MPU LCD REGISTERS WHICH ARE WRITE
                364  ;ONLY AND THEREFORE CANNOT BE USED BY THE
                365  ;BIT MANIPUKATION INSTRUCTIONS.
                366  ;
                367  ;*********************************************
                368  ;
                369  ;   INPUT : (NONE)
                370  ;
                371  ;   OUTPUT : (NONE)
                372  ;
                373  ;   REGISTERS SAVED (Y/N) : N
                374  ;   IF "N" ABOVE THEN REGISTERS USED
                375  ;               (* = MODIFIED):
                376  ;                   *A REGISTER
                377  ;                   *X REGISTER
                378  ;
                379  ;   FIELDS USED (* = MODIFIED):
                380  ;                   *LCD1-8    (INDEX REG USED)
                381  ;                   *PLCD1-8   (INDEX REG USED)
                382  ;
                383  ;   SUBROUTINES CALLED:
                384  ;                   REGLOAD
                385  ;
                386  ;*********************************************
0530& AE 00     387  LCDEND    LDX     #0        ;SET INDEX TO ZERO.
0532& E6 21&    388  LCDENDL1  LDA     LCD1,X    ;LOAD LCD FROM RAM.
0534& E7 14&    389            STA     PLCD1,X   ;STORE IT IN LCD REG.
0536& 5C        390            INCX              ;INDEX = INDEX + 1.
0537& A3 07     391            CPX     #7        ;DONE?
0539& 23 F7     392            BLS     LCDENDL1;
053B& BD A3&    393            JSR     REGLOAD   ;LOAD X & A REGS.
053D& 81        394            RTS               ;
                395  $EJ
                396  ;************* LCDNUM    *********************
                397  ;*********************************************
                398  ;
                399  ;THIS SUBROUTINE TURNS ON OR OFF THE CORRECT
                400  ;BITS IN THE LCD RAM AREA WHICH CORRESPOND
                401  ;TO THE DISPLAY POSITION AND 7 SEGMENT
                402  ;ARRAY TO BE WRITTEN.
                403  ;
                404  ;*********************************************
                405  ;
                406  ;   INPUT :
                407  ;           SEGLOC CONTAINS THE DIPLAY POSITION
                408  ;           TO BE CHANGED IN BIT WISE FORMAT.
                409  ;           SEGVAL CONTAINS THE 7 SEGMENT (A THRU
                410  ;           G) WHICH MUST BE TURNED ON OR OFF TO
                411  ;           FORM THE DIGIT CORRECTLY.
                412  ;
                413  ;   OUTPUT : (NONE)
                414  ;
                415  ;   REGISTERS SAVED (Y/N) : N
                416  ;   IF "N" ABOVE THEN REGISTERS USED
                417  ;               (* = MODIFIED):
                418  ;                   *X REGISTER
                419  ;
                420  ;   FIELDS USED (* = MODIFIED):
                421  ;                   SEGLOC
                422  ;                   SEGVAL
                423  ;
                424  ;   SUBROUTINES CALLED:
                425  ;                   LCDLOAD
                426  ;                   (JUMPS TO LCDEND)
                427  ;
                428  ;*********************************************
053E& CC 066A&  429  LCDLOC0J  JMP     LCDLOC0  ;THESE ARE USED TO
0541& CC 060C&  430  LCDLOC1J  JMP     LCDLOC1  ;BRANCH FURTHER
0544& CC 05AE&  431  LCDLOC2J  JMP     LCDLOC2  ;THAN 128 BYTES.
0547& 00 2A& F4 432  LCDNUM    BRSET   0,SEGLOC,LCDLOC0J;POS. 0.
```

```
054A& 02 2A& F4      433                    BRSET   1,SEGLOC,LCDLOC1J;POS. 1.
054D& 04 2A& F4      434                    BRSET   2,SEGLOC,LCDLOC2J;POS. 2.
0550& AE 16          435                    LDX     #22      ;TURN OFF ALL 7
0552& CD 03BA&       436                    JSR     LCDLOAD  ;SEGMENTS IN DISPLAY
0555& AE 17          437                    LDX     #23      ;POSITION #3.
0557& CD 03BA&       438                    JSR     LCDLOAD  ;
055A& AE 18          439                    LDX     #24      ;
055C& CD 03BA&       440                    JSR     LCDLOAD  ;
055F& AE 19          441                    LDX     #25      ;
0561& CD 03BA&       442                    JSR     LCDLOAD  ;
0564& AE 1A          443                    LDX     #26      ;
0566& CD 03BA&       444                    JSR     LCDLOAD  ;
0569& AE 1B          445                    LDX     #27      ;
056B& CD 03BA&       446                    JSR     LCDLOAD  ;
056E& AE 1C          447                    LDX     #28      ;
0570& CD 03BA&       448                    JSR     LCDLOAD  ;
0573& 01 29& 05      449                    BRCLR   0,SEGVAL,SEG3B;TURN ON SEG A?
0576& AE 1D          450                    LDX     #29      ;YES, LOAD RAM OFFSET
0578& CD 03BA&       451                    JSR     LCDLOAD  ;AND DO IT.
057B& 03 29& 05      452    SEG3B           BRCLR   1,SEGVAL,SEG3C;TURN ON SEG B?
057E& AE 1E          453                    LDX     #30      ;YES, LOAD RAM OFFSET
0580& CD 03BA&       454                    JSR     LCDLOAD  ;AND DO IT.
0583& 05 29& 05      455    SEG3C           BRCLR   2,SEGVAL,SEG3D;TURN ON SEG C?
0586& AE 1F          456                    LDX     #31      ;YES, LOAD RAM OFFSET
0588& CD 03BA&       457                    JSR     LCDLOAD  ;AND DO IT.
058B& 07 29& 05      458    SEG3D           BRCLR   3,SEGVAL,SEG3E;TURN ON SEG D?
058E& AE 20          459                    LDX     #32      ;YES, LOAD RAM OFFSET
0590& CD 03BA&       460                    JSR     LCDLOAD  ;AND DO IT.
0593& 09 29& 05      461    SEG3E           BRCLR   4,SEGVAL,SEG3F;TURN ON SEG E?
0596& AE 21          462                    LDX     #33      ;YES, LOAD RAM OFFSET
0598& CD 03BA&       463                    JSR     LCDLOAD  ;AND DO IT.
059B& 0B 29& 05      464    SEG3F           BRCLR   5,SEGVAL,SEG3G;TURN ON SEG F?
059E& AE 22          465                    LDX     #34      ;YES, LOAD RAM OFFSET
05A0& CD 03BA&       466                    JSR     LCDLOAD  ;AND DO IT.
05A3& 0D 29& 05      467    SEG3G           BRCLR   6,SEGVAL,LCDSEG3;TURN ON G?
05A6& AE 23          468                    LDX     #35      ;YES, LOAD RAM OFFSET
05A8& CD 03BA&       469                    JSR     LCDLOAD  ;AND DO IT.
05AB& CC 0530&       470    LCDSEG3         JMP     LCDEND   ;REFRESH DISPLAY.
05AE& AE 24          471    LCDLOC2         LDX     #36      ;TURN OFF ALL 7
05B0& CD 03BA&       472                    JSR     LCDLOAD  ;SEGMENTS IN
05B3& AE 25          473                    LDX     #37      ;DISPLAY POSITION
05B5& CD 03BA&       474                    JSR     LCDLOAD  ;#2.
05B8& AE 26          475                    LDX     #38      ;
05BA& CD 03BA&       476                    JSR     LCDLOAD  ;
05BD& AE 27          477                    LDX     #39      ;
05BF& CD 03BA&       478                    JSR     LCDLOAD  ;
05C2& AE 28          479                    LDX     #40      ;
05C4& CD 03BA&       480                    JSR     LCDLOAD  ;
05C7& AE 29          481                    LDX     #41      ;
05C9& CD 03BA&       482                    JSR     LCDLOAD  ;
05CC& AE 2A          483                    LDX     #42      ;
05CE& CD 03BA&       484                    JSR     LCDLOAD  ;
05D1& 01 29& 05      485                    BRCLR   0,SEGVAL,SEG2B;TURN ON SEG A?
05D4& AE 2B          486                    LDX     #43      ;YES, LOAD RAM OFFSET
05D6& CD 03BA&       487                    JSR     LCDLOAD  ;AND DO IT.
05D9& 03 29& 05      488    SEG2B           BRCLR   1,SEGVAL,SEG2C;TURN ON SEG B?
05DC& AE 2C          489                    LDX     #44      ;YES, LOAD RAM OFFSET
05DE& CD 03BA&       490                    JSR     LCDLOAD  ;AND DO IT.
05E1& 05 29& 05      491    SEG2C           BRCLR   2,SEGVAL,SEG2D;TURN ON SEG C?
05E4& AE 2D          492                    LDX     #45      ;YES, LOAD RAM OFFSET
05E6& CD 03BA&       493                    JSR     LCDLOAD  ;AND DO IT.
05E9& 07 29& 05      494    SEG2D           BRCLR   3,SEGVAL,SEG2E;TURN ON SEG D?
05EC& AE 2E          495                    LDX     #46      ;YES, LOAD RAM OFFSET
05EE& CD 03BA&       496                    JSR     LCDLOAD  ;AND DO IT.
05F1& 09 29& 05      497    SEG2E           BRCLR   4,SEGVAL,SEG2F;TURN ON SEG E?
05F4& AE 2F          498                    LDX     #47      ;YES, LOAD RAM OFFSET
05F6& CD 03BA&       499                    JSR     LCDLOAD  ;AND DO IT.
05F9& 0B 29& 05      500    SEG2F           BRCLR   5,SEGVAL,SEG2G;TURN ON SEG F?
05FC& AE 30          501                    LDX     #48      ;YES, LOAD RAM OFFSET
05FE& CD 03BA&       502                    JSR     LCDLOAD  ;AND DO IT.
0601& 0D 29& 05      503    SEG2G           BRCLR   6,SEGVAL,LCDSEG2;TURN ON G?
0604& AE 31          504                    LDX     #49      ;YES, LOAD RAM OFFSET
0606& CD 03BA&       505                    JSR     LCDLOAD  ;AND DO IT.
```

| | | | | | |
|---|---|---|---|---|---|
| 0609& CC 0530& | 506 | LCDSEG2 | JMP | LCDEND | ;REFRESH DISPLAY. |
| 060C& AE 32 | 507 | LCDLOC1 | LDX | #50 | ;TURN OFF ALL 7 |
| 060E& CD 03BA& | 508 | | JSR | LCDLOAD | ;SEGMENTS ON DISPLAY |
| 0611& AE 33 | 509 | | LDX | #51 | ;POSITION #1. |
| 0613& CD 03BA& | 510 | | JSR | LCDLOAD | ; |
| 0616& AE 34 | 511 | | LDX | #52 | ; |
| 0618& CD 03BA& | 512 | | JSR | LCDLOAD | ; |
| 061B& AE 35 | 513 | | LDX | #53 | ; |
| 061D& CD 03BA& | 514 | | JSR | LCDLOAD | ; |
| 0620& AE 36 | 515 | | LDX | #54 | ; |
| 0622& CD 03BA& | 516 | | JSR | LCDLOAD | ; |
| 0625& AE 37 | 517 | | LDX | #55 | ; |
| 0627& CD 03BA& | 518 | | JSR | LCDLOAD | ; |
| 062A& AE 38 | 519 | | LDX | #56 | ; |
| 062C& CD 03BA& | 520 | | JSR | LCDLOAD | ; |
| 062F& 01 29& 05 | 521 | | BRCLR | 0,SEGVAL,SEG1B;TURN ON SEG A? |
| 0632& AE 39 | 522 | | LDX | #57 | ;YES, LOAD RAM OFFSET |
| 0634& CD 03BA& | 523 | | JSR | LCDLOAD | ;AND DO IT. |
| 0637& 03 29& 05 | 524 | SEG1B | BRCLR | 1,SEGVAL,SEG1C;TURN ON SEG B? |
| 063A& AE 3A | 525 | | LDX | #58 | ;YES, LOAD RAM OFFSET |
| 063C& CD 03BA& | 526 | | JSR | LCDLOAD | ;AND DO IT. |
| 063F& 05 29& 05 | 527 | SEG1C | BRCLR | 2,SEGVAL,SEG1D;TURN ON SEG C? |
| 0642& AE 3B | 528 | | LDX | #59 | ;YES, LOAD RAM OFFSET |
| 0644& CD 03BA& | 529 | | JSR | LCDLOAD | ;AND DO IT. |
| 0647& 07 29& 05 | 530 | SEG1D | BRCLR | 3,SEGVAL,SEG1E;TURN ON SEG D? |
| 064A& AE 3C | 531 | | LDX | #60 | ;YES, LOAD RAM OFFSET |
| 064C& CD 03BA& | 532 | | JSR | LCDLOAD | ;AND DO IT. |
| 064F& 09 29& 05 | 533 | SEG1E | BRCLR | 4,SEGVAL,SEG1F;TURN ON SEG E? |
| 0652& AE 3D | 534 | | LDX | #61 | ;YES, LOAD RAM OFFSET |
| 0654& CD 03BA& | 535 | | JSR | LCDLOAD | ;AND DO IT. |
| 0657& 0B 29& 05 | 536 | SEG1F | BRCLR | 5,SEGVAL,SEG1G;TURN ON SEG F? |
| 065A& AE 3E | 537 | | LDX | #62 | ;YES, LOAD RAM OFFSET |
| 065C& CD 03BA& | 538 | | JSR | LCDLOAD | ;AND DO IT. |
| 065F& 0D 29& 05 | 539 | SEG1G | BRCLR | 6,SEGVAL,LCDSEG1;TURN ON G? |
| 0662& AE 3F | 540 | | LDX | #63 | ;YES. LOAD RAM OFFSET |
| 0664& CD 03BA& | 541 | | JSR | LCDLOAD | ;AND DO IT. |
| 0667& CC 0530& | 542 | LCDSEG1 | JMP | LCDEND | ;REFRESH DISPLAY. |
| 066A& AE 40 | 543 | LCDLOC0 | LDX | #64 | ;TURN OFF ALL 7 |
| 066C& CD 03BA& | 544 | | JSR | LCDLOAD | ;SEGMENTS IN |
| 066F& AE 41 | 545 | | LDX | #65 | ;DISPLAY POSITION |
| 0671& CD 03BA& | 546 | | JSR | LCDLOAD | ;#0. |
| 0674& AE 42 | 547 | | LDX | #66 | ; |
| 0676& CD 03BA& | 548 | | JSR | LCDLOAD | ; |
| 0679& AE 43 | 549 | | LDX | #67 | ; |
| 067B& CD 03BA& | 550 | | JSR | LCDLOAD | ; |
| 067E& AE 44 | 551 | | LDX | #68 | ; |
| 0680& CD 03BA& | 552 | | JSR | LCDLOAD | ; |
| 0683& AE 45 | 553 | | LDX | #69 | ; |
| 0685& CD 03BA& | 554 | | JSR | LCDLOAD | ; |
| 0688& AE 46 | 555 | | LDX | #70 | ; |
| 068A& CD 03BA& | 556 | | JSR | LCDLOAD | ; |
| 068D& 01 29& 05 | 557 | | BRCLR | 0,SEGVAL,SEG0B;TURN ON SEG A? |
| 0690& AE 47 | 558 | | LDX | #71 | ;YES, LOAD RAM OFFSET |
| 0692& CD 03BA& | 559 | | JSR | LCDLOAD | ;AND DO IT. |
| 0695& 03 29& 05 | 560 | SEG0B | BRCLR | 1,SEGVAL,SEG0C;TURN ON SEG B? |
| 0698& AE 48 | 561 | | LDX | #72 | ;YES, LOAD RAM OFFSET |
| 069A& CD 03BA& | 562 | | JSR | LCDLOAD | ;AND DO IT. |
| 069D& 05 29& 05 | 563 | SEG0C | BRCLR | 2,SEGVAL,SEG0D;TURN ON SEG C? |
| 06A0& AE 49 | 564 | | LDX | #73 | ;YES, LOAD RAM OFFSET |
| 06A2& CD 03BA& | 565 | | JSR | LCDLOAD | ;AND DO IT. |
| 06A5& 07 29& 05 | 566 | SEG0D | BRCLR | 3,SEGVAL,SEG0E;TURN ON SEG D? |
| 06A8& AE 4A | 567 | | LDX | #74 | ;YES, LOAD RAM OFFSET |
| 06AA& CD 03BA& | 568 | | JSR | LCDLOAD | ;AND DO IT. |
| 06AD& 09 29& 05 | 569 | SEG0E | BRCLR | 4,SEGVAL,SEG0F;TURN ON SEG E? |
| 06B0& AE 4B | 570 | | LDX | #75 | ;YES, LOAD RAM OFFSET |
| 06B2& CD 03BA& | 571 | | JSR | LCDLOAD | ;AND DO IT. |
| 06B5& 0B 29& 05 | 572 | SEG0F | BRCLR | 5,SEGVAL,SEG0G;TURN ON SEG F? |
| 06B8& AE 4C | 573 | | LDX | #76 | ;YES, LOAD RAM OFFSET |
| 06BA& CD 03BA& | 574 | | JSR | LCDLOAD | ;AND DO IT. |
| 06BD& 0D 29& 05 | 575 | SEG0G | BRCLR | 6,SEGVAL,LCDSEG0;TURN ON G? |
| 06C0& AE 4D | 576 | | LDX | #77 | ;YES, LOAD RAM OFFSET |
| 06C2& CD 03BA& | 577 | | JSR | LCDLOAD | ;AND DO IT. |
| 06C5& CC 0530& | 578 | LCDSEG0 | JMP | LCDEND | ;REFRESH DISPLAY. |
| | 579 | $EJ | | | |

```
                580     ;************ DISPNUM *********************
                581     ;*******************************************
                582     ;
                583     ;THIS SUBROUTINE TAKES A 16 BIT BCD (BINARY
                584     ;CODED DECIMAL) NUMBER AND DISPLAYS IT ON THE
                585     ;LCD WITH THE OPTION OF LEADING ZERO
                586     ;SUPPRESSION.
                587     ;
                588     ;*******************************************
                589     ;
                590     ;   INPUT :
                591     ;           DISPWORD & DISPWORD+1 CONTAINS THE
                592     ;           16 BIT BCD NUMBER TO BE WRITTEN ON
                593     ;           THE LCD.
                594     ;           THE X REGISTER IS NONZERO TO SUPPRESS
                595     ;           LEADING 0'S IN THE NUMBER.
                596     ;           (IE. 0012 WILL BE DISPLAYED
                597     ;           AS    12 RIGHT JUSTIFIED).
                598     ;
                599     ;   OUTPUT : (NONE)
                600     ;
                601     ;   REGISTERS SAVED (Y/N) : Y
                602     ;   IF "N" ABOVE THEN REGISTERS USED
                603     ;             (* = MODIFIED):
                604     ;
                605     ;   FIELDS USED (* = MODIFIED):
                606     ;             DISPWORD
                607     ;             XSW        /BIT:4
                608     ;
                609     ;   SUBROUTINES CALLED:
                610     ;             REGSAVE
                611     ;             REGLOAD
                612     ;             LCDPRT
                613     ;
                614     ;*******************************************
06C8& BD 94&    615     DISPNUM   JSR    REGSAVE  ;SAVE X & A REGS.
06CA& A3 00     616               CPX    #0       ;X REG NOT = 0?
06CC& 26 04     617               BNE    DISPNUMA;
06CE& 19 41&    618               BCLR   4,XSW    ;NO, SET NO SUPPRESS.
06D0& 20 02     619               BRA    DISPNUMB;BRANCH AROUND.
06D2& 18 41&    620     DISPNUMA  BSET   4,XSW    ;YES, SET 0 SUPPRESS.
06D4& B6 47&    621     DISPNUMB  LDA    DISPWORD;LOAD HIGH BYTE.
06D6& 44        622               LSRA            ;SHIFT IT RIGHT 4
06D7& 44        623               LSRA            ;BITS TO GET LEFT
06D8& 44        624               LSRA            ;MOST DIGIT.
06D9& 44        625               LSRA            ;
06DA& 26 07     626               BNE    DISPLP1  ;NONZERO DIGIT?
06DC& 09 41& 06 627               BRCLR  4,XSW,DISPLP2;NO, SUPPRESS 0?
06DF& A6 10     628               LDA    #16      ;YES, LOAD BLANK.
06E1& 20 02     629               BRA    DISPLP2  ;BRANCH AROUND.
06E3& 19 41&    630     DISPLP1   BCLR   4,XSW    ;NO MORE SUPPRESS.
06E5& 97        631     DISPLP2   TAX             ;PUT A IN X REG.
06E6& A6 03     632               LDA    #3       ;LCD POS. #3.
06E8& CD 044E&  633               JSR    LCDPRT   ;WRITE IT.
06EB& B6 47&    634               LDA    DISPWORD;LOAD HIGH BYTE.
06ED& A4 0F     635               AND    #0FH     ;MASK OFF LEFT DIGIT.
06EF& 26 07     636               BNE    DISPLP3  ;DIGIT NONZERO?
06F1& 09 41& 06 637               BRCLR  4,XSW,DISPLP4;NO, SUPPRESS 0?
06F4& A6 10     638               LDA    #16      ;YES, LOAD BLANK.
06F6& 20 02     639               BRA    DISPLP4  ;BRANCH AROUND.
06F8& 19 41&    640     DISPLP3   BCLR   4,XSW    ;NO MORE SUPPRESS.
06FA& 97        641     DISPLP4   TAX             ;PUT A IN X REG.
06FB& A6 02     642               LDA    #2       ;LCD POS. #2.
06FD& CD 044E&  643               JSR    LCDPRT   ;WRITE IT.
0700& B6 48&    644               LDA    DISPWORD+1;LOAD LOW BYTE.
0702& 44        645               LSRA            ;SHIFT IT RIGHT
0703& 44        646               LSRA            ;4 BITS TO GET
0704& 44        647               LSRA            ;LEFT DIGIT.
0705& 44        648               LSRA            ;
0706& 26 07     649               BNE    DISPLP5  ;DIGIT NON-ZERO?
0708& 09 41& 06 650               BRCLR  4,XSW,DISPLP6;NO, SUPPRESS 0?
070B& A6 10     651               LDA    #16      ;YES, LOAD BLANK.
```

```
070D& 20 02         652            BRA     DISPLP6   ;BRANCH AROUND.
070F& 19 41&        653   DISPLP5  BCLR    4,XSW     ;NO MORE SUPPRESS.
0711& 97            654   DISPLP6  TAX               ;PUT A IN X REG.
0712& A6 01         655            LDA     #1        ;LCD POS. #1.
0714& CD 044E&      656            JSR     LCDPRT    ;WRITE IT.
0717& B6 48&        657            LDA     DISPWORD+1;LOAD LOW BYTE.
0719& A4 0F         658            AND     #0FH      ;MASK OFF LEFT DIGIT.
071B& 97            659            TAX               ;PUT A IN X REG.
071C& A6 00         660            LDA     #0        ;LCD POS. #0.
071E& CD 044E&      661            JSR     LCDPRT    ;WRITE IT.
0721& BD A3&        662            JSR     REGLOAD   ;LOAD X & A REGS.
0723& 81            663            RTS               ;
                    664   $EJ
                    665   ;************** BCD       *********************
                    666   ;**********************************************
                    667   ;
                    668   ;THIS SUBROUTINE TAKES AN 8 BIT BINARY NUMBER
                    669   ;AND CONVERTS IT TO A 16 BIT BINARY CODED
                    670   ;DECIMAL NUMBER EQUIVALENT.
                    671   ;
                    672   ;**********************************************
                    673   ;
                    674   ;  INPUT :
                    675   ;        A REGISTER HAS THE BINARY NUMBER TO
                    676   ;        BE CONVERTED.
                    677   ;
                    678   ;  OUTPUT :
                    679   ;        DISPWORD CONTAINS THE 16 BIT BCD
                    680   ;        NUMBER EQUIVALENT.
                    681   ;
                    682   ;  REGISTERS SAVED (Y/N) : Y
                    683   ;  IF "N" ABOVE THEN REGISTERS USED
                    684   ;        (* = MODIFIED):
                    685   ;
                    686   ;  FIELDS USED (* = MODIFIED):
                    687   ;             DISPWORD
                    688   ;
                    689   ;  SUBROUTINES CALLED:
                    690   ;             REGSAVE
                    691   ;             REGLOAD
                    692   ;             LCDPRT
                    693   ;
                    694   ;**********************************************
0724& BD 94&        695   BCD      JSR     REGSAVE   ;SAVE X & A REGS.
0726& AE 00         696            LDX     #0        ;X TO COUNT HUNDREDS.
0728& A0 64         697   BCDLP1   SUB     #100      ;A = A - 100.
072A& 25 03         698            BCS     BCDLP2    ;IS A < 0?
072C& 5C            699            INCX              ;NO, X = X + 1.
072D& 20 F9         700            BRA     BCDLP1    ;DO AGAIN.
072F& AB 64         701   BCDLP2   ADD     #100      ;MAKE A > 0.
0731& BF 47&        702            STX     DISPWORD  ;STORE HUNDREDS.
0733& AE 00         703            LDX     #0        ;X TO COUNT TENS.
0735& A0 0A         704   BCDLP3   SUB     #10       ;A = A - 10.
0737& 25 03         705            BCS     BCDLP4    ;IS A < 0?
0739& 5C            706            INCX              ;NO, X = X + 1.
073A& 20 F9         707            BRA     BCDLP3    ;DO AGAIN.
073C& AB 0A         708   BCDLP4   ADD     #10       ;MAKE A > 0.
073E& B7 48&        709            STA     DISPWORD+1;STORE ONES.
0740& 58            710            ASLX              ;PUT TENS DIGIT IN
0741& 58            711            ASLX              ;LEFT HALF OF X.
0742& 58            712            ASLX              ;
0743& 58            713            ASLX              ;
0744& 9F            714            TXA               ;PUT X IN A.
0745& BB 48&        715            ADD     DISPWORD+1;A = A + (LOW BYTE)
0747& B7 48&        716            STA     DISPWORD+1;STORE TENS & ONES.
0749& BD A3&        717            JSR     REGLOAD   ;LOAD X & A REGS.
074B& 81            718            RTS
                    719
                    54            INCLUDE "INSUTIL.ASM" ; MISC. UTILS
074C& BD 94&        1     SPCHTLK  JSR     REGSAVE
074E& CD 0AE9&      2              JSR     PTON
0751& B7 00&        3              STA     PADATA
0753& 13 41&        4              BCLR    1,XSW
```

```
0755& 15 01&      5                    BCLR    2,PBDATA
0757& 14 01&      6                    BSET    2,PBDATA
0759& B6 4A&      7                    LDA     TIKSEC
075B& AB 03       8                    ADD     #3
075D& A1 3C       9                    CMP     #60
075F& 25 02      10                    BCS     SPCHTLK1
0761& A0 3C      11                    SUB     #60
0763& 02 41& 04  12   SPCHTLK1  BRSET   1,XSW,SPCHTLK2
0766& B1 4A&     13                    CMP     TIKSEC
0768& 26 F9      14                    BNE     SPCHTLK1
076A& CD 0AF9&   15   SPCHTLK2  JSR    PTOFF
076D& 13 41&     16                    BCLR    1,XSW
076F& 15 41&     17                    BCLR    2,XSW
0771& A6 08      18                    LDA     #8
0773& CD 0900&   19                    JSR     TIMER
0776& BD A3&     20                    JSR     REGLOAD
0778& 81         21                    RTS
0779& 9A         22   SPCHBSY   CLI
077A& 12 41&     23                    BSET    1,XSW
077C& 80         24                    RTI
077D& BD 94&     25   SPCHNUM   JSR    REGSAVE
077F& B6 47&     26                    LDA     DISPWORD
0781& A4 F0      27                    AND     #0F0H
0783& 44         28                    LSRA
0784& 44         29                    LSRA
0785& 44         30                    LSRA
0786& 44         31                    LSRA
0787& 27 0A      32                    BEQ     SPCHNUMB
0789& AB 08      33                    ADD     #8
078B& CD 074C&   34                    JSR     SPCHTLK
078E& A6 22      35                    LDA     #22H
0790& CD 074C&   36                    JSR     SPCHTLK
0793& B6 47&     37   SPCHNUMB  LDA    DISPWORD
0795& A4 0F      38                    AND     #0FH
0797& 27 0C      39                    BEQ     SPCHNUM1
0799& AB 08      40                    ADD     #8
079B& CD 074C&   41                    JSR     SPCHTLK
079E& A6 1B      42                    LDA     #1BH
07A0& CD 074C&   43                    JSR     SPCHTLK
07A3& 20 04      44                    BRA     SPCHNUMA
07A5& B6 48&     45   SPCHNUM1  LDA    DISPWORD+1
07A7& 27 32      46                    BEQ     SPCHNUM5
07A9& B6 48&     47   SPCHNUMA  LDA    DISPWORD+1
07AB& 44         48                    LSRA
07AC& 44         49                    LSRA
07AD& 44         50                    LSRA
07AE& 44         51                    LSRA
07AF& 27 1D      52                    BEQ     SPCHNUM4
07B1& A1 01      53                    CMP     #1
07B3& 26 14      54                    BNE     SPCHNUM3
07B5& B6 48&     55                    LDA     DISPWORD+1
07B7& A4 0F      56                    AND     #0FH
07B9& 27 07      57                    BEQ     SPCHNUM2
07BB& A0 01      58                    SUB     #1
07BD& CD 074C&   59                    JSR     SPCHTLK
07C0& 20 1E      60                    BRA     SPCHNUM6
07C2& A6 12      61   SPCHNUM2  LDA    #12H
07C4& CD 074C&   62                    JSR     SPCHTLK
07C7& 20 17      63                    BRA     SPCHNUM6
07C9& AB 11      64   SPCHNUM3  ADD    #11H
07CB& CD 074C&   65                    JSR     SPCHTLK
07CE& B6 48&     66   SPCHNUM4  LDA    DISPWORD+1
07D0& A4 0F      67                    AND     #0FH
07D2& 27 0C      68                    BEQ     SPCHNUM6
07D4& AB 08      69                    ADD     #8
07D6& CD 074C&   70                    JSR     SPCHTLK
07D9& 20 05      71                    BRA     SPCHNUM6
07DB& A6 23      72   SPCHNUM5  LDA    #23H
07DD& CD 074C&   73                    JSR     SPCHTLK
07E0& BD A3&     74   SPCHNUM6  JSR    REGLOAD
07E2& 81         75                    RTS
07E3& 9A         76   TBINT     CLI
07E4& 3C 4A&     77                    INC     TIKSEC
```

```
07E6& BE 4A&        78                  LDX     TIKSEC
07E8& A3 3C         79                  CPX     #60
07EA& 26 02         80                  BNE     TBINT1
07EC& 20 01         81                  BRA     TBINT2
07EE& 80            82      TBINT1      RTI
07EF& 3F 4A&        83      TBINT2      CLR     TIKSEC
07F1& 3C 4B&        84                  INC     TIKMIN
07F3& BE 4B&        85                  LDX     TIKMIN
07F5& A3 3C         86                  CPX     #60
07F7& 26 F5         87                  BNE     TBINT1
07F9& 3F 4B&        88                  CLR     TIKMIN
07FB& 3C 4C&        89                  INC     TIKHR
07FD& BE 4C&        90                  LDX     TIKHR
07FF& A3 18         91                  CPX     #24
0801& 26 EB         92                  BNE     TBINT1
0803& 3F 4C&        93                  CLR     TIKHR
0805& 3C 4D&        94                  INC     TIKDY
0807& BE 4E&        95                  LDX     TIKMO
0809& 5A            96                  DECX
080A& E6 B2&        97                  LDA     TIKTABL,X
080C& A3 01         98                  CPX     #1
080E& 26 04         99                  BNE     TBINT3
0810& 0B 41& 01    100                  BRCLR   5,XSW,TBINT3
0813& 4C           101                  INCA
0814& 4C           102      TBINT3      INCA
0815& B1 4D&       103                  CMP     TIKDY
0817& 26 28        104                  BNE     TBINT7
0819& AE 01        105                  LDX     #1
081B& BF 4D&       106                  STX     TIKDY
081D& 3C 4E&       107                  INC     TIKMO
081F& BE 4E&       108                  LDX     TIKMO
0821& A3 0D        109                  CPX     #13
0823& 26 1C        110                  BNE     TBINT7
0825& AE 01        111                  LDX     #1
0827& BF 4E&       112                  STX     TIKMO
0829& 3C 4F&       113                  INC     TIKYR
082B& B6 4F&       114                  LDA     TIKYR
082D& A1 64        115                  CMP     #100
082F& 26 04        116                  BNE     TBINT4
0831& 3F 4F&       117                  CLR     TIKYR
0833& 20 06        118                  BRA     TBINT5
0835& A0 04        119      TBINT4      SUB     #4
0837& 25 06        120                  BCS     TBINT6
0839& 26 FA        121                  BNE     TBINT4
083B& 1A 41&       122      TBINT5      BSET    5,XSW
083D& 20 02        123                  BRA     TBINT7
083F& 1B 41&       124      TBINT6      BCLR    5,XSW
0841& 80           125      TBINT7      RTI
0842& 3F 4C&       126      TBINIT      CLR     TIKHR
0844& 3F 4B&       127                  CLR     TIKMIN
0846& 3F 4A&       128                  CLR     TIKSEC
0848& A6 01        129                  LDA     #1
084A& B7 4E&       130                  STA     TIKMO
084C& B7 4D&       131                  STA     TIKDY
084E& A6 50        132                  LDA     #80
0850& B7 4F&       133                  STA     TIKYR
0852& 1A 41&       134                  BSET    5,XSW
0854& 18 1C&       135                  BSET    4,SYSCTRL
0856& 1D 1C&       136                  BCLR    6,SYSCTRL
0858& 81           137                  RTS
0859& 9B           138      MPUINIT     SEI
085A& A6 63        139                  LDA     #63H
085C& B7 1C&       140                  STA     SYSCTRL
085E& A6 5B        141                  LDA     #5BH
0860& B7 09&       142                  STA     TIMCTRL
0862& A6 48        143                  LDA     #48H
0864& B7 0F&       144                  STA     ADCCTRL
0866& 3F 20&       145                  CLR     SAVE259
0868& 3F 31&       146                  CLR     REGPTR
086A& A6 FF        147                  LDA     #0FFH
086C& B7 04&       148                  STA     PADIR
086E& B7 05&       149                  STA     PBDIR
0870& 3F 06&       150                  CLR     PCDIR
```

| | | | | | |
|---|---|---|---|---|---|
| 0872& | A6 AF | 151 | | LDA | #0AFH |
| 0874& | B7 01& | 152 | | STA | PBDATA |
| 0876& | 3F 00& | 153 | | CLR | PADATA |
| 0878& | CD 0AC5& | 154 | | JSR | LEDOFFG |
| 087B& | CD 0ADD& | 155 | | JSR | LEDOFFR |
| 087E& | CD 0AF9& | 156 | | JSR | PTOFF |
| 0881& | CD 0842& | 157 | | JSR | TBINIT |
| 0884& | CD 042E& | 158 | | JSR | LCDCLR |
| 0887& | 81 | 159 | | RTS | |
| 0888& | BD 94& | 160 | PRINT | JSR | REGSAVE |
| 088A& | 1F 2D& | 161 | | BCLR | 7,HALTSW |
| 088C& | 97 | 162 | | TAX | |
| 088D& | B6 4A& | 163 | | LDA | TIKSEC |
| 088F& | AB 03 | 164 | | ADD | #3 |
| 0891& | A1 3C | 165 | | CMP | #60 |
| 0893& | 25 02 | 166 | | BCS | PRINT1 |
| 0895& | A0 3C | 167 | | SUB | #60 |
| 0897& | 00 02& 08 | 168 | PRINT1 | BRSET | 0,PCDATA,PRINT2 |
| 089A& | BF 00& | 169 | | STX | PADATA |
| 089C& | 17 01& | 170 | | BCLR | 3,PBDATA |
| 089E& | 16 01& | 171 | | BSET | 3,PBDATA |
| 08A0& | 20 06 | 172 | | BRA | PRINT3 |
| 08A2& | B1 4A& | 173 | PRINT2 | CMP | TIKSEC |
| 08A4& | 26 F1 | 174 | | BNE | PRINT1 |
| 08A6& | 1E 2D& | 175 | | BSET | 7,HALTSW |
| 08A8& | BD A3& | 176 | PRINT3 | JSR | REGLOAD |
| 08AA& | 81 | 177 | | RTS | |
| 08AB& | BD 94& | 178 | HALT | JSR | REGSAVE |
| 08AD& | B6 4C& | 179 | HALT1 | LDA | TIKHR |
| 08AF& | 11 2D& | 180 | | BCLR | 0,HALTSW |
| 08B1& | 13 2D& | 181 | | BCLR | 1,HALTSW |
| 08B3& | 15 2D& | 182 | | BCLR | 2,HALTSW |
| 08B5& | 17 2D& | 183 | | BCLR | 3,HALTSW |
| 08B7& | 19 2D& | 184 | | BCLR | 4,HALTSW |
| 08B9& | 16 1C& | 185 | | BSET | 3,SYSCTRL |
| 08BB& | B1 4C& | 186 | | CMP | TIKHR |
| 08BD& | 27 02 | 187 | | BEQ | HALT2 |
| 08BF& | 18 2D& | 188 | | BSET | 4,HALTSW |
| 08C1& | 00 02& 15 | 189 | HALT2 | BRSET | 0,PCDATA,HALT3 |
| 08C4& | 1D 41& | 190 | | BCLR | 6,XSW |
| 08C6& | 1E 41& | 191 | | BSET | 7,XSW |
| 08C8& | 3F 52& | 192 | | CLR | XDATAL |
| 08CA& | AE 01 | 193 | | LDX | #1 |
| 08CC& | BF 51& | 194 | | STX | XDATAH |
| 08CE& | CD 09CA& | 195 | | JSR | RAMREAD |
| 08D1& | BE 46& | 196 | | LDX | XDATA |
| 08D3& | A3 AA | 197 | | CPX | #0AAH |
| 08D5& | 26 D6 | 198 | | BNE | HALT1 |
| 08D7& | 10 2D& | 199 | | BSET | 0,HALTSW |
| 08D9& | 02 02& 02 | 200 | HALT3 | BRSET | 1,PCDATA,HALT4 |
| 08DC& | 12 2D& | 201 | | BSET | 1,HALTSW |
| 08DE& | 04 02& 02 | 202 | HALT4 | BRSET | 2,PCDATA,HALT5 |
| 08E1& | 14 2D& | 203 | | BSET | 2,HALTSW |
| 08E3& | 06 02& 02 | 204 | HALT5 | BRSET | 3,PCDATA,HALT6 |
| 08E6& | 16 2D& | 205 | | BSET | 3,HALTSW |
| 08E8& | 00 41& 06 | 206 | HALT6 | BRSET | 0,XSW,HALT7 |
| 08EB& | B6 2D& | 207 | | LDA | HALTSW |
| 08ED& | A4 1F | 208 | | AND | #1FH |
| 08EF& | 27 BC | 209 | | BEQ | HALT1 |
| 08F1& | BD A3& | 210 | HALT7 | JSR | REGLOAD |
| 08F3& | 81 | 211 | | RTS | |
| 08F4& | 9A | 212 | TIMINT | CLI | |
| 08F5& | 3A 2C& | 213 | | DEC | TIMDLY |
| 08F7& | B6 2C& | 214 | | LDA | TIMDLY |
| 08F9& | 26 04 | 215 | | BNE | TIMINT1 |
| 08FB& | 1C 09& | 216 | | BSET | 6,TIMCTRL |
| 08FD& | 10 41& | 217 | | BSET | 0,XSW |
| 08FF& | 80 | 218 | TIMINT1 | RTI | |
| 0900& | 11 41& | 219 | TIMER | BCLR | 0,XSW |
| 0902& | B7 2C& | 220 | | STA | TIMDLY |
| 0904& | 3F 08& | 221 | | CLR | TIMDATA |
| 0906& | 1D 09& | 222 | | BCLR | 6,TIMCTRL |
| 0908& | 04 41& 03 | 223 | | BRSET | 2,XSW,TIMER2 |

```
090B& 01 41& FD    224        TIMER1   BRCLR   0,XSW,TIMER1
090E& 81           225        TIMER2   RTS
                   226
                    55                 INCLUDE "INSRAM.ASM"  ; RAM I/O
                     1        $EJ
                     2        ;************ TOGL259H *********************
                     3        ;*******************************************
                     4        ;
                     5        ;THIS SUBROUTINE WILL GATE A BIT INTO THE
                     6        ;259-2 CHIP WITHOUT AFFECTING THE 259-1
                     7        ;OUTPUTS.
                     8        ;
                     9        ;*******************************************
                    10        ;
                    11        ;   INPUT :
                    12        ;           PADATA HAS THE BITS TO PERFORM THE
                    13        ;           ON THE 259-2 IN THE HIGH 4 BITS.
                    14        ;
                    15        ;   OUTPUT : (NONE)
                    16        ;
                    17        ;   REGISTERS SAVED (Y/N) : Y
                    18        ;   IF "N" ABOVE THEN REGISTERS USED
                    19        ;           (* = MODIFIED):
                    20        ;
                    21        ;   FIELDS USED (* = MODIFIED):
                    22        ;                *SAVE259
                    23        ;                *PADATA
                    24        ;                *PBDATA   /BIT:1
                    25        ;
                    26        ;   SUBROUTINES CALLED:
                    27        ;                REGSAVE
                    28        ;                REGLOAD
                    29        ;
                    30        ;*******************************************
090F& BD 94&        31        TOGL259H  JSR     REGSAVE  ;SAVE X & A REGS.
0911& B6 20&        32                  LDA     SAVE259  ;GET 259 SETTINGS.
0913& A4 0F         33                  AND     #00FH    ;MASK OFF HIGH HALF.
0915& B7 20&        34                  STA     SAVE259  ;SAVE IT.
0917& B6 00&        35                  LDA     PADATA   ;GET DATA FOR 259-2.
0919& A4 F0         36                  AND     #0F0H    ;MASK OFF LOW HALF.
091B& BA 20&        37                  ORA     SAVE259  ;COMBINE WITH HIGH.
091D& B7 20&        38                  STA     SAVE259  ;SAVE IT.
091F& B7 00&        39                  STA     PADATA   ;SET PORT A.
0921& 13 01&        40                  BCLR    1,PBDATA ;SET 259 GATES LOW.
0923& 12 01&        41                  BSET    1,PBDATA ;SET 259 GATES HIGH.
0925& BD A3&        42                  JSR     REGLOAD  ;LOAD X & A REGS.
0927& 81            43                  RTS              ;
                    44        $EJ
                    45        ;************ TOGL259L *********************
                    46        ;*******************************************
                    47        ;
                    48        ;THIS SUBROUTINE WILL GATE A BIT INTO THE
                    49        ;259-1 CHIP WITHOUT AFFECTING THE 259-2
                    50        ;OUTPUTS.
                    51        ;
                    52        ;*******************************************
                    53        ;
                    54        ;   INPUT :
                    55        ;           PADATA HAS THE BITS TO PERFORM THE
                    56        ;           ON THE 259-1 IN THE LOW 4 BITS.
                    57        ;
                    58        ;   OUTPUT : (NONE)
                    59        ;
                    60        ;   REGISTERS SAVED (Y/N) : Y
                    61        ;   IF "N" ABOVE THEN REGISTERS USED
                    62        ;           (* = MODIFIED):
                    63        ;
                    64        ;   FIELDS USED (* = MODIFIED):
                    65        ;                *SAVE259
                    66        ;                *PADATA
                    67        ;                *PBDATA   /BIT:1
                    68        ;
```

```
            69    ;   SUBROUTINES CALLED:
            70    ;           REGSAVE
            71    ;           REGLOAD
            72    ;
            73    ;*********************************************
0928& BD 94& 74   TOGL259L    JSR     REGSAVE ;SAVE X & A REGS.
0092A& B6 20& 75              LDA     SAVE259 ;GET 259 SETTINGS.
 092C& A4 F0 76               AND     #0F0H   ;MASK OFF LOW HALF.
 092E& B7 20& 77              STA     SAVE259 ;SAVE IT.
 0930& B6 00& 78              LDA     PADATA  ;GET DATA WITH LOW.
 0932& A4 0F  79              AND     #00FH   ;MASK OFF HIGH HALF.
 0934& BA 20& 80              ORA     SAVE259 ;COMBINE WITH HIGH.
 0936& B7 20& 81              STA     SAVE259 ;STORE IT.
 0938& B7 00& 82              STA     PADATA  ;SET PORT A.
 093A& 13 01& 83              BCLR    1,PBDATA;SET 259 GATES LOW.
 093C& 12 01& 84              BSET    1,PBDATA;SET 259 GATES HIGH.
 093E& BD A3& 85              JSR     REGLOAD ;LOAD X & A REGS.
 0940& 81     86              RTS             ;
            87    $EJ
            88    ;************* RAMADDR  *********************
            89    ;*********************************************
            90    ;
            91    ;THIS SUBROUTINE WILL SET THE ADDRESS BITS
            92    ;(A0-A14) OF THE RAM CHIP BY CHANGING THE
            93    ;OUTPUTS OF THE 259-1 AND 259-2 CHIPS.
            94    ;
            95    ;*********************************************
            96    ;
            97    ;   INPUT :
            98    ;       XSW BIT 6,7 HAS THE RAM ACCESS MODE
            99    ;       ON THE 259-1 IN THE LOW 4 BITS.
           100    ;       RAMADRL HAS THE LOW BYTE FOR MODE 0.
           101    ;       RAMADRH HAS THE HIGH BYTE FOR MODE 0.
           102    ;       PCTRL HAS THE LOW BYTE FOR MODE 1.
           103    ;       PCTRH HAS THE HIGH BYTE FOR MODE 1.
           104    ;       XDATAL HAS THE LOW BYTE FOR MODE 2.
           105    ;       XDATAH HAS THE HIGH BYTE FOR MODE 2.
           106    ;
           107    ;   OUTPUT : (NONE)
           108    ;
           109    ;   REGISTERS SAVED (Y/N) : Y
           110    ;   IF "N" ABOVE THEN REGISTERS USED
           111    ;           (* = MODIFIED):
           112    ;
           113    ;   FIELDS USED (* = MODIFIED):
           114    ;                   XSW     /BIT:6,7
           115    ;                   RAMADRL
           116    ;                   RAMADRH
           117    ;                   PCTRL
           118    ;                   PCTRH
           119    ;                   XDATAL
           120    ;                   XDATAH
           121    ;                   *RAMDATAL
           122    ;                   *RAMDATAH
           123    ;                   *PADATA
           124    ;
           125    ;   SUBROUTINES CALLED:
           126    ;           REGSAVE
           127    ;           REGLOAD
           128    ;           TOGL259L
           129    ;           TOGL259H
           130    ;
           131    ;*********************************************
0941& BD 94& 132  RAMADDR     JSR     REGSAVE ;STORE X & A REGS.
0943& BE 41& 133              LDX     XSW     ;GET ACCESS MODE
0945& 54     134              LSRX            ;SHIFT IT TO
0946& 54     135              LSRX            ;BITS 0 & 1.
0947& 54     136              LSRX            ;
0948& 54     137              LSRX            ;
0949& 54     138              LSRX            ;
094A& 54     139              LSRX            ;
094B& 58     140              LSLX            ;FOR 2 BYTE OFFSET.
```

| | | | | | |
|---|---|---|---|---|---|
| 094C& DC 094F& | 141 | | JMP | RAMADDR5,X;INDEXED JUMP. |
| 094F& 20 04 | 142 | RAMADDR5 | BRA | RAMADR5A;MODE 0. |
| 0951& 20 0C | 143 | | BRA | RAMADR5B;MODE 1. |
| 0953& 20 14 | 144 | | BRA | RAMADR5C;MODE 2. |
| 0955& B6 42& | 145 | RAMADR5A | LDA | RAMADRL ;SET LOW AND HIGH |
| 0957& B7 54& | 146 | | STA | RAMDATAL;BYTES FOR MODE 0. |
| 0959& B6 43& | 147 | | LDA | RAMADRH ; |
| 095B& B7 53& | 148 | | STA | RAMDATAH; |
| 095D& 20 12 | 149 | | BRA | RAMADDR6; |
| 095F& B6 55& | 150 | RAMADR5B | LDA | PCTRL ;SET LOW AND HIGH |
| 0961& B7 54& | 151 | | STA | RAMDATAL;BYTES FOR MODE 1. |
| 0963& B6 56& | 152 | | LDA | PCTRH ; |
| 0965& B7 53& | 153 | | STA | RAMDATAH; |
| 0967& 20 08 | 154 | | BRA | RAMADDR6; |
| 0969& B6 52& | 155 | RAMADR5C | LDA | XDATAL ;SET LOW AND HIGH |
| 096B& B7 54& | 156 | | STA | RAMDATAL;BYTES FOR MODE2. |
| 096D& B6 51& | 157 | | LDA | XDATAH ; |
| 096F& B7 53& | 158 | | STA | RAMDATAH; |
| 0971& A6 01 | 159 | RAMADDR6 | LDA | #1 ;GET 1 IN BIT0. |
| 0973& AE 00 | 160 | | LDX | #0 ;START WITH BIT #0. |
| 0975& BF 00& | 161 | RAMADDR1 | STX | PADATA ;STORE TO A PORT. |
| 0977& B5 54& | 162 | | BIT | RAMDATAL;MASK OFF OTHER BITS. |
| 0979& 27 02 | 163 | | BEQ | RAMADDR2;WAS ADDR BIT ZERO? |
| 097B& 16 00& | 164 | | BSET | 3,PADATA;NO, SET 259 DATA IN. |
| 097D& CD 0928& | 165 | RAMADDR2 | JSR | TOGL259L;LOAD 259 OUTPUT PIN. |
| 0980& 5C | 166 | | INCX | ;NEXT BIT NUMBER. |
| 0981& 48 | 167 | | LSLA | ;NEXT BIT WISE POS. |
| 0982& 26 F1 | 168 | | BNE | RAMADDR1;ALL 8 BITS DONE? |
| 0984& A6 01 | 169 | | LDA | #1 ;YES, GET 1 IN BIT0. |
| 0986& AE 00 | 170 | | LDX | #0 ;START WITH BIT #0. |
| 0988& BF 00& | 171 | RAMADDR3 | STX | PADATA ;LOAD A PORT. |
| 098A& 38 00& | 172 | | LSL | PADATA ;PUT IN UPPER HALF |
| 098C& 38 00& | 173 | | LSL | PADATA ;OF PORT A. |
| 098E& 38 00& | 174 | | LSL | PADATA ; |
| 0990& 38 00& | 175 | | LSL | PADATA ; |
| 0992& B5 53& | 176 | | BIT | RAMDATAH;MASK OF OTHER BITS. |
| 0994& 27 02 | 177 | | BEQ | RAMADDR4;WAS ADDR BIT = 0? |
| 0996& 1E 00& | 178 | | BSET | 7,PADATA;NO, SET 259 DATA IN. |
| 0998& CD 090F& | 179 | RAMADDR4 | JSR | TOGL259H;LOAD 259 OUTPUT PIN. |
| 099B& 5C | 180 | | INCX | ;NEXT BIT NUMBER. |
| 099C& 48 | 181 | | LSLA | ;NEXT BIT WISE POS. |
| 099D& A3 07 | 182 | | CPX | #7 ; |
| 099F& 26 E7 | 183 | | BNE | RAMADDR3;ALL 7 BITS DONE? |
| 09A1& BD A3& | 184 | | JSR | REGLOAD ;LOAD X & A REGS. |
| 09A3& 81 | 185 | | RTS | ; |
| 09A4& BD 94& | 186 | RAMWRIT | JSR | REGSAVE |
| 09A6& CD 0941& | 187 | | JSR | RAMADDR |
| 09A9& A6 07 | 188 | | LDA | #7 |
| 09AB& B7 00& | 189 | | STA | PADATA |
| 09AD& CD 090F& | 190 | | JSR | TOGL259H |
| 09B0& BE 41& | 191 | | LDX | XSW |
| 09B2& 54 | 192 | | LSRX | |
| 09B3& 54 | 193 | | LSRX | |
| 09B4& 54 | 194 | | LSRX | |
| 09B5& 54 | 195 | | LSRX | |
| 09B6& 54 | 196 | | LSRX | |
| 09B7& 54 | 197 | | LSRX | |
| 09B8& E6 44& | 198 | | LDA | RAMDATA,X |
| 09BA& B7 00& | 199 | | STA | PADATA |
| 09BC& 11 01& | 200 | | BCLR | 0,PBDATA |
| 09BE& 10 01& | 201 | | BSET | 0,PBDATA |
| 09C0& A6 F0 | 202 | | LDA | #0F0H |
| 09C2& B7 00& | 203 | | STA | PADATA |
| 09C4& CD 090F& | 204 | | JSR | TOGL259H |
| 09C7& BD A3& | 205 | | JSR | REGLOAD |
| 09C9& 81 | 206 | | RTS | |
| 09CA& BD 94& | 207 | RAMREAD | JSR | REGSAVE |
| 09CC& CD 0941& | 208 | | JSR | RAMADDR |
| 09CF& BE 41& | 209 | | LDX | XSW |
| 09D1& 54 | 210 | | LSRX | |
| 09D2& 54 | 211 | | LSRX | |
| 09D3& 54 | 212 | | LSRX | |
| 09D4& 54 | 213 | | LSRX | |

```
09D5& 54           214           LSRX
09D6& 54           215           LSRX
09D7& 3F 04&       216           CLR     PADIR
09D9& 1B 01&       217           BCLR    5,PBDATA
09DB& 11 01&       218           BCLR    0,PBDATA
09DD& B6 00&       219           LDA     PADATA
09DF& E7 44&       220           STA     RAMDATA,X
09E1& 10 01&       221           BSET    0,PBDATA
09E3& 1A 01&       222           BSET    5,PBDATA
09E5& A6 FF        223           LDA     #0FFH
09E7& B7 04&       224           STA     PADIR
09E9& BD A3&       225           JSR     REGLOAD
09EB& 81           226           RTS
                   227
                    56           INCLUDE "INSOPTO.ASM" ; OPTO INPUT
                     1  $EJ
                     2  ;************* OPTO    *********************
                     3  ;*******************************************
                     4  ;
                     5  ;THIS SUBROUTINE WILL SET THE BRIGHTNESS
                     6  ;OF THE LED'S, TURN ON OR OFF ANY COMBINATION
                     7  ;OFF THE TWO LED'S, DELAY A SET TIME BEFORE
                     8  ;TAKING ANALOG READING, AND RETURN ANALOG
                     9  ;RESULT AND MEASUREMENT OF LED BEIGHTNESS.
                    10  ;
                    11  ;*******************************************
                    12  ;
                    13  ;   INPUT :
                    14  ;           A REGISTER CONTAINS THE LEVEL OF
                    15  ;           BRIGHTNESS THE LED'S ARE TO BE SET.
                    16  ;           X REGISTER CONTAINS THE AMOUNT OF
                    17  ;           TIME IN 1/16 SECONDS TO DELAY
                    18  ;           BEFORE TAKING THE READING.
                    19  ;           ANCOUNT HAS THE NUMBER OF ANALOG
                    20  ;           READINGS TO TAKE (AND AVERAGE).
                    21  ;
                    22  ;   OUTPUT :
                    23  ;           ANCOUNT IS THE RESULT OF THE
                    24  ;           ANALOG INPUT FROM THE PHOTO
                    25  ;           TRANSISTOR.
                    26  ;           LEDLVL IS A MEASUREMENT OF THE
                    27  ;           BRIGHTNESS OF THE LED'S.
                    28  ;
                    29  ;   REGISTERS SAVED (Y/N) : Y
                    30  ;   IF "N" ABOVE THEN REGISTERS USED
                    31  ;           (* = MODIFIED):
                    32  ;
                    33  ;   FIELDS USED (* = MODIFIED):
                    34  ;                 ANCOUNT
                    35  ;                *XDATAL
                    36  ;                *XDATAH
                    37  ;                *XSW      /BIT:2,6,7
                    38  ;                 HALTSW   /BIT:5,6
                    39  ;
                    40  ;   SUBROUTINES CALLED:
                    41  ;                 REGSAVE
                    42  ;                 REGLOAD
                    43  ;                 RAMADDR
                    44  ;                 LEDONG
                    45  ;                 LEDOFFG
                    46  ;                 LEDONR
                    47  ;                 LEDOFFR
                    48  ;                 TIMER
                    49  ;                 ADCINP
                    50  ;                 PTON
                    51  ;                 PTOFF
                    52  ;                 LEDBRIT
                    53  ;
                    54  ;*******************************************
09EC& BD 94&        55  OPTO     JSR     REGSAVE ;SAVE X & A REGS.
09EE& CD 0AE9&      56           JSR     PTON    ;TURN ON AUX POWER.
09F1& 0B 2D& 03     57           BRCLR   5,HALTSW,OPTO1;GREEN ON?
09F4& CD 0AB9&      58           JSR     LEDONG  ;YES, TURN GREEN ON.
```

```
09F7& 0D 2D& 03    59    OPTO1    BRCLR    6,HALTSW,OPTO2 ;RED ON?
09FA& CD 0AD1&     60             JSR      LEDONR   ;YES, TURN RED ON.
09FD& 1D 41&       61    OPTO2    BCLR     6,XSW    ;SET BRIGHTNESS
09FF& 1E 41&       62             BSET     7,XSW    ;LEVEL OF LED'S.
0A01& B7 52&       63             STA      XDATAL   ;
0A03& 3F 51&       64             CLR      XDATAH   ;
0A05& CD 0941&     65             JSR      RAMADDR  ;
0A08& 9F           66             TXA               ;PUT DELAY IN A REG.
0A09& 15 41&       67             BCLR     2,XSW    ;WAIT UNTIL FINISHED.
0A0B& CD 0900&     68             JSR      TIMER    ;GO TO TIMING PGM.
0A0E& AE 00        69             LDX      #0       ;SET FOR ANALOG CH1.
0A10& B6 2B&       70             LDA      ANCOUNT  ;A=NUMBER OF CONV.
0A12& CD 0A76&     71             JSR      ADCINP   ;DO CONVERSIONS.
0A15& CD 0A24&     72             JSR      LEDBRIT  ;READ LED LEVEL.
0A18& CD 0AF9&     73             JSR      PTOFF    ;TURN OFF AUX POWER.
0A1B& CD 0AC5&     74             JSR      LEDOFFG  ;TURN OFF GREEN LED.
0A1E& CD 0ADD&     75             JSR      LEDOFFR  ;TURN OFF RED LED.
0A21& BD A3&       76             JSR      REGLOAD  ;LOAD X & A REGS.
0A23& 81           77             RTS               ;
                   78    $EJ
                   79    ;************ LEDBRIT  ********************
                   80    ;*****************************************
                   81    ;
                   82    ;THIS SUBROUTINE WILL READ THE ANALOG
                   83    ;LEVEL WHICH INDICATES THE RELATIVE
                   84    ;BRIGHTNESS OF THE LED'S.
                   85    ;
                   86    ;*****************************************
                   87    ;
                   88    ;   INPUT : (NONE)
                   89    ;
                   90    ;   OUTPUT :
                   91    ;          LEDLVL IS THE ANALOG READING
                   92    ;          OF THE LED BRIGHTNESS.
                   93    ;
                   94    ;   REGISTERS SAVED (Y/N) : Y
                   95    ;   IF "N" ABOVE THEN REGISTERS USED
                   96    ;          (* = MODIFIED):
                   97    ;
                   98    ;   FIELDS USED (* = MODIFIED):
                   99    ;          *ANCOUNT
                   100   ;          *LEDLVL
                   101   ;
                   102   ;   SUBROUTINES CALLED:
                   103   ;          REGSAVE
                   104   ;          REGLOAD
                   105   ;          ADCINP
                   106   ;
                   107   ;*****************************************
0A24& BD 94&       108   LEDBRIT  JSR      REGSAVE  ;SAVE X & A REGS.
0A26& B6 2B&       109            LDA      ANCOUNT  ;SAVE PREVIOUS RESULT
0A28& B7 30&       110            STA      LEDLVL   ;IN LEDLVL FIELD.
0A2A& AE 02        111            LDX      #2       ;SET ANALOG CH3.
0A2C& A6 40        112            LDA      #64      ;DO 64 CONVERSIONS.
0A2E& CD 0A76&     113            JSR      ADCINP   ;DO CONVERSIONS.
0A31& B6 2B&       114            LDA      ANCOUNT  ;GET RESULT.
0A33& BE 30&       115            LDX      LEDLVL   ;GET OTHER RESULT.
0A35& BF 2B&       116            STX      ANCOUNT  ;PUT IT BACK.
0A37& B7 30&       117            STA      LEDLVL   ;STORE LED RESULT.
0A39& BD A3&       118            JSR      REGLOAD  ;LOAD X & A REGS.
0A3B& 81           119            RTS               ;
                   120   $EJ
                   121   ;************ TEMPRD   ********************
                   122   ;*****************************************
                   123   ;
                   124   ;THIS SUBROUTINE WILL READ THE AMBIENT
                   125   ;TEMPERATURE FROM THE THERMISTOR IN THE
                   126   ;INSTRUMENT.
                   127   ;
                   128   ;*****************************************
                   129   ;
                   130   ;   INPUT : (NONE)
                   131   ;
                   132   ;   OUTPUT :
```

```
133        ;              TEMP HAS THE BINARY NUMBER WHICH
134        ;              INDICATES THE CURRENT TEMPERATURE.
135        ;
136        ;    REGISTERS SAVED (Y/N) : Y
137        ;    IF "N" ABOVE THEN REGISTERS USED
138        ;              (* = MODIFIED):
139        ;
140        ;    FIELDS USED (* = MODIFIED):
141        ;              *XSW       /BIT:2
142        ;              ANCOUNT
143        ;              *TEMP
144        ;
145        ;    SUBROUTINES CALLED:
146        ;              REGSAVE
147        ;              REGLOAD
148        ;              PTON
149        ;              PTOFF
150        ;              TIMER
151        ;              ADCINP
152        ;
153        ;********************************************
```

| | | | | |
|---|---|---|---|---|
| 0A3C& BD 94& | 154 | TEMPRD | JSR | REGSAVE ;SAVE X & A REGS. |
| 0A3E& CD 0AE9& | 155 | | JSR | PTON    ;TURN ON AUX POWER. |
| 0A41& A6 04 | 156 | | LDA | #4      ;WAIT FOR 4/16 |
| 0A43& 15 41& | 157 | | BCLR | 2,XSW   ;OF A SECOND. |
| 0A45& CD 0900& | 158 | | JSR | TIMER   ; |
| 0A48& AE 01 | 159 | | LDX | #1      ;SET TO ANALOG CH2. |
| 0A4A& A6 40 | 160 | | LDA | #64     ;DO CONV 64 TIMES. |
| 0A4C& CD 0A76& | 161 | | JSR | ADCINP  ;DO CONVERSIONS. |
| 0A4F& B6 2B& | 162 | | LDA | ANCOUNT ;GET RESULT. |
| 0A51& B7 2F& | 163 | | STA | TEMP    ;STORE IT. |
| 0A53& CD 0AF9& | 164 | | JSR | PTOFF   ;TURN OFF AUX POWER. |
| 0A56& BD A3& | 165 | | JSR | REGLOAD ;LOAD X & A REGS. |
| 0A58& 81 | 166 | | RTS | ; |

```
167        $EJ
168        ;************* BATTRD   ********************
169        ;********************************************
170        ;
171        ;THIS SUBROUTINE WILL READ THE BATTERY
172        ;VOLTAGE OF THE INSTRUMENT.
173        ;
174        ;********************************************
175        ;
176        ;    INPUT : (NONE)
177        ;
178        ;    OUTPUT :
179        ;         BATTVOLT IS THE BINARY NUMBER WHICH
180        ;         IS RELATED TO THE ACTUAL BATTERY
181        ;         VOLTAGE IN THE INSTRUMENT.
182        ;
183        ;    REGISTERS SAVED (Y/N) : Y
184        ;    IF "N" ABOVE THEN REGISTERS USED
185        ;              (* = MODIFIED):
186        ;
187        ;    FIELDS USED (* = MODIFIED):
188        ;              *XSW       /BIT:2
189        ;              ANCOUNT
190        ;              *BATTVOLT
191        ;
192        ;    SUBROUTINES CALLED:
193        ;              REGSAVE
194        ;              REGLOAD
195        ;              PTON
196        ;              PTOFF
197        ;              TIMER
198        ;              ADCINP
199        ;
200        ;********************************************
```

| | | | | |
|---|---|---|---|---|
| 0A59& BD 94& | 201 | BATTRD | JSR | REGSAVE ;SAVE X & A REGS. |
| 0A5B& CD 0AE9 | 202 | | JSR | PTON    ;TURN ON AUX POWER. |
| 0A5E& A6 04 | 203 | | LDA | #4      ;WAIT FOR |
| 0A60& 15 41& | 204 | | BCLR | 2,XSW   ;4/16 OF A SECOND. |

```
0A62& CD 0900&    205            JSR     TIMER    ;
0A65& A6 03       206            LDA     #3       ;SET FOR ANALOG CH4.
0A67& A6 40       207            LDA     #64      ;DO CONV 64 TIMES.
0A69& CD 0A76&    208            JSR     ADCINP   ;DO CONVERSIONS.
0A6C& B6 2B&      209            LDA     ANCOUNT  ;GET RESULT.
0A6E& B7 2E&      210            STA     BATTVOLT ;STORE IT.
0A70& CD 0AF9&    211            JSR     PTOFF    ;TURN OFF AUX POWER.
0A73& BD A3&      212            JSR     REGLOAD  ;LOAD X & A REGS.
0A75& 81          213            RTS              ;
                  214    $EJ
                  215    ;************* ADCINP   *********************
                  216    ;************* ADCINT   *********************
                  217    ;************* ADCCNV   *********************
                  218    ;********************************************
                  219    ;
                  220    ;THESE SUBROUTINES DO CONVERSIONS, HANDLE
                  221    ;ADC INTERRUPTS, AND SET THE THE CONVERSION
                  222    ;BIT IN THE ADC.
                  223    ;
                  224    ;********************************************
                  225    ;
                  226    ;   INPUT :
                  227    ;            A REGISTER CONTAINS THE NUMBER
                  228    ;            OF CONVERSIONS TO PERFORM.
                  229    ;            X REGISTER CONTAINS THE ADC
                  230    ;            CHANNEL NUMBER TO READ.
                  231    ;
                  232    ;
                  233    ;   OUTPUT :
                  234    ;            ANCOUNT IS THE AVERAGED RESULT OF
                  235    ;            THE ANALOG CONVERSIONS WHICH IS
                  236    ;            ROUNDED.
                  237    ;
                  238    ;   REGISTERS SAVED (Y/N) : Y
                  239    ;   IF "N" ABOVE THEN REGISTERS USED
                  240    ;            (* = MODIFIED):
                  241    ;
                  242    ;   FIELDS USED (* = MODIFIED):
                  243    ;                   *ANCOUNT
                  244    ;                   *ADCCTRL
                  245    ;                   *ADCDATA
                  246    ;                   *DISPWORD
                  247    ;
                  248    ;   SUBROUTINES CALLED:
                  249    ;                   REGSAVE
                  250    ;                   REGLOAD
                  251    ;                   ADCCNV
                  252    ;
                  253    ;********************************************
0A76& BD 94&      254    ADCINP   JSR     REGSAVE  ;SAVE X & A REGS.
0A78& BF 0F&      255             STX     ADCCTRL  ;LOAD CHANNEL #.
0A7A& 1C 0F&      256             BSET    6,ADCCTRL;DISABLE INTERRUPT.
0A7C& B7 2B&      257             STA     ANCOUNT  ;STORE # OF CONV.
0A7E& 97          258             TAX              ;PUT A IN X.
0A7F& 3F 47&      259             CLR     DISPWORD ;ZERO OUT RESULT
0A81& 3F 48&      260             CLR     DISPWORD+1;FIELD.
0A83& CD 0AB3&    261    ADCINP1  JSR     ADCCNV   ;DO A CONVERSION.
0A86& B6 0E&      262             LDA     ADCDATA  ;LOAD RESULT.
0A88& BB 48&      263             ADD     DISPWORD+1;ADD TO LOW BYTE.
0A8A& 24 02       264             BCC     ADCINP2  ;PASSED #0FFH?
0A8C& 3C 47&      265             INC     DISPWORD ;YES, HIGH=HIGH+1.
0A8E& B7 48&      266    ADCINP2  STA     DISPWORD+1;STORE LOW BYTE.
0A90& 5A          267             DECX             ;#CONV=#CONV-1.
0A91& 26 F0       268             BNE     ADCINP1  ;DONE WITH CONV?
0A93& AE 00       269             LDX     #0       ;YES, X IS COUNTER.
0A95& B6 48&      270             LDA     DISPWORD+1;GET LOW BYTE.
0A97& B0 2B&      271    ADCINP3  SUB     ANCOUNT  ;SUB #CONV TO AVG.
0A99& 24 04       272             BCC     ADCINP4  ;LOW BYTE < 0?
0A9B& 3A 47&      273             DEC     DISPWORD ;YES, HIGH=HIGH-1.
0A9D& 2B 03       274             BMI     ADCINP5  ;HIGH BYTE < 0?
0A9F& 5C          275    ADCINP4  INCX             ;ADD 1 TO RESULT.
0AA0& 20 F5       276             BRA     ADCINP3  ;DO AGAIN.
```

```
0AA2& 40           277           ADCINP5    NEGA                ;GET REMAINDER.
0AA3& B7 48&       278                      STA    DISPWORD+1   ;STORE IT.
0AA5& B6 2B&       279                      LDA    ANCOUNT      ;LOAD # OF CONV.
0AA7& 44           280                      LSRA                ;DIVIDE BY 2.
0AA8& B0 48&       281                      SUB    DISPWORD+1   ;SUBTRACT REM.
0AAA& 24 01        282                      BCC    ADCINP6      ;REM < 1/2 OF #CONV?
0AAC& 5C           283                      INCX                ;NO, ROUND UP.
0AAD& BF 2B&       284           ADCINP6    STX    ANCOUNT      ;STORE AVERAGED #.
0AAF& BD A3&       285                      JSR    REGLOAD      ;LOAD X & A REGS.
0AB1& 81           286                      RTS                 ;
0AB2& 80           287           ADCINT     RTI                 ;DUMMY INTERRUPT.
0AB3& 1A 0F&       288           ADCCNV     BSET   5,ADCCTRL    ;START CONVERSION.
0AB5& 0A 0F& FD    289           ADCCNV1    BRSET  5,ADCCTRL,ADCCNV1;WAIT.
0AB8& 81           290                      RTS                 ;
                   291           $EJ
                   292           ;************* LEDONG  ********************
                   293           ;************* LEDOFFG *********************
                   294           ;************* LEDONR  *********************
                   295           ;************* LEDOFFR *********************
                   296           ;*******************************************
                   297           ;
                   298           ;THESE SUBROUTINES TURN THE LED'S ON AND
                   299           ;OFF.
                   300           ;
                   301           ;*******************************************
                   302           ;
                   303           ;   INPUT : (NONE)
                   304           ;
                   305           ;   OUTPUT : (NONE)
                   306           ;
                   307           ;   REGISTERS SAVED (Y/N) : N
                   308           ;   IF "N" ABOVE THEN REGISTERS USED
                   309           ;           (* = MODIFIED):
                   310           ;
                   311           ;   FIELDS USED (* = MODIFIED):
                   312           ;            *PADATA
                   313           ;
                   314           ;   SUBROUTINES CALLED:
                   315           ;            TOGL259H
                   316           ;
                   317           ;*******************************************
0AB9& 19 00&       318           LEDONG     BCLR   4,PADATA;SET 259-2 OUTPUT Q6
0ABB& 1A 00&       319                      BSET   5,PADATA;TO LOW LEVEL.
0ABD& 1C 00&       320                      BSET   6,PADATA;MAKES P-CHANNEL
0ABF& 1F 00&       321                      BCLR   7,PADATA;MOSFET TURN ON.
0AC1& CD 090F&     322                      JSR    TOGL259H;GATE INTO 259-2.
0AC4& 81           323                      RTS             ;
0AC5& 19 00&       324           LEDOFFG    BCLR   4,PADATA;SET 259-2 OUTPUT Q6
0AC7& 1A 00&       325                      BSET   5,PADATA;TO HIGH LEVEL.
0AC9& 1C 00&       326                      BSET   6,PADATA;MAKES P-CHANNEL
0ACB& 1E 00&       327                      BSET   7,PADATA;MOSFET TURN OFF.
0ACD& CD 090F&     328                      JSR    TOGL259H;GATE INTO 259-2.
0AD0& 81           329                      RTS             ;
0AD1& 18 00&       330           LEDONR     BSET   4,PADATA;SET 259-2 OUTPUT Q7
0AD3& 1A 00&       331                      BSET   5,PADATA;TO LOW LEVEL.
0AD5& 1C 00&       332                      BSET   6,PADATA;MAKES P-CHANNEL
0AD7& 1F 00&       333                      BCLR   7,PADATA;MOSFET TURN ON.
0AD9& CD 090F&     334                      JSR    TOGL259H;GATE INTO 259-2.
0ADC& 81           335                      RTS             ;
0ADD& 18 00&       336           LEDOFFR    BSET   4,PADATA;SET 259-2 OUTPUT Q7
0ADF& 1A 00&       337                      BSET   5,PADATA;TO HIGH LEVEL.
0AE1& 1C 00&       338                      BSET   6,PADATA;MAKES P-CHANNEL
0AE3& 1E 00&       339                      BSET   7,PADATA;MOSFET TURN OFF.
0AE5& CD 090F&     340                      JSR    TOGL259H;GATE INTO 259-2
0AE8& 81           341                      RTS             ;
                   342           $EJ
                   343           ;************* PTON  ***********************
                   344           ;************* PTOFF ***********************
                   345           ;*******************************************
                   346           ;
                   347           ;THESE SUBROUTINES TURN THE AUXILLIARY
                   348           ;POWER FOR BOTH THE V+ AND V- RAILS ON
```

```
                                       349       ;AND OFF.
                                       350       ;
                                       351       ;************************************
                                       352       ;
                                       353       ;   INPUT : (NONE)
                                       354       ;
                                       355       ;   OUTPUT : (NONE)
                                       356       ;
                                       357       ;   REGISTERS SAVED (Y/N) : N
                                       358       ;   IF "N" ABOVE THEN REGISTERS USED
                                       359       ;             (* = MODIFIED):
                                       360       ;
                                       361       ;   FIELDS USED (* = MODIFIED):
                                       362       ;                *PBDATA
                                       363       ;                *XSW      /BIT:6,7
                                       364       ;                *XDATAL
                                       365       ;                *XDATAH
                                       366       ;
                                       367       ;   SUBROUTINES CALLED:
                                       368       ;                RAMADDR
                                       369       ;
                                       370       ;************************************
OAE9&  1D 41&                          371       PTON    BCLR    6,XSW     ;MAKE SURE LED LEVELS
OAEB&  1E 41&                          372               BSET    7,XSW     ;ARE SET TO LOWEST
OAED&  3F 52&                          373               CLR     XDATAL    ;POWER.
OAEF&  3F 51&                          374               CLR     XDATAH    ;
OAF1&  CD 0941&                        375               JSR     RAMADDR   ;
OAF4&  18 01&                          376               BSET    4,PBDATA  ;TURN ON V-.
OAF6&  1F 01&                          377               BCLR    7,PBDATA  ;TURN ON V+.
OAF8&  81                              378               RTS               ;
OAF9&  1E 01&                          379       PTOFF   BSET    7,PBDATA  ;TURN OFF V+.
OAFB&  19 01&                          380               BCLR    4,PBDATA  ;TURN OFF V-.
OAFD&  81                              381               RTS               ;
                                       382
                                        57                INCLUDE "INS8250.ASM" ; SERIAL I/O
                                         1       $EJ
                                         2       ;************ RST8250 ********************
                                         3       ;************************************
                                         4       ;
                                         5       ;THIS SUBROUTINE WILL INITIALIZE ALL FUNCTIONS
                                         6       ;OF THE INS8250 SERIAL I/O CHIP WHICH IS
                                         7       ;ATACHED VIA THE "PRINTER CONNECTOR".
                                         8       ;
                                         9       ;************************************
                                        10       ;
                                        11       ;   INPUT : (NONE)
                                        12       ;
                                        13       ;   OUTPUT : (NONE)
                                        14       ;
                                        15       ;   REGISTERS SAVED (Y/N) : Y
                                        16       ;   IF "N" ABOVE THEN REGISTERS USED
                                        17       ;             (* = MODIFIED):
                                        18       ;
                                        19       ;   FIELDS USED (* = MODIFIED):
                                        20       ;                *ADDR8250
                                        21       ;                *DATA8250
                                        22       ;                 TIKSEC
                                        23       ;
                                        24       ;   SUBROUTINES CALLED:
                                        25       ;                REGSAVE
                                        26       ;                REGLOAD
                                        27       ;                WR8250
                                        28       ;                RD8250
                                        29       ;
                                        30       ;************************************
OAFE&  BD 94&                           31       RST8250  JSR    REGSAVE   ;SAVE X & A REGS.
OB00&  A6 03                            32                LDA    #3        ;INITIALIZE LINE
OB02&  B7 3F&                           33                STA    ADDR8250  ;CONTROL REGISTER TO
OB04&  A6 83                            34                LDA    #83H      ;8 BITS, NO PARITY,
OB06&  B7 40&                           35                STA    DATA8250  ;1 STOP BIT & ENABLE
OB08&  CD 0B94&                         36                JSR    WR8250    ;BAUD RATE REGISTER.
OB0B&  3F 3F&                           37                CLR    ADDR8250  ;SET BAUD RATE TO
```

```
0B0D& A6 0C        38            LDA    #0CH       ;9600 BITS PER
0B0F& B7 40&       39            STA    DATA8250   ;SECOND WITH A
0B11& CD 0B94&     40            JSR    WR8250     ;1.8432 mHZ CRYSTAL
0B14& A6 01        41            LDA    #1         ;SET INTERRUPT
0B16& B7 3F&       42            STA    ADDR8250   ;ENABLE REGISTER TO
0B18& 3F 40&       43            CLR    DATA8250   ;DISABLE ALL
0B1A& CD 0B94&     44            JSR    WR8250     ;INTERRUPTS.
0B1D& A6 03        45            LDA    #3         ;SET LINE CONTROL
0B1F& B7 3F&       47            STA    ADDR8250   ;REGISTER TO 8 BITS
0B21& B7 40&       48            STA    DATA8250   ;NO PARITY, 1 STOP
0B23& CD 0B94&     49            JSR    WR8250     ;BIT & R/W ENABLED
0B26& B6 4A&       50            LDA    TIKSEC     ;SET TIME OUT TO
0B28& AB 03        51            ADD    #3         ;OCCUR IN 3 TIME
0B2A& A1 3C        52            CMP    #60        ;BASE INT'S, 2-3
0B2C& 25 02        53            BCS    RST82501   ;SECONDS.
0B2E& A0 3C        54            SUB    #60        ;
0B30& AE 05        55    RST82501 LDX   #5         ;READ LINE STATUS
0B32& BF 3F&       56            STX    ADDR8250   ;REGISTER & BRANCH
0B34& CD 0B51&     57            JSR    RD8250     ;IF NO DATA READY.
0B37& 01 40& 09    58            BRCLR  0,DATA8250,RST82502
0B3A& 3F 3F&       59            CLR    ADDR8250   ;READ INCOMING
0B3C& CD 0B51&     60            JSR    RD8250     ;CHARACER.
0B3F& B1 4A&       61            CMP    TIKSEC     ;IF NO TIME OUT
0B41& 26 ED        62            BNE    RST82501   ;THEN DO IT AGAIN.
0B43& A6 04        63    RST82502 LDA   #4         ;SET MODEM CONTROL
0B45& B7 3F&       64            STA    ADDR8250   ;REGISTER TO NO
0B47& 3F 40&       65            CLR    DATA8250   ;OUTPUTS ENABLED.
0B49& CD 0B94&     66            JSR    WR8250     ;
0B4C& 3F 3F&       67            CLR    ADDR8250   ;SET ADDRESS TO 0.
0B4E& BD A3&       68            JSR    REGLOAD    ;LOAD X & A REGS.
0B50& 81           69            RTS               ;
                   70    $EJ
                   71    ;************** RD8250  *********************
                   72    ;********************************************
                   73    ;
                   74    ;THIS SUBROUTINE WILL READ THE DATA FROM ANY
                   75    ;PORT IN THE 8250  CHIP.
                   76    ;
                   77    ;********************************************
                   78    ;
                   79    ;   INPUT :
                   80    ;          ADDR8250 /ADDRESS OF PORT
                   81    ;
                   82    ;   OUTPUT :
                   83    ;            DATA8250 /DATA READ
                   84    ;
                   85    ;   REGISTERS SAVED (Y/N) : Y
                   86    ;   IF "N" ABOVE THEN REGISTERS USED
                   87    ;             (* = MODIFIED):
                   88    ;
                   89    ;   FIELDS USED (* = MODIFIED):
                   90    ;               *DATA8250
                   91    ;               *PADIR
                   92    ;               *PADATA
                   93    ;               *PBDATA    /BIT:3
                   94    ;
                   95    ;   SUBROUTINES CALLED:
                   96    ;               REGSAVE
                   97    ;               REGLOAD
                   98    ;               ADR8250
                   99    ;               TOGL259H
                  100    ;
                  101    ;********************************************
0B51& BD 94&      102    RD8250   JSR   REGSAVE    ;SAVE X & A REGS.
0B53& CD 0B77&    103            JSR    ADR8250    ;SET PORT ADDRESS.
0B56& A6 30       104            LDA    #30H       ;SET 8250 RD LINE
0B58& B7 00&      105            STA    PADATA     ;LOW (259-2 Q3).
0B5A& CD 090F&    106            JSR    TOGL259H   ;
0B5D& A6 00       107            LDA    #0         ;SET MPU PORT A
0B5F& B7 04&      108            STA    PADIR      ;TO INPUT.
0B61& 17 01&      109            BCLR   3,PBDATA   ;8250 CHIP SEL LOW.
0B63& B6 00&      110            LDA    PADATA     ;INPUT DATA FROM
```

```
0B65& B7 40&        111              STA    DATA8250;8250 & STORE IT.
0B67& 16 01&        112              BSET   3,PBDATA;8250 CHIP SEL HIGH.
0B69& A6 FF         113              LDA    #0FFH    ;SET MPU PORT A
0B6B& B7 04&        114              STA    PADIR    ;TO OUTPUT.
0B6D& A6 B0         115              LDA    #0B0H    ;SET 8250 RD LINE
0B6F& B7 00&        116              STA    PADATA   ;HIGH (259-2 Q3)
0B71& CD 090F&      117              JSR    TOGL259H;
0B74& BD A3&        118              JSR    REGLOAD  ;LOAD X & A REGS.
0B76& 81            119              RTS             ;
                    120      $EJ
                    121      ;************* ADR8250   ********************
                    122      ;********************************************
                    123      ;
                    124      ;THIS SUBROUTINE WILL SET THE 8250 PORT
                    125      ;ADDRESS (A0-A2).
                    126      ;
                    127      ;********************************************
                    128      ;
                    129      ;   INPUT :
                    130      ;          ADDR8250 /ADDRESS OF PORT
                    131      ;
                    132      ;   OUTPUT : (NONE)
                    133      ;
                    134      ;   REGISTERS SAVED (Y/N) : N
                    135      ;   IF "N" ABOVE THEN REGISTERS USED
                    136      ;             (* = MODIFIED):
                    137      ;                 * A REGISTER
                    138      ;                 * X REGISTER
                    139      ;
                    140      ;   FIELDS USED (* = MODIFIED):
                    141      ;              ADDR8250
                    142      ;              *PADATA
                    143      ;
                    144      ;   SUBROUTINES CALLED:
                    145      ;              TOGL259H
                    146      ;
                    147      ;********************************************
0B77& BE 3F&        148      ADR8250 LDX    ADDR8250;SAVE ADDRESS IN X.
0B79& A6 00         149              LDA    #0       ;START AT 259-2 Q0.
0B7B& B7 00&        150      ADR82501 STA   PADATA   ;OUTPUT 259 ADDRESS.
0B7D& 00 3F& 04     151              BRSET  0,ADDR8250,ADR82502
0B80& 1F 00&        152              BCLR   7,PADATA;ADDRESS BIT = 0.
0B82& 20 02         153              BRA    ADR82503;OUTPUT IT.
0B84& 1E 00&        154      ADR82502 BSET  7,PADATA;ADDRESS BIT = 1.
0B86& CD 090F&      155      ADR82503 JSR   TOGL259H;WRITE ADDRESS BIT.
0B89& 34 3F&        156              LSR    ADDR8250;SHIFT FOR NEXT BIT.
0B8B& AB 10         157              ADD    #10H     ;NEXT 259-2 ADDRESS.
0B8D& A1 30         158              CMP    #30H     ;A0, A1, & A2
0B8F& 26 EA         159              BNE    ADR82501;DONE?
0B91& BF 3F&        160              STX    ADDR8250;RESTORE 8250 ADDR.
0B93& 81            161              RTS             ;
                    162      $EJ
                    163      ;************* WR8250    ********************
                    164      ;********************************************
                    165      ;
                    166      ;THIS SUBROUTINE WILL WRITE DATA TO ANY PORT
                    167      ;IN THE 8250 CHIP.
                    168      ;
                    169      ;********************************************
                    170      ;
                    171      ;   INPUT :
                    172      ;          ADDR8250 /ADDRESS OF PORT
                    173      ;          DATA8250 /DATA TO BE WRITTEN
                    174      ;
                    175      ;   OUTPUT : (NONE)
                    176      ;
                    177      ;   REGISTERS SAVED (Y/N) : Y
                    178      ;   IF "N" ABOVE THEN REGISTERS USED
                    179      ;             (* = MODIFIED):
                    180      ;
                    181      ;   FIELDS USED (* = MODIFIED):
                    182      ;              DATA8250
                    183      ;              *PADATA
```

```
                            184     ;
                            185     ;    SUBROUTINES CALLED:
                            186     ;                  REGSAVE
                            187     ;                  REGLOAD
                            188     ;                  ADR8250
                            189     ;                  TOGL259H
                            190     ;
                            191     ;*******************************************
0B94& BD 94&                192     WR8250    JSR      REGSAVE  ;SAVE X & A REGS.
0B96& CD 0B77&              193               JSR      ADR8250  ;SET 8250 ADDRESS.
0B99& A6 40                 194               LDA      #40H     ;SET 8250 WR LINE
0B9B& B7 00&                195               STA      PADATA   ;(259-2 Q4) LOW.
0B9D& CD 090F&              196               JSR      TOGL259H;
0BA0& B6 40&                197               LDA      DATA8250 ;OUTPUT DATA.
0BA2& B7 00&                198               STA      PADATA   ;
0BA4& 17 01&                199               BCLR     3,PBDATA ;8250 CS = LOW.
0BA6& 16 01&                200               BSET     3,PBDATA ;8250 CS = HIGH.
0BA8& A6 C0                 201               LDA      #0C0H    ;SET 8250 WR LINE
0BAA& B7 00&                202               STA      PADATA   ;(259-2 Q4) HIGH.
0BAC& CD 090F&              203               JSR      TOGL259H;
0BAF& BD A3&                204               JSR      REGLOAD  ;LOAD X & A REGS.
0BB1& 81                    205               RTS               ;
                            206     $EJ
                            207     ;************* CHK8250  ********************
                            208     ;*******************************************
                            209     ;
                            210     ;THIS SUBROUTINE WILL CHECK TO SEE IF AN
                            211     ;8250 CHIP IS ATTACHED TO THE PRINTER
                            212     ;CONNECTOR.
                            213     ;
                            214     ;*******************************************
                            215     ;
                            216     ;   INPUT : (NONE)
                            217     ;
                            218     ;   OUTPUT :
                            219     ;           ADDR8250 (IF BIT 3 HIGH THEN
                            220     ;                    NO 8250 ATTACHED)
                            221     ;
                            222     ;   REGISTERS SAVED (Y/N) : Y
                            223     ;   IF "N" ABOVE THEN REGISTERS USED
                            224     ;           (* = MODIFIED):
                            225     ;
                            226     ;   FIELDS USED (* = MODIFIED):
                            227     ;                  *DATA8250
                            228     ;                  *ADDR8250
                            229     ;                   PCDATA
                            230     ;
                            231     ;   SUBROUTINES CALLED:
                            232     ;                  REGSAVE
                            233     ;                  REGLOAD
                            234     ;                  RD8250
                            235     ;                  WR8250
                            236     ;
                            237     ;*******************************************
0BB2& BD 94&                238     CHK8250   JSR      REGSAVE  ;SAVE X & A REGS.
0BB4& 01 02& 02             239               BRCLR    0,PCDATA,CHK8250A
0BB7& 20 16                 240               BRA      CHK8250B ;SENSE NOT LOW.
0BB9& A6 07                 241     CHK8250A  LDA      #7       ;WRITE #0DH IN 8250
0BBB& B7 3F&                242               STA      ADDR8250 ;SCRATCH REGISTER.
0BBD& A6 0D                 243               LDA      #0DH     ;
0BBF& B7 40&                244               STA      DATA8250;
0BC1& CD 0B94&              245               JSR      WR8250   ;
0BC4& CD 0B51&              246               JSR      RD8250   ;READ BACK SCRATCH.
0BC7& B1 40&                247               CMP      DATA8250;
0BC9& 26 04                 248               BNE      CHK8250B ;DATA READ = WRITTEN?
0BCB& 3F 3F&                249               CLR      ADDR8250 ;OK, 8250 PRESENT.
0BCD& 20 04                 250               BRA      CHK8250C ;GO TO END OF SUBR.
0BCF& A6 08                 251     CHK8250B  LDA      #08      ;SET BIT IN ADDR8250
0BD1& B7 3F&                252               STA      ADDR8250 ;TO INDICATE NO CHIP.
0BD3& BD A3&                253     CHK8250C  JSR      REGLOAD  ;LOAD X & A REGS.
0BD5& 81                    254               RTS
                            255     $EJ
```

```
                                256        ;************ INP8250  ********************
                                257        ;******************************************
                                258        ;
                                259        ;THIS SUBROUTINE WILL READ A CHARACTER FROM
                                260        ;THE SERIAL INTERFACE.
                                261        ;
                                262        ;******************************************
                                263        ;
                                264        ;   INPUT : (NONE)
                                265        ;
                                266        ;   OUTPUT :
                                267        ;           DATA8250 (CHARACTER READ)
                                268        ;           ADDR8250 (RETURN CODE FOR I/O)
                                269        ;
                                270        ;   REGISTERS SAVED (Y/N) : Y
                                271        ;   IF "N" ABOVE THEN REGISTERS USED
                                272        ;           (* = MODIFIED):
                                273        ;
                                274        ;   FIELDS USED (* = MODIFIED):
                                275        ;                   *DATA8250
                                276        ;                   *ADDR8250
                                277        ;                    TIKSEC
                                278        ;
                                279        ;   SUBROUTINES CALLED:
                                280        ;                    REGSAVE
                                281        ;                    REGLOAD
                                282        ;                    RD8250
                                283        ;                    WR8250
                                284        ;
                                285        ;******************************************
OBD6&  BD 94&                   286        INP8250  JSR    REGSAVE ;SAVE X & A REGS.
OBD8&  B6 4A&                   287                 LDA    TIKSEC  ;SET TIME OUT TO
OBDA&  AB 03                    288                 ADD    #3      ;2-3 SECONDS.
OBDC&  A1 3C                    289                 CMP    #60     ;
OBDE&  25 02                    290                 BCS    INP8250A;
OBE0&  A0 3C                    291                 SUB    #60
OBE2&  97                       292        INP8250A TAX            ;TIME OUT VALUE TO X.
OBE3&  01 02& 06                293        INP8250L BRCLR  0,PCDATA,INP8250B
OBE6&  A6 08                    294                 LDA    #08     ;SENSE NOT LOW, SET
OBE8&  B7 3F&                   295                 STA    ADDR8250;BIT 3 IN ADDR8250.
OBEA&  20 42                    296                 BRA    INP8250G;EXIT.
OBEC&  A6 05                    297        INP8250B LDA    #5      ;SEE IF DATA IS READY
OBEE&  B7 3F&                   298                 STA    ADDR8250;IN 8250.
OBF0&  CD 0B51&                 299                 JSR    RD8250  ;
OBF3&  B6 40&                   300                 LDA    DATA8250;
OBF5&  A4 0F                    301                 AND    #0FH    ;
OBF7&  27 22                    302                 BEQ    INP8250F;NO DATA, NO ERRORS.
OBF9&  07 40& 06                303                 BRCLR  3,DATA8250,INP8250C
OBFC&  A6 80                    304                 LDA    #80H    ;FRAMING ERROR.
OBFE&  B7 3F&                   305                 STA    ADDR8250;SET BIT IN ADDR8250.
0C00&  20 2C                    306                 BRA    INP8250G;EXIT.
0C02&  05 40& 06                307        INP8250C BRCLR  2,DATA8250,INP8250D
0C05&  A6 40                    308                 LDA    #40H    ;PARITY ERROR.
0C07&  B7 3F&                   309                 STA    ADDR8250;SET BIT IN ADDR8250.
0C09&  20 23                    310                 BRA    INP8250G;EXIT.
0C0B&  03 40& 06                311        INP8250D BRCLR  1,DATA8250,INP8250E
0C0E&  A6 20                    312                 LDA    #20H    ;OVERRUN ERROR.
0C10&  B7 3F&                   313                 STA    ADDR8250;SET BIT IN ADDR8250.
0C12&  20 1A                    314                 BRA    INP8250G;EXIT.
0C14&  3F 3F&                   315        INP8250E CLR    ADDR8250;DATA READY BIT SET.
0C16&  CD 0B51&                 316                 JSR    RD8250  ;READ CHARACTER.
0C19&  20 13                    317                 BRA    INP8250G;EXIT.
0C1B&  A6 01                    318        INP8250F LDA    #1      ;MAKE DATA TERMINAL
0C1D&  B7 40&                   319                 STA    DATA8250;READY LINE ACTIVE.
0C1F&  A6 04                    320                 LDA    #4      ;
0C21&  B7 3F&                   321                 STA    ADDR8250;
0C23&  CD 0B94&                 322                 JSR    WR8250  ;
0C26&  B3 4A&                   323                 CPX    TIKSEC  ;I/O TIMEOUT?
0C28&  26 B9                    324                 BNE    INP8250L;
0C2A&  A6 10                    325                 LDA    #10H    ;I/O TIME OUT.
0C2C&  B7 3F&                   326                 STA    ADDR8250;SET BIT IN ADDR8250.
0C2E&  BE 3F&                   327        INP8250G LDX    ADDR8250;SAVE I/O RC IN X.
```

```
0C30& A6 04       328                LDA     #4       ;MAKE DATA TERMINAL
0C32& B7 3F&      329                STA     ADDR8250;READY LINE INACTIVE..
0C34& B6 40&      330                LDA     DATA8250;SAVE DATA8250 IN A.
0C36& 3F 40&      331                CLR     DATA8250;DTR BIT OFF.
0C38& CD 0B94&    332                JSR     WR8250   ;
0C3B& B7 40&      333                STA     DATA8250;RESTORE DATA8250.
0C3D& BF 3F&      334                STX     ADDR8250;RESTORE ADDR8250.
0C3F& BD A3&      335                JSR     REGLOAD ;LOAD X & A REGS.
0C41& 81          336                RTS              ;
                  337      $EJ
                  338      ;************* OUT8250   *********************
                  339      ;*******************************************
                  340      ;
                  341      ;THIS SUBROUTINE WILL WRITE A CHARACTER TO
                  342      ;THE SERIAL INTERFACE.
                  343      ;
                  344      ;*******************************************
                  345      ;
                  346      ;   INPUT :
                  347      ;          DATA8250 (CHARACTER READ)
                  348      ;
                  349      ;   OUTPUT :
                  350      ;          ADDR8250 (RETURN CODE FOR I/O)
                  351      ;
                  352      ;   REGISTERS SAVED (Y/N) : Y
                  353      ;   IF "N" ABOVE THEN REGISTERS USED
                  354      ;          (* = MODIFIED):
                  355      ;
                  356      ;   FIELDS USED (* = MODIFIED):
                  357      ;              DATA8250
                  358      ;              *ADDR8250
                  359      ;              TIKSEC
                  360      ;
                  361      ;   SUBROUTINES CALLED:
                  362      ;              REGSAVE
                  363      ;              REGLOAD
                  364      ;              RD8250
                  365      ;              WR8250
                  366      ;
                  367      ;*******************************************
0C42& BD 94&      368      OUT8250   JSR     REGSAVE ;SAVE X & A REGS.
0C44& B6 4A&      369                LDA     TIKSEC  ;SET TIME OUT TO
0C46& AB 03       370                ADD     #3      ;2-3 SECONDS.
0C48& A1 3C       371                CMP     #60      ;
0C4A& 25 02       372                BCS     OUT8250A;
0C4C& A0 3C       373                SUB     #60      ;
0C4E& 97          374      OUT8250A  TAX             ;PUT TIME OUT IN X.
0C4F& 01 02& 06   375      OUT8250L  BRCLR   0,PCDATA,OUT8250B
0C52& A6 08       376                LDA     #08      ;SENSE NOT LOW.
0C54& B7 3F&      377                STA     ADDR8250;SET BIT IN ADDR8250..
0C56& 20 1F       378                BRA     OUT8250D;EXIT.
0C58& A6 06       379      OUT8250B  LDA     #6       ;CHECK MODEM STATUS
0C5A& B7 3F&      380                STA     ADDR8250;REG TO SEE IF DATA
0C5C& B6 40&      381                LDA     DATA8250;SET READY IS ACTIVE..
0C5E& CD 0B51&    382                JSR     RD8250   ;
0C61& 0B 40& 09   383                BRCLR   5,DATA8250,OUT8250C
0C64& B7 40&      384                STA     DATA8250;DSR ACTIVE SO WRITE
0C66& 3F 3F&      385                CLR     ADDR8250;THE CHARACTER.
0C68& CD 0B94&    386                JSR     WR8250   ;
0C6B& 20 0A       387                BRA     OUT8250D;EXIT.
0C6D& B7 40&      388      OUT8250C  STA     DATA8250;DSR NOT ACTIVE.
0C6F& B3 4A&      389                CPX     TIKSEC  ;CHECK FOR TIME OUT.
0C71& 26 DC       390                BNE     OUT8250L;
0C73& A6 10       391                LDA     #10H     ;TIME OUT ERROR.
0C75& B7 3F&      392                STA     ADDR8250;SET BIT IN ADDR8250.
0C77& BD A3&      393      OUT8250D  JSR     REGLOAD ;LOAD X & A REGS.
0C79& 81          394                RTS              ;
                  395      $EJ
```

```
                                396        ;************** PGMLOAD    *********************
                                397        ;**********************************************
                                398        ;
                                399        ;THIS SUBROUTINE WILL LOAD A NEW PROGRAM INTO
                                400        ;THE RAM CHIP FROM THE 8250 CONNECTED TO THE
                                401        ;PRINTER PORT.
                                402        ;
                                403        ;**********************************************
                                404        ;
                                405        ;   INPUT : (NONE)
                                406        ;
                                407        ;   OUTPUT :
                                408        ;           (PROGRAM LOADED TO RAM CHIP)
                                409        ;
                                410        ;   REGISTERS SAVED (Y/N) : Y
                                411        ;   IF "N" ABOVE THEN REGISTERS USED
                                412        ;           (* = MODIFIED):
                                413        ;
                                414        ;   FIELDS USED (* = MODIFIED):
                                415        ;                   XSW       /BIT:6,7
                                416        ;                  *ADDR8250
                                417        ;                  *DATA8250
                                418        ;                  *PCTRL
                                419        ;                  *PCTRH
                                420        ;                  *OPDATA
                                421        ;
                                422        ;   SUBROUTINES CALLED:
                                423        ;                   REGSAVE
                                424        ;                   REGLOAD
                                425        ;                   CHK8250
                                426        ;                   RST8250
                                427        ;                   OUT8250
                                428        ;                   INP8250
                                429        ;                   RAMWRIT
                                430        ;                   RAMREAD
                                431        ;
                                432        ;**********************************************
 0C7A& BD 94&                   433        PGMLOAD  JSR    REGSAVE  ;SAVE X & A REGS.
 0C7C& 1C 41&                   434                 BSET   6,XSW    ;SET RAM I/O TO
 0C7E& 1F 41&                   435                 BCLR   7,XSW    ;OP CODES
 0C80& CD 0BB2&                 436        PGMLOADA JSR    CHK8250  ;
 0C83& B6 3F&                   437                 LDA    ADDR8250 ;8250 CHIP
 0C85& 26 3D                    438                 BNE    PGMLOADJ ;ATTACHED?
 0C87& CD 0AFE&                 439                 JSR    RST8250  ;YES, RESET 8250.
 0C8A& A6 AA                    440                 LDA    #0AAH    ;WRITE #0AAH
 0C8C& B7 40&                   441                 STA    DATA8250 ;TO SERIAL
 0C8E& CD 0C42&                 442                 JSR    OUT8250  ;INTERFACE.
 0C91& B6 3F&                   443                 LDA    ADDR8250 ;
 0C93& A1 00                    444                 CMP    #0       ;ANY I/O
 0C95& 26 2D                    445                 BNE    PGMLOADJ ;ERRORS?
 0C97& A6 55                    446                 LDA    #55H     ;NO, WRITE #55H
 0C99& B7 40&                   447                 STA    DATA8250 ;TO SERIAL
 0C9B& CD 0C42&                 448                 JSR    OUT8250  ;INTERFACE.
 0C9E& B6 3F&                   449                 LDA    ADDR8250 ;
 0CA0& A1 00                    450                 CMP    #0       ;ANY I/O
 0CA2& 26 20                    451                 BNE    PGMLOADJ ;ERRORS?
 0CA4& CD 0BD6&                 452                 JSR    INP8250  ;NO, READ CHAR.
 0CA7& B6 3F&                   453                 LDA    ADDR8250 ;
 0CA9& A1 00                    454                 CMP    #0       ;ANY I/O
 0CAB& 26 17                    455                 BNE    PGMLOADJ ;ERRORS?
 0CAD& B6 40&                   456                 LDA    DATA8250 ;NO, LOAD CHAR.
 0CAF& A1 AA                    457                 CMP    #0AAH    ;IS CHAR = #0AAH?
 0CB1& 26 11                    458                 BNE    PGMLOADJ ;NO, THEN EXIT.
 0CB3& CD 0BD6&                 459                 JSR    INP8250  ;YES, READ ANOTHER.
 0CB6& B6 3F&                   460                 LDA    ADDR8250 ;
 0CB8& A1 00                    461                 CMP    #0       ;ANY I/O
 0CBA& 26 08                    462                 BNE    PGMLOADJ ;ERRORS?
 0CBC& B6 40&                   463                 LDA    DATA8250 ;NO, LOAD CHAR.
 0CBE& A1 55                    464                 CMP    #55H     ;IS CHAR = #55H?
 0CC0& 26 02                    465                 BNE    PGMLOADJ ;NO, THEN EXIT.
 0CC2& 20 03                    466                 BRA    PGMLOADX ;YES, CONTINUE.
 0CC4& CC 0CFF&                 467        PGMLOADJ JMP    PGMLOAD4 ;EXIT JUMP.
 0CC7& CD 0BD6&                 468        PGMLOADX JSR    INP8250  ;READ CHARACTER.
 0CCA& B6 3F&                   469                 LDA    ADDR8250 ;
```

| | | | | | |
|---|---|---|---|---|---|
| 0CCC& A1 00 | 470 | | CMP | #0 | ;ANY I/O |
| 0CCE& 26 F4 | 471 | | BNE | PGMLOADJ | ;ERRORS? |
| 0CD0& B6 40& | 472 | | LDA | DATA8250 | ;NO, LOAD CHAR. |
| 0CD2& B7 56& | 473 | | STA | PCTRH | ;TO PGM COUNTER HIGH. |
| 0CD4& CD 0BD6& | 474 | | JSR | INP8250 | ;READ NEXT CHAR. |
| 0CD7& B6 3F& | 475 | | LDA | ADDR8250; | |
| 0CD9& A1 00 | 476 | | CMP | #0 | ;ANY I/O |
| 0CDB& 26 E7 | 477 | | BNE | PGMLOADJ | ;ERRORS? |
| 0CDD& B6 40& | 478 | | LDA | DATA8250 | ;NO, LOAD CHAR. |
| 0CDF& B7 55& | 479 | | STA | PCTRL | ;TO PGM COUNTER LOW. |
| 0CE1& CD 0BD6& | 480 | PGMLOAD2 | JSR | INP8250 | ;READ NEXT CHAR. |
| 0CE4& B6 3F& | 481 | | LDA | ADDR8250; | |
| 0CE6& A1 00 | 482 | | CMP | #0 | ;ANY I/O |
| 0CE8& 26 34 | 483 | | BNE | PGMLOAD5 | ;ERRORS? |
| 0CEA& B6 40& | 484 | | LDA | DATA8250 | ;NO, LOAD CHAR. |
| 0CEC& B7 45& | 485 | | STA | OPDATA | ;TO OP CODE DATA. |
| 0CEE& CD 09A4& | 486 | | JSR | RAMWRIT | ;STORE IN RAM. |
| 0CF1& B6 55& | 487 | | LDA | PCTRL | ;LOAD PGM CTR LOW. |
| 0CF3& 26 02 | 488 | | BNE | PGMLOAD3 | ;CTR LOW = ZERO? |
| 0CF5& 3A 56& | 489 | | DEC | PCTRH | ;YES, CTR HIGH - 1. |
| 0CF7& 3A 55& | 490 | PGMLOAD3 | DEC | PCTRL | ;CTR LOW - 1. |
| 0CF9& B6 56& | 491 | | LDA | PCTRH | ;LOAD CTR HIGH. |
| 0CFB& A1 FF | 492 | | CMP | #0FFH | ;IS PGM COUNTER |
| 0CFD& 26 E2 | 493 | | BNE | PGMLOAD2 | ;< 0? |
| 0CFF& 3F 55& | 494 | PGMLOAD4 | CLR | PCTRL | ;YES, SET PGM CTR |
| 0D01& A6 01 | 495 | | LDA | #1 | ;TO #0100H. |
| 0D03& B7 56& | 496 | | STA | PCTRH | ; |
| 0D05& CD 09CA& | 497 | | JSR | RAMREAD | ;READ RAM. |
| 0D08& B6 45& | 498 | | LDA | OPDATA | ; |
| 0D0A& A1 AA | 499 | | CMP | #0AAH | ;0100 = #0AAH? |
| 0D0C& 26 10 | 500 | | BNE | PGMLOAD5 | ;IF NO THEN RESTART. |
| 0D0E& A6 01 | 501 | | LDA | #1 | ;SET PGM CTR |
| 0D10& B7 55& | 502 | | STA | PCTRL | ;TO #0101H. |
| 0D12& CD 09CA& | 503 | | JSR | RAMREAD | ;READ RAM. |
| 0D15& B6 45& | 504 | | LDA | OPDATA | ; |
| 0D17& A1 55 | 505 | | CMP | #055H | ;0101 = #55H? |
| 0D19& 26 03 | 506 | | BNE | PGMLOAD5 | ;IF NO THEN RESTART. |
| 0D1B& BD A3& | 507 | | JSR | REGLOAD | ;LOAD X & A REGS. |
| 0D1D& 81 | 508 | | RTS | | ; |
| 0D1E& 19 41& | 509 | PGMLOAD5 | BCLR | 4,XSW | ;SET FOR DISPLAY 0'S. |
| 0D20& B6 3F& | 510 | | LDA | ADDR8250 | ;GET I/O RETURN CODE. |
| 0D22& B7 48& | 511 | | STA | DISPWORD+1 | ;RIGHT 2 DIGITS. |
| 0D24& B6 40& | 512 | | LDA | DATA8250 | ;GET 8250 DATA. |
| 0D26& B7 47& | 513 | | STA | DISPWORD | ;LEFT 2 DIGITS. |
| 0D28& CD 06C8& | 514 | | JSR | DISPNUM | ;GO DISPLAY IT. |
| 0D2B& 16 1C& | 515 | | BSET | 3,SYSCTRL | ;HALT SYSTEM. |
| 0D2D& 04 02& EE | 516 | | BRSET | 2,PCDATA,PGMLOAD5 | ;START SW? |
| 0D30& CD 042E& | 517 | | JSR | LCDCLR | ;YES, CLEAR LCD. |
| 0D33& CC 0C80& | 518 | | JMP | PGMLOADA | ;TRY LOAD AGAIN. |
| | 519 | | | | |
| | 58 | | INCLUDE | "INSVECT.ASM" | ; INT. VECTORS |
| | 1 | | DEFSEG | SELFCHK,CLASS=DATA,START=0F30H | |
| | 2 | | SEG | SELFCHK | |
| 0000& (00C0) | 3 | | DS | 192 | |
| | 4 | | DEFSEG | VECTORS,CLASS=DATA,START=0FF0H | |
| | 5 | | SEG | VECTORS | |
| 0000& 1F11 | 6 | MSSREG | DW | 01F11H | ;Master Slice |
| | 7 | | | | ;select register |
| | 8 | | | | ; SEG11 - 15 = LCD |
| | 9 | | | | ; SEG16    = CH2 |
| | 10 | | | | ; SEG17    = CH3 |
| | 11 | | | | ; OSC2 used |
| | | | | | ; 0 second delay |
| 0002& (0002) | 12 | | DS | 2 | |
| 0004& 07E3& | 13 | TBVECT | DW | TBINT | |
| 0006& 0AB2& | 14 | ADCVECT | DW | ADCINT | |
| 0008& 08F4& | 15 | TIMVECT | DW | TIMINT | |
| 000A& 0779& | 16 | INTVECT | DW | SPCHBSY | |
| 000C& 03B6& | 17 | SWIVECT | DW | SWIINT | |
| 000E& 0000& | 18 | RSTVECT | DW | OPSTART | |
| | 19 | | | | |
| | 59 | | END | | |

While a presently preferred form of the present invention has been set forth hereinabove, it is to be understood that the invention is not limited thereby and in particular the steps of the inventive process are interchangeable, may be interchanged and are equivalent. It is to be understood that the specific details shown are merely illustrative and that the invention may be carried out in other ways without departing from the true spirit and scope of the following claims.

What is claimed:

1. A process of operating a glucose monitoring system comprising the steps of
   (a) selectively energizing one of a plurality of different color light emitting diodes to emit light against a test specimen strip with a glucose concentration falling within a range of differing glucose concentrations causing differing absorption spectra;
   (b) receiving conductive emissions from a selected diode through said test specimen strip with photo transistor means and converting the emissions with said photo transistor means into an electronic signal;
   (c) transmitting said electronic signal to a computer;
   (d) providing said computer with a characteristic data base comprising a plurality of records corresponding to each of a number of readout components, each of said records comprising a plurality of characteristic identifiers describing corresponding specimens and including at least characteristics in the categories of milliliters per deciliter, four digit number readout, acceptability indicator; and
   (e) displaying said characteristics.

2. The process as claimed in claim 1 wherein said characteristics which are displayed in step (e) are displayed by a printer.

3. The process as claimed in claim 1 wherein said characteristics which are displayed in step (e) are displayed by a speech synthesizer means.

4. The process as claimed in claim 1 wherein said characteristics which are displayed in step (e) are displayed by a CRT.

5. An apparatus for measuring chemical concentration on a media comprising;
   a housing, means in said housing for receiving a test media strip having an unknown concentration of test sample, a plurality of different monochromatic light emitting diodes mounted in said housing and connected to a power source, said light emitting diodes being adapted to be selectively powered at a preselected test sample concentration to transmit light through said test media strip with concentration of test sample, photo transistor means mounted in said housing, said photo transistor means being adapted to receive light from a specifically selected light emitting diode selected from said plurality of light emitting diodes which passes through said test media strip with test sample and transmit current proportional to an amount of light being received to an analog-to-digital converter, said analog-to-digital converter producing a digital signal and being connected to computer means which receives the digital signal and transmits selected information about the test sample concentration on the test media strip.

6. An apparatus for measuring chemical concentration as claimed in claim 5 wherein said light emitting diodes are red and green and are selectively powered by a power source and said apparatus includes switching means which switches the power source from the red light emitting diode to the green emitting diode at a preselected sample concentration sensed by a decrease in the transmission of light.

7. An apparatus as claimed in claim 5 wherein said selected information is transmitted to measurement and read out means for converting the signal to a read out indicative of at least one of either the absorbence or transmission of said test media strip with sample with respect to the wavelength of said monochromatic light reflecting a color change in a chromogenic indicator on said test media strip.

8. An apparatus as claimed in claim 5 wherein said sample is glucose.

* * * * *